(12) United States Patent
Ben-Haim et al.

(10) Patent No.: US 8,792,985 B2
(45) Date of Patent: Jul. 29, 2014

(54) GASTROINTESTINAL METHODS AND APPARATUS FOR USE IN TREATING DISORDERS AND CONTROLLING BLOOD SUGAR

(75) Inventors: Shlomo Ben-Haim, Caesarea (IL); Shao Policker, Moshav Zur Moshe (IL); Ofir Biton, Zichron Yaakov (IL); Tamar Harel, Haifa (IL)

(73) Assignee: Metacure Limited, Hamilton (BM)

( * ) Notice: Subject to any disclaimer, the term of this patent is extended or adjusted under 35 U.S.C. 154(b) by 617 days.

(21) Appl. No.: 11/336,099

(22) Filed: Jan. 20, 2006

(65) Prior Publication Data

US 2007/0027493 A1 Feb. 1, 2007

Related U.S. Application Data

(63) Continuation of application No. PCT/IL2004/000664, filed on Jul. 21, 2004.

(60) Provisional application No. 60/488,964, filed on Jul. 21, 2003.

(51) Int. Cl.
*A61N 1/36* (2006.01)

(52) U.S. Cl.
USPC ................................. 607/40; 607/41; 607/133

(58) Field of Classification Search
USPC ............................................. 607/40, 41, 133
See application file for complete search history.

(56) References Cited

U.S. PATENT DOCUMENTS

| | | |
|---|---|---|
| 1,918,386 A | 7/1933 | Esau |
| 2,593,067 A | 4/1952 | Spencer |
| 3,211,154 A | 10/1965 | Becker et al. |
| 3,411,507 A | 11/1968 | Wingrove |
| 3,516,412 A | 6/1970 | Ackerman |
| 3,541,390 A | 11/1970 | Jahnke |
| 3,572,345 A | 3/1971 | Auphan |
| 3,587,567 A | 6/1971 | Schiff |
| 3,650,277 A | 3/1972 | Sjostrand et al. |
| 3,651,805 A | 3/1972 | Breiling |
| 3,651,806 A | 3/1972 | Hirshberg |
| 3,658,051 A | 4/1972 | MacLean |
| 3,737,579 A | 6/1973 | Bolduc |

(Continued)

FOREIGN PATENT DOCUMENTS

| | | |
|---|---|---|
| EP | 0057048 | 8/1982 |
| EP | 0129483 | 12/1984 |

(Continued)

OTHER PUBLICATIONS

Yamada, "Effects of drugs on electromechanical activities of the stomach and duodenum of conscious dogs", Nippon Heikatsukin Gakkai Zasshi. Feb. 1983;19(1):25-35. (abstract only).

(Continued)

*Primary Examiner* — Joseph Dietrich

(74) *Attorney, Agent, or Firm* — William H. Dippert; Eckert Seamans Cherin & Mellott, LLC

(57) ABSTRACT

A method and apparatus are provided for treating a subject. An electrical signal is applied to at least one stomach site of the subject. The electrical signal is configured to reduce a rise in a blood glucose level of the subject, in order to treat the subject.

53 Claims, 13 Drawing Sheets

(56) References Cited

U.S. PATENT DOCUMENTS

| | | |
|---|---|---|
| 3,796,221 A | 3/1974 | Hagfors |
| 3,911,930 A | 10/1975 | Hagfors et al. |
| 3,924,641 A | 12/1975 | Weiss |
| 3,933,147 A | 1/1976 | Du Vall et al. |
| 3,942,536 A | 3/1976 | Mirowski et al. |
| 3,944,740 A | 3/1976 | Murase et al. |
| 3,952,750 A | 4/1976 | Mirowski et al. |
| 4,000,745 A | 1/1977 | Goldberg et al. |
| 4,010,758 A | 3/1977 | Rockland et al. |
| 4,030,509 A | 6/1977 | Heilman et al. |
| 4,055,190 A | 10/1977 | Tany |
| 4,106,494 A | 8/1978 | McEachern |
| 4,133,315 A | 1/1979 | Berman et al. |
| 4,164,216 A | 8/1979 | Person |
| 4,165,454 A | 8/1979 | Carlsson et al. |
| 4,168,711 A | 9/1979 | Cannon, III et al. |
| 4,177,818 A | 12/1979 | De Pedro |
| 4,184,493 A | 1/1980 | Langer et al. |
| 4,202,340 A | 5/1980 | Langer et al. |
| 4,223,678 A | 9/1980 | Langer et al. |
| 4,235,246 A | 11/1980 | Weiss |
| 4,237,895 A | 12/1980 | Johnson |
| 4,273,114 A | 6/1981 | Berkalow et al. |
| 4,280,503 A | 7/1981 | Ackerman |
| 4,293,734 A | 10/1981 | Pepper, Jr. |
| 4,312,354 A | 1/1982 | Walters |
| 4,313,448 A | 2/1982 | Stokes |
| 4,315,503 A | 2/1982 | Ryaby et al. |
| 4,316,472 A | 2/1982 | Mirowski et al. |
| 4,337,776 A | 7/1982 | Daly et al. |
| 4,342,896 A | 8/1982 | Teich |
| 4,354,153 A | 10/1982 | Lentz |
| 4,357,946 A | 11/1982 | Dutcher et al. |
| 4,369,791 A | 1/1983 | Friedman |
| 4,377,733 A | 3/1983 | Yamaguchi et al. |
| 4,378,023 A | 3/1983 | Trabucco |
| 4,384,585 A | 5/1983 | Zipes |
| 4,387,717 A | 6/1983 | Brownlee et al. |
| 4,403,614 A | 9/1983 | Engle et al. |
| 4,406,288 A | 9/1983 | Horwinski et al. |
| 4,407,288 A | 10/1983 | Langer et al. |
| 4,411,268 A | 10/1983 | Cox |
| 4,416,267 A | 11/1983 | Garren et al. |
| 4,428,366 A | 1/1984 | Findl et al. |
| 4,431,888 A | 2/1984 | Simpson |
| 4,440,172 A | 4/1984 | Langer |
| 4,447,693 A | 5/1984 | Buck |
| 4,452,254 A | 6/1984 | Goldberg et al. |
| 4,475,024 A | 10/1984 | Tateda |
| 4,485,805 A | 12/1984 | Foster, Jr. |
| 4,506,680 A | 3/1985 | Stokes |
| 4,537,195 A | 8/1985 | McDonnell |
| 4,537,203 A | 8/1985 | Machida |
| 4,543,738 A | 10/1985 | Mower |
| 4,543,956 A | 10/1985 | Herscovici |
| 4,550,221 A | 10/1985 | Mabusth |
| 4,552,150 A | 11/1985 | Zacouto |
| 4,554,922 A | 11/1985 | Prystowsky et al. |
| 4,554,992 A | 11/1985 | Kassai |
| 4,559,946 A | 12/1985 | Mower |
| 4,559,947 A | 12/1985 | Renger et al. |
| 4,566,456 A | 1/1986 | Koning et al. |
| 4,572,191 A | 2/1986 | Mirowski et al. |
| 4,592,339 A | 6/1986 | Kuzmak |
| 4,596,915 A | 6/1986 | Simpson |
| 4,628,934 A | 12/1986 | Pohndorf et al. |
| 4,637,397 A | 1/1987 | Jones et al. |
| 4,639,720 A | 1/1987 | Rympalski et al. |
| 4,651,716 A | 3/1987 | Forester et al. |
| 4,674,508 A | 6/1987 | DeCote |
| 4,679,572 A | 7/1987 | Baker, Jr. |
| 4,686,332 A | 8/1987 | Greanias et al. |
| 4,690,155 A | 9/1987 | Hess |
| 4,693,253 A | 9/1987 | Adams |
| 4,708,145 A | 11/1987 | Tacker et al. |
| 4,717,581 A | 1/1988 | Robblee |
| 4,726,279 A | 2/1988 | Kepler et al. |
| 4,726,379 A | 2/1988 | Altman et al. |
| 4,765,341 A | 8/1988 | Mower et al. |
| 4,807,632 A | 2/1989 | Liess et al. |
| 4,823,808 A | 4/1989 | Clegg et al. |
| 4,830,006 A | 5/1989 | Haluska et al. |
| 4,834,100 A | 5/1989 | Charms |
| 4,850,959 A | 7/1989 | Findl |
| 4,870,974 A | 10/1989 | Wang |
| 4,873,986 A | 10/1989 | Wallace |
| 4,878,553 A | 11/1989 | Yamanami et al. |
| 4,884,576 A | 12/1989 | Alt |
| 4,914,624 A | 4/1990 | Dunthorn et al. |
| 4,928,688 A | 5/1990 | Mower |
| 4,967,749 A | 11/1990 | Cohen |
| 4,971,058 A | 11/1990 | Pless et al. |
| 4,975,682 A | 12/1990 | Kerr et al. |
| 4,979,507 A | 12/1990 | Heinz et al. |
| 4,988,837 A | 1/1991 | Murakami et al. |
| 4,996,984 A | 3/1991 | Sweeney |
| 4,998,531 A | 3/1991 | Bocchi et al. |
| 4,998,532 A | 3/1991 | Griffith |
| 5,002,052 A | 3/1991 | Haluska et al. |
| 5,003,976 A | 4/1991 | Alt |
| 5,018,522 A | 5/1991 | Mehra |
| 5,020,544 A | 6/1991 | Dahl et al. |
| 5,022,396 A | 6/1991 | Watanabe |
| 5,025,787 A | 6/1991 | Sutherland et al. |
| 5,026,397 A | 6/1991 | Aoki et al. |
| 5,031,617 A | 7/1991 | Klettner |
| 5,041,107 A | 8/1991 | Heil, Jr. |
| 5,044,375 A | 9/1991 | Bach, Jr. et al. |
| 5,048,522 A | 9/1991 | Petrofsky |
| 5,050,612 A | 9/1991 | Matsumura |
| 5,063,929 A | 11/1991 | Bartelt et al. |
| 5,074,868 A | 12/1991 | Kuzmak |
| 5,083,564 A | 1/1992 | Scherlag |
| 5,083,565 A | 1/1992 | Parins |
| 5,085,218 A | 2/1992 | Heil et al. |
| 5,087,243 A | 2/1992 | Avitall |
| 5,097,832 A | 3/1992 | Buchanan |
| 5,097,833 A | 3/1992 | Campos |
| 5,097,843 A | 3/1992 | Soukup et al. |
| 5,101,814 A | 4/1992 | Palti |
| 5,103,804 A | 4/1992 | Abele et al. |
| 5,105,812 A | 4/1992 | Corman |
| 5,107,834 A | 4/1992 | Ideker et al. |
| 5,111,814 A | 5/1992 | Goldfarb |
| 5,111,815 A | 5/1992 | Mower |
| 5,129,394 A | 7/1992 | Mehra |
| 5,133,354 A | 7/1992 | Kallok |
| 5,137,021 A | 8/1992 | Wayne et al. |
| 5,144,554 A | 9/1992 | Zhang et al. |
| 5,154,501 A | 10/1992 | Svenson et al. |
| 5,156,147 A | 10/1992 | Warren et al. |
| 5,156,149 A | 10/1992 | Hudrlik |
| 5,161,527 A | 11/1992 | Nappholz et al. |
| 5,163,427 A | 11/1992 | Keimel |
| 5,163,428 A | 11/1992 | Pless |
| 5,172,690 A | 12/1992 | Nappholz et al. |
| 5,172,699 A | 12/1992 | Svenson et al. |
| 5,174,286 A | 12/1992 | Chirife |
| 5,184,616 A | 2/1993 | Weiss |
| 5,184,620 A | 2/1993 | Cudahy et al. |
| 5,185,620 A | 2/1993 | Cooper |
| 5,188,104 A | 2/1993 | Wernicke et al. |
| 5,188,106 A | 2/1993 | Nappholz et al. |
| 5,190,036 A | 3/1993 | Linder |
| 5,190,041 A | 3/1993 | Palti |
| 5,190,141 A | 3/1993 | Boldrini et al. |
| 5,199,428 A | 4/1993 | Obel et al. |
| 5,202,095 A | 4/1993 | Houchin et al. |
| 5,205,284 A | 4/1993 | Freeman |
| 5,213,098 A | 5/1993 | Bennett et al. |
| 5,226,429 A | 7/1993 | Kuzmak |
| 5,231,381 A | 7/1993 | Duwaer |
| 5,231,988 A | 8/1993 | Wernicke et al. |
| 5,233,985 A | 8/1993 | Hudrlik |

(56) References Cited

U.S. PATENT DOCUMENTS

| | | |
|---|---|---|
| 5,234,454 A | 8/1993 | Bangs |
| 5,236,413 A | 8/1993 | Feiring |
| 5,243,980 A | 9/1993 | Mehra et al. |
| 5,247,938 A | 9/1993 | Silverstein et al. |
| 5,263,480 A | 11/1993 | Wernicke et al. |
| 5,267,560 A | 12/1993 | Cohen |
| 5,281,219 A | 1/1994 | Kallok |
| 5,282,785 A | 2/1994 | Shapland et al. |
| 5,284,491 A | 2/1994 | Sutton et al. |
| 5,286,254 A | 2/1994 | Shapland et al. |
| 5,292,344 A | 3/1994 | Douglas |
| 5,305,745 A | 4/1994 | Zacouto |
| 5,314,463 A | 5/1994 | Camps et al. |
| 5,318,591 A | 6/1994 | Causey, III et al. |
| 5,320,543 A | 6/1994 | Barton et al. |
| 5,320,642 A | 6/1994 | Scherlag |
| 5,320,643 A | 6/1994 | Roline et al. |
| 5,324,327 A | 6/1994 | Cohen |
| 5,325,856 A | 7/1994 | Nitzsche et al. |
| 5,327,887 A | 7/1994 | Nowakowski |
| 5,346,506 A | 9/1994 | Mower et al. |
| 5,350,403 A | 9/1994 | Stroetmann et al. |
| 5,353,800 A | 10/1994 | Pohndorf et al. |
| 5,365,461 A | 11/1994 | Stein et al. |
| 5,366,485 A | 11/1994 | Kroll et al. |
| 5,366,486 A | 11/1994 | Zipes et al. |
| 5,368,028 A | 11/1994 | Palti |
| 5,368,040 A | 11/1994 | Carney |
| 5,370,665 A | 12/1994 | Hudrlik |
| 5,374,787 A | 12/1994 | Miller et al. |
| 5,381,160 A | 1/1995 | Landmeier |
| 5,386,835 A | 2/1995 | Elphick et al. |
| 5,386,837 A | 2/1995 | Sterzer |
| 5,387,419 A | 2/1995 | Levy et al. |
| 5,391,192 A | 2/1995 | Lu et al. |
| 5,391,199 A | 2/1995 | Ben-Haim |
| 5,397,344 A | 3/1995 | Garfield et al. |
| 5,398,683 A | 3/1995 | Edwards et al. |
| 5,402,151 A | 3/1995 | Duwaer |
| 5,411,531 A | 5/1995 | Hill et al. |
| 5,415,629 A | 5/1995 | Henley |
| 5,417,717 A | 5/1995 | Salo et al. |
| 5,419,763 A | 5/1995 | Hildebrand |
| 5,423,872 A | 6/1995 | Cigaina |
| 5,425,363 A | 6/1995 | Wang |
| 5,431,682 A | 7/1995 | Hedberg |
| 5,431,688 A | 7/1995 | Freeman |
| 5,431,693 A | 7/1995 | Schroeppel |
| 5,433,730 A | 7/1995 | Alt |
| 5,443,485 A | 8/1995 | Housworth et al. |
| 5,443,489 A | 8/1995 | Ben-Haim |
| 5,445,609 A | 8/1995 | Lattin et al. |
| 5,447,520 A | 9/1995 | Spano et al. |
| 5,447,525 A | 9/1995 | Powell et al. |
| 5,447,526 A | 9/1995 | Karsdon |
| 5,449,368 A | 9/1995 | Kuzmak |
| 5,451,751 A | 9/1995 | Takimoto et al. |
| 5,458,568 A | 10/1995 | Racchini et al. |
| 5,464,020 A | 11/1995 | Lerner |
| 5,464,429 A | 11/1995 | Hedberg et al. |
| 5,468,254 A | 11/1995 | Hahn et al. |
| 5,472,453 A | 12/1995 | Alt |
| 5,476,484 A | 12/1995 | Hedberg |
| 5,476,485 A | 12/1995 | Weinberg et al. |
| 5,476,487 A | 12/1995 | Sholder |
| 5,476,497 A | 12/1995 | Mower et al. |
| 5,480,422 A | 1/1996 | Ben-haim |
| 5,482,052 A | 1/1996 | Lerner |
| 5,489,293 A | 2/1996 | Pless et al. |
| 5,495,077 A | 2/1996 | Miller et al. |
| 5,499,971 A | 3/1996 | Shapland et al. |
| 5,501,662 A | 3/1996 | Hofmann |
| 5,505,700 A | 4/1996 | Leone et al. |
| 5,510,813 A | 4/1996 | Makinwa et al. |
| 5,514,162 A | 5/1996 | Bornzin et al. |
| 5,514,175 A | 5/1996 | Kim et al. |
| 5,520,642 A | 5/1996 | Bigagli et al. |
| 5,522,853 A | 6/1996 | Kroll |
| 5,527,345 A | 6/1996 | Infinger |
| 5,528,002 A | 6/1996 | Katabami |
| 5,531,764 A | 7/1996 | Adams et al. |
| 5,534,015 A | 7/1996 | Kroll et al. |
| 5,540,722 A | 7/1996 | Clare et al. |
| 5,540,730 A | 7/1996 | Terry, Jr. et al. |
| 5,540,734 A | 7/1996 | Zabara |
| 5,543,589 A | 8/1996 | Buchana et al. |
| 5,546,951 A | 8/1996 | Ben-haim |
| 5,549,646 A | 8/1996 | Katz et al. |
| 5,551,425 A | 9/1996 | Essen-Moller |
| 5,552,150 A | 9/1996 | Horrobin et al. |
| 5,556,421 A | 9/1996 | Prutchi et al. |
| 5,556,760 A | 9/1996 | Nakamura et al. |
| 5,558,640 A | 9/1996 | Pfeiler et al. |
| 5,561,165 A | 10/1996 | Lautt et al. |
| 5,562,708 A | 10/1996 | Combs et al. |
| 5,562,720 A | 10/1996 | Stern et al. |
| 5,565,632 A | 10/1996 | Ogawa |
| 5,568,809 A | 10/1996 | Ben-Haim |
| 5,571,143 A | 11/1996 | Hoegnelid et al. |
| 5,571,997 A | 11/1996 | Gray et al. |
| 5,578,061 A | 11/1996 | Stroetmann et al. |
| 5,584,803 A | 12/1996 | Stevens et al. |
| 5,584,804 A | 12/1996 | Klatz et al. |
| 5,584,868 A | 12/1996 | Salo et al. |
| 5,587,200 A | 12/1996 | Lorenz et al. |
| 5,589,856 A | 12/1996 | Stein et al. |
| 5,601,604 A | 2/1997 | Vincent |
| 5,601,609 A | 2/1997 | Duncan |
| 5,601,611 A | 2/1997 | Fayram et al. |
| 5,616,268 A | 4/1997 | Carr |
| 5,620,468 A | 4/1997 | Mongeon et al. |
| 5,622,687 A | 4/1997 | Krishnan et al. |
| 5,626,622 A | 5/1997 | Cooper |
| 5,632,267 A | 5/1997 | Hoegnelid et al. |
| 5,634,895 A | 6/1997 | Igo et al. |
| 5,634,899 A | 6/1997 | Shapland et al. |
| 5,649,966 A | 7/1997 | Noren et al. |
| 5,651,378 A | 7/1997 | Matheny et al. |
| 5,654,030 A | 8/1997 | Munshi et al. |
| 5,662,687 A | 9/1997 | Hedberg et al. |
| 5,670,755 A | 9/1997 | Kwon |
| 5,674,251 A | 10/1997 | Combs et al. |
| 5,674,259 A | 10/1997 | Gray |
| 5,683,429 A | 11/1997 | Mehra |
| 5,683,431 A | 11/1997 | Wang |
| 5,687,734 A | 11/1997 | Dempsey et al. |
| 5,690,691 A | 11/1997 | Chen et al. |
| 5,694,945 A | 12/1997 | Ben-haim |
| 5,697,953 A | 12/1997 | Kroll et al. |
| 5,704,368 A | 1/1998 | Asano et al. |
| 5,713,924 A | 2/1998 | Min et al. |
| 5,713,929 A | 2/1998 | Hess et al. |
| 5,713,935 A | 2/1998 | Prutchi et al. |
| 5,716,385 A | 2/1998 | Mittal et al. |
| 5,720,768 A | 2/1998 | Verboven-Nelissen |
| 5,727,558 A | 3/1998 | Hakki et al. |
| 5,735,876 A | 4/1998 | Kroll et al. |
| 5,738,096 A | 4/1998 | Ben-Haim |
| 5,738,105 A | 4/1998 | Kroll |
| 5,741,211 A | 4/1998 | Renirie et al. |
| 5,741,791 A | 4/1998 | Olsen |
| 5,749,906 A | 5/1998 | Kieval et al. |
| 5,755,740 A | 5/1998 | Nappholz |
| 5,777,607 A | 7/1998 | Koolen |
| 5,779,661 A | 7/1998 | Stephen et al. |
| 5,782,876 A | 7/1998 | Flammang |
| 5,782,881 A | 7/1998 | Lu et al. |
| 5,783,951 A | 7/1998 | Inoue et al. |
| 5,790,106 A | 8/1998 | Hirano et al. |
| 5,790,107 A | 8/1998 | Kasser et al. |
| 5,792,189 A | 8/1998 | Gray et al. |
| 5,792,198 A | 8/1998 | Nappholz |
| 5,792,208 A | 8/1998 | Gray |
| 5,792,210 A | 8/1998 | Wamubu et al. |

(56) References Cited

U.S. PATENT DOCUMENTS

| | | |
|---|---|---|
| 5,795,304 A | 8/1998 | Sun et al. |
| 5,797,967 A | 8/1998 | KenKnight |
| 5,800,464 A | 9/1998 | Kieval |
| 5,807,234 A | 9/1998 | Bui et al. |
| 5,807,306 A | 9/1998 | Shapland et al. |
| 5,814,079 A | 9/1998 | Kieval |
| 5,824,016 A | 10/1998 | Ekwall |
| 5,825,352 A | 10/1998 | Bisset et al. |
| 5,836,994 A | 11/1998 | Bourgeois |
| 5,837,006 A | 11/1998 | Ocel et al. |
| 5,841,078 A | 11/1998 | Miller et al. |
| 5,854,881 A | 12/1998 | Yoshida et al. |
| 5,861,014 A | 1/1999 | Familoni |
| 5,865,787 A | 2/1999 | Shapland et al. |
| 5,868,141 A | 2/1999 | Ellias |
| 5,871,506 A | 2/1999 | Mower |
| 5,906,607 A | 5/1999 | Taylor et al. |
| 5,911,223 A | 6/1999 | Weaver et al. |
| 5,913,876 A | 6/1999 | Taylor et al. |
| 5,914,465 A | 6/1999 | Allen et al. |
| 5,919,216 A | 7/1999 | Houben et al. |
| 5,920,309 A | 7/1999 | Bisset et al. |
| 5,925,070 A | 7/1999 | King et al. |
| 5,927,284 A | 7/1999 | Borst et al. |
| 5,938,669 A | 8/1999 | Klaiber et al. |
| 5,954,761 A | 9/1999 | Machek et al. |
| 5,956,020 A | 9/1999 | D'Amico et al. |
| 5,961,871 A | 10/1999 | Bible et al. |
| 5,962,246 A | 10/1999 | Ladner et al. |
| 5,979,449 A | 11/1999 | Steer |
| 5,991,649 A | 11/1999 | Garfield et al. |
| 5,995,872 A | 11/1999 | Bourgeois |
| 6,002,594 A | 12/1999 | Ledin et al. |
| 6,006,134 A | 12/1999 | Hill et al. |
| 6,023,640 A | 2/2000 | Ross |
| 6,026,326 A | 2/2000 | Bardy |
| 6,026,626 A | 2/2000 | Fisher |
| 6,032,074 A | 2/2000 | Collins |
| 6,032,672 A | 3/2000 | Taylor |
| 6,037,882 A | 3/2000 | Levy |
| 6,041,252 A | 3/2000 | Walker et al. |
| 6,041,258 A | 3/2000 | Cigaina et al. |
| 6,057,374 A | 5/2000 | Huntington et al. |
| 6,066,163 A | 5/2000 | John |
| 6,067,470 A | 5/2000 | Mower |
| 6,067,991 A | 5/2000 | Forsell |
| 6,071,305 A | 6/2000 | Brown et al. |
| 6,075,520 A | 6/2000 | Inoue et al. |
| 6,083,249 A | 7/2000 | Familoni |
| 6,086,582 A | 7/2000 | Altman et al. |
| 6,091,992 A | 7/2000 | Bourgeois |
| 6,092,528 A | 7/2000 | Edwards |
| 6,093,167 A | 7/2000 | Houben et al. |
| 6,096,361 A | 8/2000 | Yamane et al. |
| 6,104,955 A | 8/2000 | Bourgeois |
| 6,115,635 A | 9/2000 | Bourgeois |
| 6,122,536 A | 9/2000 | Sun et al. |
| 6,128,007 A | 10/2000 | Seybold et al. |
| 6,129,685 A | 10/2000 | Howard |
| 6,132,372 A | 10/2000 | Essen-Moller |
| 6,133,906 A | 10/2000 | Geaghan |
| 6,135,978 A | 10/2000 | Houben et al. |
| 6,135,987 A | 10/2000 | Tsai et al. |
| 6,136,019 A | 10/2000 | Mower |
| 6,141,586 A | 10/2000 | Mower |
| 6,141,587 A | 10/2000 | Mower |
| 6,151,586 A | 11/2000 | Brown |
| 6,178,351 B1 | 1/2001 | Mower |
| 6,185,452 B1 | 2/2001 | Schulman et al. |
| 6,216,045 B1 | 4/2001 | Black et al. |
| 6,233,484 B1 | 5/2001 | Ben-Haim et al. |
| 6,233,487 B1 | 5/2001 | Mika et al. |
| 6,236,887 B1 | 5/2001 | Ben-Haim et al. |
| 6,239,389 B1 | 5/2001 | Allen et al. |
| 6,243,607 B1 | 6/2001 | Mintchev et al. |
| 6,249,697 B1 | 6/2001 | Asano et al. |
| 6,261,280 B1 | 7/2001 | Houben et al. |
| 6,278,443 B1 | 8/2001 | Amro et al. |
| 6,285,906 B1 | 9/2001 | Ben-Haim et al. |
| 6,292,693 B1 | 9/2001 | Darvish et al. |
| 6,292,704 B1 | 9/2001 | Malonek et al. |
| 6,295,470 B1 | 9/2001 | Mower |
| 6,296,693 B1 | 10/2001 | McCarthy |
| 6,298,254 B2 | 10/2001 | Tamada |
| 6,298,268 B1 | 10/2001 | Ben-Haim et al. |
| 6,317,631 B1 | 11/2001 | Ben-Haim et al. |
| 6,330,476 B1 | 12/2001 | Ben-Haim |
| 6,334,073 B1 | 12/2001 | Levine |
| 6,337,995 B1 | 1/2002 | Mower |
| 6,341,235 B1 | 1/2002 | Mower |
| 6,343,232 B1 | 1/2002 | Mower |
| 6,363,279 B1 | 3/2002 | Ben-Haim et al. |
| 6,363,937 B1 | 4/2002 | Hovda et al. |
| 6,381,495 B1 | 4/2002 | Jenkins |
| 6,392,636 B1 | 5/2002 | Ferrari et al. |
| 6,405,732 B1 | 6/2002 | Edwards |
| 6,411,842 B1 | 6/2002 | Cigaina et al. |
| 6,411,847 B1 | 6/2002 | Mower |
| 6,415,178 B1 | 7/2002 | Ben-Haim et al. |
| 6,417,846 B1 | 7/2002 | Lee |
| 6,424,864 B1 | 7/2002 | Matsuura |
| 6,427,089 B1 | 7/2002 | Knowlton |
| 6,433,069 B1 | 8/2002 | Oeltjen et al. |
| 6,449,511 B1 | 9/2002 | Mintchev et al. |
| 6,452,514 B1 | 9/2002 | Philipp |
| 6,453,199 B1 | 9/2002 | Kobozev |
| 6,454,699 B1 | 9/2002 | Forsell |
| 6,463,323 B1 | 10/2002 | Conrad-Vlasak et al. |
| 6,463,324 B1 | 10/2002 | Ben-Haim et al. |
| 6,473,069 B1 | 10/2002 | Gerpheide |
| 6,476,766 B1 | 11/2002 | Cohen |
| 6,498,944 B1 | 12/2002 | Ben-haim et al. |
| 6,504,530 B1 | 1/2003 | Wilson et al. |
| 6,505,745 B1 | 1/2003 | Anderson |
| 6,507,093 B2 | 1/2003 | Kaneda et al. |
| 6,535,764 B2 | 3/2003 | Imran et al. |
| RE38,119 E | 5/2003 | Mower |
| 6,558,345 B1 | 5/2003 | Houben et al. |
| 6,567,700 B1 | 5/2003 | Turcott et al. |
| 6,570,557 B1 | 5/2003 | Westerman et al. |
| 6,571,127 B1 | 5/2003 | Ben-Haim et al. |
| 6,572,542 B1 | 6/2003 | Houben et al. |
| 6,583,676 B2 | 6/2003 | Krah et al. |
| 6,584,348 B2 | 6/2003 | Glukhovsky |
| 6,587,093 B1 | 7/2003 | Shaw et al. |
| 6,587,721 B1 | 7/2003 | Prutchi et al. |
| 6,591,137 B1 | 7/2003 | Fischell et al. |
| 6,594,515 B2 | 7/2003 | Watson |
| 6,600,953 B2 | 7/2003 | Flesler et al. |
| 6,605,039 B2 | 8/2003 | Houben et al. |
| 6,606,523 B1 | 8/2003 | Jenkins |
| 6,609,025 B2 | 8/2003 | Barrett et al. |
| 6,611,258 B1 | 8/2003 | Tanaka et al. |
| 6,612,983 B1 | 9/2003 | Marchal |
| 6,630,123 B1 | 10/2003 | Woltering et al. |
| 6,633,280 B1 | 10/2003 | Matsumoto et al. |
| 6,634,895 B2 | 10/2003 | Agro |
| 6,652,444 B1 | 11/2003 | Ross |
| 6,658,297 B2 | 12/2003 | Loeb |
| 6,667,740 B2 | 12/2003 | Ely et al. |
| 6,684,104 B2 | 1/2004 | Gordon et al. |
| 6,690,156 B1 | 2/2004 | Weiner et al. |
| 6,690,963 B2 | 2/2004 | Ben-haim et al. |
| 6,735,477 B2 | 5/2004 | Levine |
| 6,745,079 B2 | 6/2004 | King |
| 6,754,536 B2 | 6/2004 | Swoyer et al. |
| 6,762,752 B2 | 7/2004 | Perski et al. |
| 6,781,577 B2 | 8/2004 | Shigetaka |
| 6,810,286 B2 | 10/2004 | Donovan et al. |
| 6,826,428 B1 | 11/2004 | Chen et al. |
| 6,832,114 B1 | 12/2004 | Whitehurst et al. |
| 6,852,110 B2 | 2/2005 | Roy et al. |
| 6,853,862 B1 * | 2/2005 | Marchal et al. ............... 607/40 |
| 6,869,431 B2 | 3/2005 | Maguire et al. |

(56) References Cited

U.S. PATENT DOCUMENTS

| | | |
|---|---|---|
| 6,876,885 B2 | 4/2005 | Swoyer et al. |
| 6,895,279 B2 | 5/2005 | Loeb et al. |
| 6,918,906 B2 | 7/2005 | Long |
| 6,919,205 B2 | 7/2005 | Brighton |
| 6,939,349 B2 | 9/2005 | Fleischman et al. |
| 6,947,792 B2 | 9/2005 | Ben-Haim et al. |
| 6,949,081 B1 | 9/2005 | Chance |
| 6,952,613 B2 | 10/2005 | Swoyer et al. |
| 6,993,391 B2 | 1/2006 | Flesler et al. |
| 7,006,871 B1 | 2/2006 | Darvish et al. |
| 7,027,863 B1 | 4/2006 | Prutchi et al. |
| 7,043,295 B2 | 5/2006 | Starkebaum |
| 7,054,690 B2 | 5/2006 | Imran |
| 7,062,318 B2 | 6/2006 | Ben-Haim et al. |
| 7,076,305 B2 | 7/2006 | Imran et al. |
| 7,076,306 B2 | 7/2006 | Marchal et al. |
| 7,092,753 B2 | 8/2006 | Darvish et al. |
| 7,120,497 B2 | 10/2006 | Ben-Haim et al. |
| 7,167,748 B2 | 1/2007 | Ben-Haim et al. |
| 7,171,263 B2 | 1/2007 | Darvish et al. |
| 7,190,997 B1 | 3/2007 | Darvish et al. |
| 7,218,963 B2 | 5/2007 | Ben-haim et al. |
| 7,221,978 B2 | 5/2007 | Ben-Haim et al. |
| 7,440,806 B1 | 10/2008 | Whitehurst et al. |
| 7,460,907 B1 | 12/2008 | Darvish et al. |
| 7,840,262 B2 | 11/2010 | Mika et al. |
| 7,966,071 B2 | 6/2011 | Ben-Haim et al. |
| 2001/0011543 A1 | 8/2001 | Forsell |
| 2002/0026141 A1 | 2/2002 | Houben et al. |
| 2002/0032444 A1 | 3/2002 | Mische |
| 2002/0052632 A1 | 5/2002 | Ben-Haim et al. |
| 2002/0065455 A1 | 5/2002 | Ben-haim et al. |
| 2002/0081732 A1 | 6/2002 | Bowlin et al. |
| 2002/0103424 A1 | 8/2002 | Swoyer et al. |
| 2002/0123771 A1 | 9/2002 | Ideker et al. |
| 2002/0161414 A1* | 10/2002 | Flesler et al. ................... 607/40 |
| 2002/0162836 A1 | 11/2002 | Taino et al. |
| 2002/0183682 A1 | 12/2002 | Darvish et al. |
| 2002/0183686 A1 | 12/2002 | Darvish et al. |
| 2003/0018367 A1 | 1/2003 | DiLorenzo |
| 2003/0028221 A1 | 2/2003 | Zhu et al. |
| 2003/0040777 A1 | 2/2003 | Shemer et al. |
| 2003/0045919 A1 | 3/2003 | Swoyer et al. |
| 2003/0055464 A1 | 3/2003 | Darvish et al. |
| 2003/0055465 A1 | 3/2003 | Ben-Haim et al. |
| 2003/0055466 A1 | 3/2003 | Ben-Haim et al. |
| 2003/0055467 A1 | 3/2003 | Ben-Haim et al. |
| 2003/0066536 A1 | 4/2003 | Forsell |
| 2003/0100889 A1 | 5/2003 | Duverger et al. |
| 2003/0144708 A1 | 7/2003 | Starkebaum |
| 2003/0167476 A1 | 9/2003 | Conklin |
| 2003/0181958 A1 | 9/2003 | Doubak, III |
| 2003/0188899 A1 | 10/2003 | Chao et al. |
| 2003/0195600 A1 | 10/2003 | Tronnes et al. |
| 2003/0208212 A1 | 11/2003 | Cigaina |
| 2003/0208242 A1 | 11/2003 | Harel et al. |
| 2003/0211475 A1 | 11/2003 | Roberts |
| 2003/0220678 A1 | 11/2003 | Tronnes et al. |
| 2004/0044376 A1 | 3/2004 | Flesler et al. |
| 2004/0059393 A1 | 3/2004 | Policker et al. |
| 2004/0088023 A1 | 5/2004 | Imran |
| 2004/0095333 A1 | 5/2004 | Morag et al. |
| 2004/0105040 A1 | 6/2004 | Oh et al. |
| 2004/0106954 A1 | 6/2004 | Whitehurst et al. |
| 2004/0107004 A1 | 6/2004 | Levine et al. |
| 2004/0134904 A1 | 7/2004 | Clemen |
| 2004/0138710 A1 | 7/2004 | Shemer et al. |
| 2004/0147816 A1 | 7/2004 | Policker et al. |
| 2004/0155871 A1 | 8/2004 | Perski et al. |
| 2004/0158138 A1 | 8/2004 | Kilcoyne et al. |
| 2004/0158289 A1 | 8/2004 | Girouard et al. |
| 2004/0162469 A1 | 8/2004 | Imran |
| 2004/0162595 A1 | 8/2004 | Foley |
| 2004/0167583 A1 | 8/2004 | Knudson et al. |
| 2004/0193184 A1 | 9/2004 | Laufer et al. |
| 2004/0193229 A1* | 9/2004 | Starkebaum et al. ........... 607/40 |
| 2004/0230273 A1 | 11/2004 | Cates et al. |
| 2004/0232140 A1 | 11/2004 | Kanzaki et al. |
| 2004/0236316 A1 | 11/2004 | Danitz et al. |
| 2004/0243190 A1 | 12/2004 | Ben-Haim et al. |
| 2004/0243211 A1 | 12/2004 | Colliou et al. |
| 2004/0249421 A1* | 12/2004 | Harel et al. ..................... 607/40 |
| 2005/0020965 A1 | 1/2005 | Vail |
| 2005/0021101 A1 | 1/2005 | Chen et al. |
| 2005/0033396 A1 | 2/2005 | Ospyka |
| 2005/0055038 A1 | 3/2005 | Kelleher et al. |
| 2005/0065505 A1 | 3/2005 | Ryan |
| 2005/0065553 A1 | 3/2005 | Ben Ezra et al. |
| 2005/0075654 A1 | 4/2005 | Kelleher |
| 2005/0090873 A1 | 4/2005 | Imran |
| 2005/0095227 A1 | 5/2005 | Rosenzweig et al. |
| 2005/0107829 A1 | 5/2005 | Edwards et al. |
| 2005/0143784 A1 | 6/2005 | Imran |
| 2005/0149142 A1 | 7/2005 | Starkebaum |
| 2005/0164925 A1 | 7/2005 | Jakubowski et al. |
| 2005/0183732 A1 | 8/2005 | Edwards |
| 2005/0192542 A1 | 9/2005 | Dev et al. |
| 2005/0192615 A1 | 9/2005 | Torre et al. |
| 2005/0203500 A1 | 9/2005 | Saadat et al. |
| 2005/0209653 A1 | 9/2005 | Herbert et al. |
| 2005/0222638 A1 | 10/2005 | Foley et al. |
| 2006/0036126 A1 | 2/2006 | Ross et al. |
| 2006/0074459 A1 | 4/2006 | Flesler et al. |
| 2006/0079475 A1 | 4/2006 | Zhang et al. |
| 2006/0085045 A1 | 4/2006 | Harel et al. |
| 2006/0097991 A1 | 5/2006 | Hotelling et al. |
| 2006/0142803 A1 | 6/2006 | Mintchev |
| 2006/0173238 A1 | 8/2006 | Starkebaum |
| 2006/0184207 A1 | 8/2006 | Darvish et al. |
| 2006/0247718 A1 | 11/2006 | Starkebaum |
| 2007/0016262 A1 | 1/2007 | Gross et al. |
| 2007/0027487 A1 | 2/2007 | Mika et al. |
| 2007/0027490 A1 | 2/2007 | Ben-Haim et al. |
| 2007/0027493 A1 | 2/2007 | Ben-Haim et al. |
| 2007/0051849 A1 | 3/2007 | Watts et al. |
| 2007/0060812 A1 | 3/2007 | Harel et al. |
| 2007/0060971 A1 | 3/2007 | Glasberg et al. |
| 2007/0088393 A1 | 4/2007 | Ben-Haim et al. |
| 2007/0092446 A1 | 4/2007 | Haddad et al. |
| 2007/0156177 A1 | 7/2007 | Harel et al. |
| 2007/0161851 A1 | 7/2007 | Takizawa et al. |
| 2007/0162079 A1 | 7/2007 | Shemer et al. |
| 2007/0171211 A1 | 7/2007 | Perski et al. |
| 2007/0179556 A1 | 8/2007 | Ben-Haim et al. |
| 2007/0185540 A1 | 8/2007 | Ben-Haim et al. |
| 2007/0239216 A9 | 10/2007 | Shemer et al. |
| 2007/0293901 A1 | 12/2007 | Rousso et al. |
| 2007/0299320 A1 | 12/2007 | Policker et al. |
| 2008/0046062 A1 | 2/2008 | Camps et al. |
| 2008/0051849 A1 | 2/2008 | Ben-Haim et al. |
| 2008/0058879 A1 | 3/2008 | Ben-Haim et al. |
| 2008/0058889 A1 | 3/2008 | Ben-Haim et al. |
| 2008/0058891 A1 | 3/2008 | Ben-Haim et al. |
| 2008/0065159 A1 | 3/2008 | Ben-Haim et al. |
| 2008/0065163 A1 | 3/2008 | Ben-Haim et al. |
| 2008/0065164 A1 | 3/2008 | Ben-Haim et al. |
| 2008/0065168 A1 | 3/2008 | Bitton et al. |
| 2008/0077174 A1 | 3/2008 | Mische |
| 2008/0140142 A1 | 6/2008 | Darvish et al. |
| 2008/0178684 A1 | 7/2008 | Spehr |
| 2008/0188837 A1 | 8/2008 | Belsky et al. |
| 2009/0062893 A1 | 3/2009 | Spehr |
| 2009/0088816 A1 | 4/2009 | Harel et al. |
| 2009/0118797 A1 | 5/2009 | Kliger et al. |
| 2009/0131993 A1 | 5/2009 | Rousso et al. |
| 2009/0204063 A1 | 8/2009 | Policker et al. |
| 2009/0281449 A1 | 11/2009 | Thrower et al. |
| 2009/0292324 A1 | 11/2009 | Rousso et al. |
| 2010/0016923 A1 | 1/2010 | Rousso et al. |
| 2010/0228105 A1 | 9/2010 | Policker et al. |
| 2010/0305468 A1 | 12/2010 | Policker et al. |
| 2010/0324644 A1 | 12/2010 | Levi et al. |

(56) References Cited

U.S. PATENT DOCUMENTS

FOREIGN PATENT DOCUMENTS

| | | |
|---|---|---|
| EP | 144705 | 6/1985 |
| EP | 0148687 | 7/1985 |
| EP | 0156593 | 10/1985 |
| EP | 0250931 | 1/1988 |
| EP | 0268379 | 5/1988 |
| EP | 0314078 | 5/1989 |
| EP | 0421780 | 4/1991 |
| EP | 0481684 | 4/1992 |
| EP | 0503839 | 9/1992 |
| EP | 0528751 | 2/1993 |
| EP | 0220916 | 4/1994 |
| EP | 0727241 | 8/1996 |
| EP | 0996482 | 5/2000 |
| EP | 1036545 | 9/2000 |
| EP | 1263498 | 12/2002 |
| EP | 1 447 052 | 8/2004 |
| EP | 1447632 | 8/2004 |
| EP | 0910429 | 3/2005 |
| EP | 1515102 | 3/2005 |
| GB | 1394171 | 5/1975 |
| GB | 2033587 | 5/1980 |
| GB | 2280377 | 2/1995 |
| JP | 62-112530 | 5/1987 |
| JP | 62-275471 | 11/1987 |
| JP | 04-117967 | 4/1992 |
| JP | 04-282168 | 10/1992 |
| JP | 04-365493 | 12/1992 |
| JP | 06-169998 | 6/1994 |
| JP | 06-193884 | 7/1994 |
| JP | 06-506619 | 7/1994 |
| JP | 06-310268 | 11/1994 |
| JP | 07-503865 | 4/1995 |
| JP | 07-126600 | 5/1995 |
| JP | 07-144024 | 6/1995 |
| JP | 07-508662 | 9/1995 |
| JP | 08-064359 | 3/1996 |
| JP | 08-243176 | 9/1996 |
| JP | 09-229372 | 9/1997 |
| JP | 2001-086967 | 4/2001 |
| JP | 2003/319945 | 11/2003 |
| JP | 2003319945 | 11/2003 |
| RU | 2014844 | 6/1994 |
| RU | 1827793 | 5/1995 |
| RU | 2055606 | 3/1996 |
| RU | 2075980 | 3/1997 |
| RU | 2077273 | 4/1997 |
| RU | 2078547 | 5/1997 |
| RU | 2260451 | 10/2001 |
| SU | 386634 | 10/1973 |
| SU | 0386634 | 10/1973 |
| SU | 0553977 | 5/1977 |
| SU | 553977 | 5/1977 |
| SU | 0709078 | 1/1980 |
| SU | 0831131 | 5/1981 |
| SU | 831131 | 5/1981 |
| SU | 1039506 | 9/1983 |
| SU | 1147408 | 3/1985 |
| WO | WO 91/19534 | 12/1991 |
| WO | WO 92/00716 | 1/1992 |
| WO | WO 92/13592 | 8/1992 |
| WO | WO 93/02743 | 2/1993 |
| WO | WO 93/02745 | 2/1993 |
| WO | WO 93/08874 | 5/1993 |
| WO | WO 93/18820 | 9/1993 |
| WO | WO 94/01172 | 1/1994 |
| WO | WO 94/17855 | 8/1994 |
| WO | WO 95/02995 | 2/1995 |
| WO | WO 95/08316 | 3/1995 |
| WO | WO 96/05768 | 2/1996 |
| WO | WO 96/10358 | 4/1996 |
| WO | WO 96/16696 | 6/1996 |
| WO | WO 97/15227 | 1/1997 |
| WO | WO 97/06849 | 2/1997 |
| WO | WO 97/24981 | 7/1997 |
| WO | WO 97/24983 | 7/1997 |
| WO | WO 97/25098 | 7/1997 |
| WO | WO 97/25101 | 7/1997 |
| WO | WO 97/26042 | 7/1997 |
| WO | WO 97/27900 | 7/1997 |
| WO | WO 97/29679 | 8/1997 |
| WO | WO 97/29682 | 8/1997 |
| WO | WO 97/29684 | 8/1997 |
| WO | WO 97/29700 | 8/1997 |
| WO | WO 97/29701 | 8/1997 |
| WO | WO 97/29709 | 8/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/11840 | 3/1998 |
| WO | WO 98/15317 | 4/1998 |
| WO | WO 98/19719 | 5/1998 |
| WO | WO 98/56378 | 12/1998 |
| WO | WO 98/57701 | 12/1998 |
| WO | WO 99/03533 | 1/1999 |
| WO | WO 99/06105 | 2/1999 |
| WO | WO 99/09971 | 3/1999 |
| WO | WO 99/55360 | 4/1999 |
| WO | WO 99/24110 | 5/1999 |
| WO | WO 99/29307 | 6/1999 |
| WO | WO 99/59548 | 11/1999 |
| WO | WO 00/01443 | 1/2000 |
| WO | WO 00/04947 | 2/2000 |
| WO | WO 00/16741 | 3/2000 |
| WO | WO 00/27475 | 5/2000 |
| WO | WO 00/42914 | 7/2000 |
| WO | WO 00/12525 | 9/2000 |
| WO | WO 00/53257 | 9/2000 |
| WO | WO 00/61223 | 10/2000 |
| WO | WO 00/74773 | 12/2000 |
| WO | WO 01/10375 | 2/2001 |
| WO | WO 01/24871 | 4/2001 |
| WO | WO 01/41671 | 6/2001 |
| WO | WO 01/49367 | 7/2001 |
| WO | WO 01/52931 | 7/2001 |
| WO | WO 01/66183 | 9/2001 |
| WO | WO 01/83019 | 11/2001 |
| WO | WO 01/91854 | 12/2001 |
| WO | WO 01/93950 | 12/2001 |
| WO | WO 01/93951 | 12/2001 |
| WO | WO 02/10791 | 2/2002 |
| WO | WO 02/23953 | 3/2002 |
| WO | WO 02/053093 | 7/2002 |
| WO | WO 02/082968 | 10/2002 |
| WO | WO 02/089655 | 11/2002 |
| WO | WO 03/020365 | 3/2003 |
| WO | WO 03/045493 | 6/2003 |
| WO | WO 2004/021858 | 3/2004 |
| WO | WO2004021858 | 3/2004 |
| WO | WO 2004/043280 | 5/2004 |
| WO | WO 2004/066903 | 8/2004 |
| WO | WO 2004/069330 | 8/2004 |
| WO | WO 2004/070396 | 8/2004 |
| WO | WO 2004/080533 | 9/2004 |
| WO | WO 2004/091361 | 10/2004 |
| WO | WO 2004/096337 | 11/2004 |
| WO | WO 2004/112563 | 12/2004 |
| WO | WO 2004/112883 | 12/2004 |
| WO | WO 2005/007232 | 1/2005 |
| WO | WO 2005/007237 | 1/2005 |
| WO | WO 2005/009288 | 2/2005 |
| WO | WO 2005/016181 | 2/2005 |
| WO | WO 2005/023081 | 3/2005 |
| WO | WO 2005/037152 | 4/2005 |
| WO | WO 2005/041749 | 5/2005 |
| WO | WO 2005/087310 | 9/2005 |
| WO | WO 2005/106333 | 11/2005 |
| WO | WO 2005/114369 | 12/2005 |
| WO | WO 2006/018851 | 2/2006 |
| WO | WO 2006/035446 | 4/2006 |
| WO | WO 2006/073671 | 7/2006 |

(56) References Cited

FOREIGN PATENT DOCUMENTS

| | | |
|---|---|---|
| WO | WO 2006/087712 | 8/2006 |
| WO | WO 2006/087717 | 8/2006 |
| WO | WO 2006/097934 | 9/2006 |
| WO | WO 2006/097935 | 9/2006 |
| WO | WO 2006/102626 | 9/2006 |
| WO | WO 2006/129321 | 9/2006 |
| WO | WO 2006/118790 | 11/2006 |
| WO | WO 2006/119467 | 11/2006 |
| WO | WO 2007/080595 | 7/2007 |
| WO | WO 2007/091255 | 8/2007 |
| WO | WO 2007/096877 | 8/2007 |
| WO | WO 2007/096878 | 8/2007 |
| WO | WO 2008/007368 | 1/2008 |
| WO | WO 2008/117296 | 10/2008 |
| WO | WO 2008/139463 | 11/2008 |
| WO | WO 2011/092710 | 8/2011 |
| ZA | 97/06341 | 2/1998 |

OTHER PUBLICATIONS

Shemerovskii KA, "Effect of feeding on the activity of duodenal smooth muscle in dogs", Biull Eksp Biol Med. Oct. 1978;86(10):394-7. (Abstract only).

U.S. Appl. No. 10/237,263.

Jaremko, et al., "Advances toward the implantable artificial pancreas for treatment of diabetes", Diabetes Care, 21(3), Mar. 1998.

Lamb F.S. et al., "Cyclosporine augments reactivity of isolated blood vessels", Life Sciences, 40, pp. 2571-2578, 1987.

Johansson B. et al., "Static and dynamic components in the vascular myogenic response to passive changes in length as revealed by electrical and mechanical recordings from the rat portal vein", Circulation Research, 36, pp. 76-83, 1975.

Zelcer E. et al., "Spontaneous electrical activity in pressurized small mesenteric arteries", Blood Vessels, 19, pp. 301-310, 1982.

Schobel H.P. et al., "Preeclampsia—a state of sympathetic overactivity", New England Journal of Medicine, 335, pp. 148-1485, 1996.

Rosenpire A.J. et al., "Pulsed DC Electric Fields Couple to Natural NAD(P)H Oscillations in HT-1080 Fibrosarcoma Cells", Journal of Cell Science, 114(Pt. 8), pp. 1515-1520, Apr. 2001.

Gomis A. et al., "Oscillatory patterns of electrical activity in mouse pancreatic islets of Langerhans recorded in vivo", Pflugers Archiv European Journal of Physiology, Abstract vol. 432(3), pp. 510-515, 1996.

Soria B. et al., "Cytosolic calcium oscillations and insulin release in pancreatic islets of Langerhans", Diabetes Metab., 24(1), pp. 37-40, Feb. 1998.

Magnus G. et al., "Model of Beta-cell mitochondrial calcium handling and electrical activity. II. Mitochondrial variables", American Journal of Physiology, 274(4 Pt 1): C1174-1184, Apr. 1998.

Gut R. et al., "High-precision EMG signal decomposition using communication techniques", IEEE transactions on signal processing, 48(9), pp. 2487-2494, Sep. 2000.

Nadal A. et al., "Homologous and heterologous asynchronicity between identified alpha-, beta-, and delta-cells within intact islets of Langerhans in the mouse", Journal of Physiology, 517(Pt. 1), pp. 85-93, May 1999.

M D Robertson, et al, "The influence of the colon on postprandial glucagons-like peptide 1 (7-36) amide concentration in man", Journal of Endocrinology (1999) 161, 25-31.

J Schirra, et al, "Mechanisms of the antidiabetic action of subcutaneous glucagons-like peptide-1 (7-36) amide in non-insulin dependent diabetes mellitus", Journal of Endocrinology (1998) 156, 177-186.

T Vilsboll and Associates, Research design and methods, Diabetes, vol. 50, Mar. 2001, pp. 610-613.

Jeannie F. Todd, et al, "Subcutaneous glucagons-like peptide-1 improves postprandial glycaemic control over 3-week period in patients with early type 2 diabetes", Clinical Science (1998) 95, 325-329.

Daniel J. Drucker, "Development of glucagon-like peptide-1-based pharmaceuticals as therapeutic agents for the treatment of diabetes", Current Pharmaceutical Design, 2001, 7, 1399-1412.

Meda et al., Quarterly J. Exper. Physiol. 69:719-735 (1984).

Eddiestone et al., J. Membrane Biol. 77:1-141 (1984).

Adeghate et al. "Effect of Electrical Field Stimulation on Insulin and Glucagon Secretion From the Pancreas of Normal and Diabetic Rats", Hormone and Metabolic Research, 33(5): 281-289, May 2001. Abstract.

Antoni et al. "Polarization Effects of Sinusoidal 50-Cycle Alternating Current on Membrane Potential of Mammalian Cardiac Fibres", Pflügers Archiv European Journal of Physiology, 314(4): 274-291, 1970. Abstract.

Bergsten et al. "Synchronous Oscillations of Cytoplasmic Ca2+ and Insulin Release in Glucose-Stimulated Pancreatic Islets", The Journal of Biological Chemistry, 269(12): 8749-8753, Mar. 25, 1994.

Borst et al."Coronary Artery Bypass Grafting Without Cardiopulomonary Bypass and Without Interuption of Native Coronary Flow Using a Novel Anastomosis Site Restraining Device (Octupus)", Journal of the American College of Cardiology, 27(6): 1356-1364, 1996.

Burfeind et al "The Effects of Mechanical Cardiac Stabilization on Left Ventricular Performance", Europeari Journal of Cardio-Thoracic Surgery, 14: 285-289, 1998.

Cazeau et al. "Multisite Pacing for End-Stage Heart Failure: Early Experience", Pacing and Clinical Electrophysiology, 19(11): 1748-1757, 1996, Abstract.

Devedeux et al."Uterine Electromyography: A Critical Review", American Journal of Obstetric Gynecology, 169(6): 1636-1653, 1993.

Dillion "Synchronized Repolarization After Defibrillation Shocks. A Possible Component of the Defibrillation Process Demonstration by Optical Recordings in Rabbit Heart", Circulation, 85(5): 1865-1878, 1992.

Erol-Yilmaz et al."Reversed Remodelling of Dilated Left Sided Cardiomyopathy After Upgrading from VVIR to VVIR Biventricular Pacing", Europace, 4: 445-449, 2002.

Fromer et al. "Ultrarapid Subthreshold Stimulation for Termination of Atriventricular Node Reentrant Tachycardia", Journal of the American College Cardiology, 20: 879-883, 1992.

Gilmour Jr. et al. "Dynamics of Circus Movement Re-Entry Across Canine Purkinje Fibre-Muscle Junctions", The Journal of Physiology, 476(3): 473-485, 1994.

Gold et al. "Evidence That Glucose 'Marks' Beta Cells Resulting in Preferential Release of Newly Synthesized Insulin", Science, 218(4567): 56-58, Oct. 1, 1982. Abstract.

Gomis et al. "Oscillatory Patterns of Electrical Activity in Mouse PancreaticIslets of Langerhans Recorded in Vivo", PflÜgers Archiv European Journal of Physiology, 432(3): 510-515, 1996.

Gussoni et al. "Dystrophin Expression in the MDX Mouse Restored by Stem Cell Transplantation", Nature, 401(6751): 390-394, 1999.

Hinke et al. "Dipeptidyl Peptidase IV (DPIV/CD26) Degradation of Glucagon. Characterization of Glucagon Degradation Products and DPIV-Resistant Analogs", The Journal of Biological Chemistry, 275(6): 3827-3834, Feb. 11, 2000.

Holst et al. "Nervous Control of Pancreatic Endocrine Secretion in Pigs. I. Insulin and Glucagon Responses to Electrical Stimulation of the Vagus Nerves", Acta Physiologica Scandinavica, 111(1): 1-7, Jan. 1981. Abstract.

Holst et al. "Nervous Control of Pancreatic Endocrine Secretion in Pigs. II. The Effect of Pharmacological Blocking Agents on the Response to Vagal Stimulation", Acta Physiologica Scandinavica, 111(1): 9-14, 1981. Abstract.

Horner et al. "Electrode for Recording Direction of Activation, Conduction Velocity and Monophasic Action Potential of Myocardium", American Journal of Physiology, 272(4): H1917-H1927, 1997. Abstract.

Jaremko et al. "Advances Towards the Implantable Artifical Pancreas for Treatment of Diabetes", Diabetes Care, 21(3): 444-450, 1998.

Knisley et al "Effect of Field Stimulation on Cellular Repolarization in Rabbit Myocardium. Implications for Reentry Induction", Circulation Research, 70(4): 707-715, Apr. 1992.

(56) References Cited

OTHER PUBLICATIONS

Kurose et al. "Glucagon, Insulin and Somatostatin Secretion in Response to Sympathetic Neural Activation in Streptozotocin—Induced Diabetic Rats. A Study With the Isolated Perfused Rat Pancreas In Vitro", Diabetologia, 35(11): 1035-1041, Nov. 1992. Abstract.
Lindström et al. "Intracellular Calcium Oscillations in A T-Cell Line After Exposure to Extremely-Low-Frequency Magnetic Fields with Variable Frequencies and Flux Densities", Bioelectromagnetics, 16(1): 41-47, 1995, Abstract.
Loginov "Accumulation of Calcium Ions in Myocardial Sarcoplasmic Reticulum of Restrained Rats Exposed to the . . . ", Aviakosm. Ekolog. Med., 26: 49-51, 1992.
Luiken et al. "Contraction-Induced Fatty Acid Translocase/CD36 Translocation in Rat Cardiac Myocytes is Mediated Through AMP-Activated Protein Kinase Signaling", Diabetes, 52: 1627-1634, 2003.
Magnus et al. "Model of β-Cell Mitochondrial Calcium Handling and Electrical Activity. II. Mitochondrial Variables", American Journal of Physiology, Cell Physiology, 274(43): C1174-C1184, 1998.
Misler et al. "Electrophysiology of Stimulus-Secretion Coupling in Human Beta-Cells", Diabetes, 41(10): 1221-1228, Oct. 1992. Abstract.
Nadal et al. "Homologous and Heterologous Asynchronicity Between Identified α-, β- and δ- Cells Within Intact Islets of Langerhans in the Mouse", Journal of Physiology, 517(Pt.1): 85-93, 1999.
Ohinata et al. "Proadrenomedullin N-Terminal 20 Peptide (PAMP) Elevates Blood Glucose Levels Via Bombesin Receptor in Mice", FEBS Letters, 473(2): 207-211, May 2000. Abstract.
Palti et al. "Islets of Langerhans Generate Wavelike Electric Activity Modulated by Glucose Concentration", Diabetes, 45(5): 595-601, May 1996. Abstract.
Patterson et al. "Therapeutic Angiogenesis: The New Electrophysiology?", Circulation, 99(20): 2614-2616, 1999.
Pokrovsky et al. "Physiology of Man", 1: 82-83, 94, 2: 42, 54.
Pørksen et al. "Section 6: Pulsatile and Phasic Insulin Release in Normal and Diabetic Man. Pulsatile Insulin Secretion: Detection, Regulation, and Role in Diabetes", Diabetes, 51(Suppl.1): S245-S254, Feb. 2002.
Rivera et al. "Regulation of Protein Secretion Through Controlled Aggregation in the Endoplasmic Reticulum", Science, 287(5454): 826-830, Feb. 4, 2000. Abstract.
Sakuma et al. "A Model Analysis of Aftereffects of High-Intensity DC Stimulation on Action Potential of Ventricular Muscle", IEEE Transactions on Biomedical Engineering, 45(2): 258-267, 1998, Abstract.
Schirra et al. "Mechanisms of the Antidiabetic Action of Subcutaneous Glucagon-Like Peptide-1 (17-36) Amide In Non-Insulin Dependent Diabetes Mellitus", Journal of Endocrinology Ltd., 156(1): 177-186, Jan. 1998. Abstract.
Schirra et al. "Exendin(9-39) Amide Is An Antagonist of Glucagon-Like Peptide-1(7-36) Amide in Humans", Journal of Clinical Investigation, 101(7): 1421-1430, Apr. 1998.
Serre et al. "Exendin-(9-39) Is An Inverse Agonist of the Murine Glucagon-Like Peptide-1 Receptor: Implications for Basal Intracellular Cyclic Adenosine 3',5'-Monophosphate Levels and β-Cells Glucose Competence", Endocrinology, 139(11): 4448-4454, 1998.
Shah et al. "Impact of Lack of Suppression of Glucagon on Glucose Tolerance in Humans", American Journal of Physiology, AJP—Endocrinology and Metabolism, 277(2 Pt.1): E283-E290, 1999.
Shmit et al. "Physiology of Man", Moscow Medicine, Mir, 1: 78, 1996.
Shuba et al. "Physiology of Vessel Smooth Muscles", Kiev Naukova Dumka, 142: 11-15, 142, 1988.
Soria et al. "Cytosolic Calcium Oscillations and Insulin Release in Pancreatic Islets of Langerhans", Diabetes & Metabolism, 24: 37-40, 1998.
Sweeny et al. "Countershock Strength-Duration Relationship for Myocardial Refractory Period Extension", Academic Emergency Medicine, 2(1): 57-62, 1995, Abstract.
Sweeny et al "Ventricular Refractory Period Extension Caused by Defibrillation Shocks", Circulation, 82(3): 965-972, 1990.
Swerdlow et al. "Cardiovascular Collapse Caused by Electrocardiographically Silent 60-Hz Intracardiac Leakage Current: Implications for Electrical Safety", Circulation, 99: 2559-2564, 1999.
Todd et al. "Subcutaneous Glucagon-Like Peptide I Improves Postprandial Glycaemic Control Over A 3-Week Period in Patients With Early Type 2 Diabetes", Clinical Science, 95: 325-329, 1998.
Valdeolmillos et al. "In Vivo Synchronous Membrane Potential Oscillations in Mouse Pancreatic Beta-Cells: Lack of Co-Ordination Between Islets", Journal of Physiology, 493(1): 9-18, 1996.
Van Riper et al. "Electrical Field Stimulation-Mediated Relaxation of A Rabbit Middle Cerebral Artery. Evidence of A Cholinergic Endothelium-Dependent Component", Circulation Research, 70(6): 1104-1112, Jun. 1992.
Wang et al. "Islet Amyloid Polypeptide Tonally Inhibits β-, α-, and δ-Cell Secretion in Isolated Rat Pancreatic Islets", American Journal of Physiology, AJP—Endocrinology and Metabolism, 276(1 Pt.1): E19-E24, 1999.
Xue et al. "Neural-Network-Based Adaptive Matched Filtering for QRS Detection", IEEE Transactions on Biomedical Engineering, 39(4): 317-329, 1992. Abstract.
Yonemura et al. "Amelioration of Diabetes Mellitus in Partially Depancreatized Rats by Poly(ADP-Ribose) Synthetase Inhibitors. Evidence of Islet B-Cell Regeneration", Diabetes, 33(4): 401-404, Apr. 1984. Abstract.
Zipes "Cardiac Electrophysiology—From Cell to Bedside", Saunders Co., 4th Ed., 1990.
Amended Request for Ex Parte Reexamination of US Patent No. 6,317,631 Dated Aug. 20, 2007 From the US Patent and Trademark Office Re.: U.S. Appl. No. 90/008,689.
Official Action Dated Dec. 5, 2008 From the US Patent and Trademark Office Re.: U.S. Appl. No. 11/550,560.
Request for Ex Parte Reexamination of US Patent No. 6,317,631—Amendment in Response to Official Action Dated Jun. 20, 2008, Filed Aug. 20, 2008 From the US Patent and Trademark Office Re.: U.S. Appl. No. 90/008,689.
Request for Ex Parte Reexamination of US Patent No. 6,317,631—IDS Dated Dec. 31, 2007 From the US Patent and Trademark Office Re.: U.S. Appl. No. 90/008,689.
Request for Ex Parte Reexamination of US Patent No. 6,317,631—IDS Dated Sep. 26, 2008 From the US Patent and Trademark Office Re.: U.S. Appl. No. 90/008,689.
Request for Ex Parte Reexamination of US Patent No. 6,236,887—Official Action and IDS Considered Dated Jun. 20, 2008 From the US Patent and Trademark Office Re.: U.S. Appl. No. 90/008,707.
Request for Ex Parte Reexamination of US Patent No. 6,298,268 Order Granting Request for Ex Parte Reexamination Dated Dec. 19, 2003, U.S. Appl. No. 90/006,788.
Request for Ex Parte Reexamination of Patent No. 6,363,279—IDS Submitted Dec. 31, 2007 From the US Patent and Trademark Office Re.: U.S. Appl. No. 90/008,688.
Request for Ex Parte Reexamination of Patent No. 6,363,279—Notice of Intent to Issue Reexamination Certificate Dated Mar. 18, 2009 From the US Patent and Trademark Office Re.: U.S. Appl. No. 90/008,688.
Request for Ex Parte Reexamination of Patent No. 6,363,279—Order Granting Request Dated Nov. 5, 2007 From the US Patent and Trademark Office Re.: U.S. Appl. No. 90/008,688.
Request for Ex Parte Reexamination of Patent No. 6,363,279—Official Action Dated Jun. 20, 2008 From the US Patent and Trademark Office Re.: U.S. Appl. No. 90/008,688.
Response Dated May 4, 2009 to Official Action of Nov. 3, 2008 From the US Patent and Trademark Office Re.: U.S. Appl. No. 10/116,201.
Office Action Dated Jul. 13, 2009 From the State Intellectual Property Office of the People's Republic of China Re.: Application No. 200480027083.3 and Its Translation Into English.
Official Action Dated Dec. 2, 2009 From the US Patent and Trademark Office Re.: U.S. Appl. No. 11/932,149.
Official Action Dated Oct. 6, 2009 From the US Patent and Trademark Office Re.: U.S. Appl. No. 11/550,560.
Official Action Dated Oct. 8, 2009 From the US Patent and Trademark Office Re.: U.S. Appl. No. 10/116,201.

(56) References Cited

OTHER PUBLICATIONS

Official Action Dated Sep. 14, 2009 From the US Patent and Trademark Office Re.: U.S. Appl. No. 11/931,889.
Official Action Dated Aug. 28, 2009 From the US Patent and Trademark Office Re.: U.S. Appl. No. 11/802,685.
Official Action Dated Aug. 28, 2009 From the US Patent and Trademark Office Re.: U.S. Appl. No. 11/932,064.
CN—Chinese Appln. No. 2004-80027283.3—Office Action issued by CPO dated Jul. 13, 2009.
Translation of Notification of Reason for Refusal Dated Feb. 1, 2011 From the Japanese Patent Office Re.: Application No. 2006-520981.
Translation of Notification of Reason for Refusal Dated Apr. 13, 2010 From the Japanese Patent Office Re.: Application No. 2006-520981.
Examination Report Dated Aug. 23, 2007 From the Government of India, Patent Office Re. Application No. 212/MUMNP/2006.
Second Examination Report Dated May 30, 2008 From the Government of India, Patent Office Re. Application No. 212/MUMNP/2006.
Office Action Dated May 26, 2010 From the State Intellectual Property Office of the People's Republic of China Re.: Application No. 200480027293.3 and Its Translation into English.
Supplementary European Search Report Dated Aug. 5, 2010 From the European Patent Office Re. Application No. 04745004.
Response Dated Jan. 6, 2010 to Official Action of Jun. 26, 2009 From the US Patent and Trademark Office Re.: U.S. Appl. No. 11/932,812.
Response Dated Jun. 8, 2010 to Official Action of Mar. 8, 2010 From the US Patent and Trademark Office Re.: U.S. Appl. No. 11/736,183.
Response Dated Dec. 10, 2009 to Official Action of Sep. 15, 2009 From the US Patent and Trademark Office Re.: U.S. Appl. No. 11/736,183.
Response Dated Apr. 12, 2010 to Official Action of Dec. 11, 2009 From the US Patent and Trademark Office Re.: U.S. Appl. No. 11/932,881.
Response Dated Jun. 20, 2010 to Official Action of Mar. 8, 2010 From the US Patent and Trademark Office Re.: U.S. Appl. No. 11/736,183.
Response Dated Apr. 23, 2010 to Official Action of Feb. 23, 2010 From the US Patent and Trademark Office Re.: U.S. Appl. No. 11/932,963.
Response Dated Nov. 29, 2010 to Official Action of Jun. 28, 2010 From the US Patent and Trademark Office Re.: U.S. Appl. No. 11/932,963.
Supplemental Response Dated Jun. 29, 2010 to Official Action of Jun. 22, 2010 From the US Patent and Trademark Office Re.: U.S. Appl. No. 11/736,183 and Response Dated Jun. 8, 2010 to Official Action of Mar. 8, 2010 From the US Patent and Trademark Office Re.: U.S. Appl. No. 11/736,183.
Response Dated May 10, 2011 to Notice of Allowance of Feb. 15, 2011 From the US Patent and Trademark Office Re.: U.S. Appl. No. 11/932,963.
JPO Office Action issued Feb. 1, 2011 for JP Appln. No. 2006-520981 (3 Pgs.).
Notice of Allowance Dated Aug. 31, 2012 From the US Patent and Trademark Office Re. U.S. Appl. No. 12/910,943.
Official Action Dated Aug. 27, 2012 From the US Patent and Trademark Office Re.: U.S. Appl. No. 11/919,491.
Corrected Notice of Allowability Dated Jul. 13, 2012 From the US Patent and Trademark Office Re. U.S. Appl. No. 11/933,168.
Notice of Allowability Dated Jul. 13, 2012 From the US Patent and Trademark Office Re. U.S. Appl. No. 11/933,168.
Notice of Allowance Dated Jul. 16, 2012 From the US Patent and Trademark Office Re. U.S. Appl. No. 11/931,889.
Notice of Allowance Dated Jul. 18, 2012 From the US Patent and Trademark Office Re.: U.S. Appl. No. 11/931,724.
Official Action Dated Jul. 3, 2012 From the US Patent and Trademark Office Re. U.S. Appl. No. 12/910,943.
U.S. Appl. No. 90/008,688, filed Jun. 15, 2007, Ben Haim.
U.S. Appl. No. 90/008,689, Ben Haim.
U.S. Appl. No. 90/008,707, filed Jun. 7, 2007, Ben Haim.
U.S. Appl. No. 95/000,032, Ben Haim.

Advisory Action Before the Filing of An Appeal Brief Dated Mar. 22, 2012 From the US Patent and Trademark Office Re. U.S. Appl. No. 11/886,154.
Communication Pursuant to Article 94(3) EPC Dated Mar. 2, 2009 From the European Patent Office Re.: Application No. 05853465.2.
Communication Pursuant to Article 94(3) EPC Dated Aug. 11, 2010 From the European Patent Office Re. Application No. 99931435.4.
Communication Pursuant to Article 94(3) EPC Dated Aug. 26, 2011 From the European Patent Office Re. Application No. 06759102.4.
Communication Pursuant to Article 94(3) EPC Dated Aug. 26, 2011 From the European Patent Office Re.: Application No. 05853465.2.
Communication Pursuant to Article 94(3) EPC Dated Jan. 29, 2009 From the European Patent Office Re.: Application No. 04106247.2.
Communication Pursuant to Article 96(2) EPC Dated Mar. 2, 2007 From the European Patent Office Re.: Application No. 97929478.2.
Communication to Pursuant to Article 94(3) EPC Dated Mar. 4, 2009 From the European Search Report Re.: Application No. 06759102.4.
Inter Partes Reexamination Communication of Patent US 6,330,476 Dated Sep. 4, 2007 From the US Patent and Trademark Office Re.: U.S. Appl. No. 95/000,032.
International Preliminary Report on Patentability Dated Nov. 15, 2007 From the International Bureau of WIPO Re.: Application No. PCT/US2006/017281.
International Preliminary Report on Patentability Dated Jun. 21, 2007 From the International Bureau of WIPO Re.: Application No. Jun. 21, 2007.
International Preliminary Report on Patentability Dated Sep. 27, 2007 From the International Bureau of WIPO Re.: Application No. PCT/IL2006/000345.
International Search Report and the Written Opinion Dated May 12, 2006 From the International Searching Authority Re.: Application No. PCT/US05/44557.
International Search Report and the Written Opinion Dated Oct. 16, 2006 From the International Searching Authority Re.: Application No. PCT/US06/17281.
Invitation Pursuant to Rule 62a(1) EPC and Rule 63(1) EPC Dated May 5, 2010 From the European Patent Office Re.: Application No. 04719312.3.
Notice of Allowance Dated Jan. 14, 2011 From the US Patent and Trademark Office Re.: U.S. Appl. No. 11/550,560.
Notice of Allowance Dated May 15, 2012 From the US Patent and Trademark Office Re.: U.S. Appl. No. 11/932,149.
Notice of Allowance Dated May 16, 2012 From the US Patent and Trademark Office Re. U.S. Appl. No. 11/886,154.
Notice of Allowance Dated Jun. 20, 2012 From the US Patent and Trademark Office Re. U.S. Appl. No. 11/933,168.
Notice of Allowance Dated Jun. 27, 2012 From the US Patent and Trademark Office Re.: U.S. Appl. No. 11/932,064.
Notice of Allowance Dated May 27, 2010 From the US Patent and Trademark Office Re.: U.S. Appl. No. 10/549,216.
Notice of Allowance Dated Dec. 28, 2010 From the US Patent and Trademark Office Re.: U.S. Appl. No. 11/932,064.
Notice of Non-Compliant Amendment Dated Jun. 1, 2011 From the US Patent and Trademark Office Re. U.S. Appl. No. 11/886,154.
Notice of Non-Compliant Amendment Dated Dec. 12, 2011 From the US Patent and Trademark Office Re. U.S. Appl. No. 11/792,811.
Notice of Non-Compliant Amendment Dated Jul. 15, 2011 From the US Patent and Trademark Office Re. U.S. Appl. No. 11/886,154.
Office Action Dated Jan. 8, 2010 From the State Intellectual Property Office (SIPO) of the People's Republic of China Re.: Application No. 200480012687.5 and Its Translation Into English.
Office Action Dated Oct. 12, 2004 From the Israeli Patent Office Re.: Application No. 128955.
Office Action Dated Dec. 15, 2008 From the State Intellectual Property Office (SIPO) of the People's Republic of China Re.: Application No. 200480012687.5 and Its Translation Into English.
Office Action Dated Jan. 18, 2012 From the State Intellectual Property Office (SIPO) of the People's Republic of China Re.: Application No. 200480012687.5 and Its Translation Into English.
Office Action Dated Nov. 25, 2010 From the State Intellectual Property Office (SIPO) of the People's Republic of China Re.: Application No. 200480012687.5 and Its Translation Into English.

(56) References Cited

OTHER PUBLICATIONS

Official Action Dated Aug. 1, 2007 From the US Patent and Trademark Office Re.: U.S. Appl. No. 90/008,312.
Official Action Dated Jun. 1, 2009 From the US Patent and Trademark Office Re.: U.S. Appl. No. 10/039,845.
Official Action Dated Jan. 3, 2011 From the US Patent and Trademark Office Re.: U.S. Appl. No. 11/932,149.
Official Action Dated Nov. 3, 2009 From the US Patent and Trademark Office Re.: U.S. Appl. No. 11/931,724.
Official Action Dated Feb. 4, 2010 From the US Patent and Trademark Office Re.: U.S. Appl. No. 10/039,845.
Official Action Dated Jan. 4, 2012 From the US Patent and Trademark Office Re. U.S. Appl. No. 11/673,812.
Official Action Dated Jan. 5, 2010 From the US Patent and Trademark Office Re.: U.S. Appl. No. 11/802,685.
Official Action Dated Nov. 5, 2009 From the US Patent and Trademark Office Re.: U.S. Appl. No. 10/549,216.
Official Action Dated Oct. 5, 2010 From the US Patent and Trademark Office Re.: U.S. Appl. No. 10/039,845.
Official Action Dated Jan. 6, 2010 From the US Patent and Trademark Office Re. U.S. Appl. No. 11/933,168.
Official Action Dated Jan. 6, 2011 From the US Patent and Trademark Office Re.: U.S. Appl. No. 11/931,724.
Official Action Dated Jan. 6, 2012 From the US Patent and Trademark Office Re. U.S. Appl. No. 11/933,168.
Official Action Dated Mar. 6, 2009 From the US Patent and Trademark Office Re.: U.S. Appl. No. 11/931,889.
Official Action Dated Mar. 6, 2009 From the US Patent and Trademark Office Re.: U.S. Appl. No. 11/932,064.
Official Action Dated Nov. 8, 2011 From the US Patent and Trademark Office Re.: U.S. Appl. No. 11/931,889.
Official Action Dated Aug. 9, 2011 From the US Patent and Trademark Office Re.: U.S. Appl. No. 11/932,149.
Official Action Dated Oct. 10, 2008 From the US Patent and Trademark Office Re. U.S. Appl. No. 09/980,748.
Official Action Dated Jun. 11, 2010 From the US Patent and Trademark Office Re.: U.S. Appl. No. 11/550,560.
Official Action Dated Jun. 11, 2010 From the US Patent and Trademark Office Re.: U.S. Appl. No. 11/932,064.
Official Action Dated Oct. 11, 2011 From the US Patent and Trademark Office Re.: U.S. Appl. No. 11/919,491.
Official Action Dated Sep. 11, 2009 From the US Patent and Trademark Office Re. U.S. Appl. No. 09/980,748.
Official Action Dated May 12, 2011 From the US Patent and Trademark Office Re.: U.S. Appl. No. 10/039,845.
Official Action Dated Sep. 12, 2008 From the US Patent and Trademark Office Re.: U.S. Appl. No. 10/039,845.
Official Action Dated Jan. 13, 2011 From the US Patent and Trademark Office Re.: U.S. Appl. No. 11/931,889.
Official Action Dated May 13, 2011 From the US Patent and Trademark Office Re. U.S. Appl. No. 11/933,168.
Official Action Dated Oct. 13, 2010 From the US Patent and Trademark Office Re.: U.S. Appl. No. 11/919,491.
Official Action Dated Apr. 14, 2011 From the US Patent and Trademark Office Re.: U.S. Appl. No. 11/932,149.
Official Action Dated Sep. 14, 2011 From the US Patent and Trademark Office Re. U.S. Appl. No. 11/886,154.
Official Action Dated Dec. 15, 2011 From the US Patent and Trademark Office Re. U.S. Appl. No. 12/910,943.
Official Action Dated Feb. 15, 2012 From the US Patent and Trademark Office Re. U.S. Appl. No. 11/802,685.
Official Action Dated Jul. 15, 2008 From the US Patent and Trademark Office Re.: U.S. Appl. No. 10/116,201.
Official Action Dated Feb. 17, 2012 From the US Patent and Trademark Office Re.: U.S. Appl. No. 11/932,149.
Official Action Dated Jun. 17, 2010 From the US Patent and Trademark Office Re.: U.S. Appl. No. 10/549,216.
Official Action Dated Jan. 18, 2012 From the US Patent and Trademark Office Re. U.S. Appl. No. 11/886,154.
Official Action Dated Jul. 18, 2007 From the US Patent and Trademark Office Re.: U.S. Appl. No. 10/039,845.
Official Action Dated Dec. 20, 2011 From the US Patent and Trademark Office Re.: U.S. Appl. No. 10/039,845.
Official Action Dated Feb. 21, 2012 From the US Patent and Trademark Office Re. U.S. Appl. No. 10/116,201.
Official Action Dated Jul. 21, 2010 From the US Patent and Trademark Office Re.: U.S. Appl. No. 11/802,685.
Official Action Dated May 21, 2007 From the US Patent and Trademark Office Re. U.S. Appl. No. 09/980,748.
Official Action Dated May 21, 2010 From the US Patent and Trademark Office Re. U.S. Appl. No. 10/116,201.
Official Action Dated Mar. 22, 2011 From the US Patent and Trademark Office Re. U.S. Appl. No. 11/886,154.
Official Action Dated Dec. 23, 2010 From the US Patent and Trademark Office Re. U.S. Appl. No. 09/980,748.
Official Action Dated Jun. 23, 2009 From the US Patent and Trademark Office Re.: U.S. Appl. No. 10/549,216.
Official Action Dated Jan. 24, 2011 From the US Patent and Trademark Office Re.: U.S. Appl. No. 11/919,491.
Official Action Dated Jun. 26, 2008 From the US Patent and Trademark Office Re.: U.S. Appl. No. 11/536,794.
Official Action Dated Apr. 28, 2011 From the US Patent and Trademark Office Re. U.S. Appl. No. 11/931,889.
Official Action Dated Apr. 28, 2011 From the US Patent and Trademark Office Re.: U.S. Appl. No. 11/931,889.
Official Action Dated Feb. 28, 2008 From the US Patent and Trademark Office Re. U.S. Appl. No. 09/980,748.
Official Action Dated Jun. 28, 2010 From the US Patent and Trademark Office Re.: U.S. Appl. No. 11/931,889.
Official Action Dated Apr. 29, 2009 From the US Patent and Trademark Office Re. U.S. Appl. No. 09/980,748.
Official Action Dated Sep. 29, 2010 From the US Patent and Trademark Office Re. U.S. Appl. No. 11/933,168.
Official Action Dated Apr. 30, 2010 From the US Patent and Trademark Office Re.: U.S. Appl. No. 11/931,724.
Official Action Dated Apr. 30, 2010 From the US Patent and Trademark Office Re.: U.S. Appl. No. 11/932,149.
Official Action Dated Aug. 30, 2006 From the US Patent and Trademark Office Re. U.S. Appl. No. 09/980,748.
Official Action Dated Aug. 31, 2007 From the US Patent and Trademark Office Re.: U.S. Appl. No. 11/536,794.
Official Action Dated Aug. 31, 2010 From the US Patent and Trademark Office Re.: U.S. Appl. No. 11/550,560.
Official Action Dated Mar. 31, 2011 From the US Patent and Trademark Office Re. U.S. Appl. No. 11/673,812.
Pre-Appeal Brief Request for Review Dated Aug. 9, 2011 From the US Patent and Trademark Office Re. U.S. Appl. No. 11/933,168.
Request for Ex Parte Reexamination of Patent No. 6,363,279 Dated Jun. 8, 2007 From the US Patent and Trademark Office Re.: U.S. Appl. No. 90/008,688.
Request for Ex Parte Reexamination of Patent No. 6,363,279, Response to Official Action Dated Jun. 20, 2008 Submitted Aug. 20, 2008 From the US Patent and Trademark Office Re.: U.S. Appl. No. 90/008,688.
Request for Ex Parte Reexamination of US Patent No. 6,236,887—IDS Submitted Oct. 17, 2007 From the US Patent and Trademark Office Re.: U.S. Appl. No. 90/008,707.
Request for Ex Parte Reexamination of US Patent No. 6,236,887—IDS Submitted Sep. 29, 2008 From the US Patent and Trademark Office Re.: U.S. Appl. No. 90/008,707.
Request for Ex Parte Reexamination of US Patent No. 6,236,887—Notice of Intent to Issue Ex Parte Examination Certificate Dated Mar. 19, 2009 From the US Patent and Trademark Office Re.: U.S. Appl. No. 90/008,707.
Request for Ex Pante Reexamination of US Patent No. 6,236,887—Official Action and IDS Considered Dated Jun. 20, 2008 From the US Patent and Trademark Office Re.: U.S. Appl. No. 90/008,707.
Request for Ex Parte Reexamination of US Patent No. 6,236,887—Official Action Granting Request for Ex Parte Examination Dated Aug. 17, 2007 From the US Patent and Trademark Office Re.: U.S. Appl. No. 90/008,707.

(56) References Cited

OTHER PUBLICATIONS

Request for Ex Parte Reexamination of US Patent No. 6,236,887 Dated Jun. 13, 2007 From the US Patent and Trademark Office Re.: U.S. Appl. No. 90/008,707.
Request for Ex Parte Reexamination of US Patent No. 6,298,268—Certificate of Reexamination Issued Mar. 7, 2006, U.S. Appl. No. 90/006,788.
Request for Ex Parte Reexamination of US Patent No. 6,298,268—IDS Considered Feb. 22, 2005, U.S. Appl. No. 90/006,788.
Request for Ex Parte Reexamination of US Patent No. 6,298,268—Notice of Intent to Issue Certificate of Reexamination Dated Mar. 29, 2005, U.S. Appl. No. 90/006,788.
Request for Ex Parte Reexamination of US Patent No. 6,298,268 Dated Oct. 10, 2003, U.S. Appl. No. 90/006,788.
Request for Ex Parte Reexamination of US Patent. No. 6,298,268 Order Granting Request for Ex Parte Reexamination Dated Dec. 19, 2003, U.S. Appl. No. 90/006,788.
Request for Ex Parte Reexamination of US Patent No. 6,317,631—Notice of Intent to Issue Certificate of Reexamination Dated Mar. 18, 2009 From the US Patent and Trademark Office Re.: U.S. Appl. No. 90/008,689.
Request for Ex Parte Reexamination of US Patent No. 6,317,631—Official Action Dated Jun. 20, 2008, U.S. Appl. No. 90/008,689.
Request for Ex Parte Reexamination of US Patent No. 6,317,631—Order Granting Reexamination Dated Nov. 5, 2007, U.S. Appl. No. 90/008,689.
Request for Ex Parte Reexamination of US Patent No. 6,317,631—IDS Dated Jun. 8, 2007, U.S. Appl. No. 90/008,689.
Request for Ex Parte Reexamination of US Patent No. 6,330,476—IDS Dated May 31, 2006.
Request for Ex Parte Reexamination of US Patent No. 6,330,476—Comments by 3rd Party Requestor, Response Thereto and Official Action Issued Jul. 16, 2008, U.S. Appl. No. 95/000,032.
Request for Ex Parte Reexamination of US Patent No. 6,330,476—Communication of Right to Appeal dated Jul. 16, 2008, U.S. Appl. No. 95/000,032.
Request for Ex Parte Reexamination of US Patent No. 6,330,476—IDS Filed May 4, 2007, U.S. Appl. No. 95/000,032.
Request for Ex Parte Reexamination of US Patent No. 6,330,476—Official Action by USPTO Issued Mar. 23, 2004, U.S. Appl. No. 95/000,032.
Request for Ex Parte Reexamination of US Patent No. 6,330,476—Order Granting Request for Reexamination Dated Mar. 23, 2004 From the US Patent and Trademark Office Re.: U.S. Appl. No. 95/000,032.
Request for Ex Parte Reexamination of US Patent No. 6,330,476 Dated Dec. 31, 2003 From the US Patent and Trademark Office Re.: U.S. Appl. No. 95/000,032.
Request for Ex Parte Reexamination of US Patent No. 6,463,324—Amendment in Response to Official Action Dated Aug. 1, 2007 Filed Oct. 1, 2007 From the US Patent and Trademark Office Re.: U.S. Appl. No. 90/008,312.
Request for Ex Parte Reexamination of US Patent No. 6,463,324—Certificate of Reexamination Dated Apr. 29, 2008 From the US Patent and Trademark Office Re.: U.S. Appl. No. 90/008,312.
Request for Ex Parte Reexamination of US Patent No. 6,463,324—Official Action—Notice of Intent to Reexamine Dated Jan. 24, 2008 From the US Patent and Trademark Office Re.: U.S. Appl. No. 90/008,312.
Request for Ex Parte Reexamination of US Patent No. 6,463,324—Official Action Dated Aug. 1, 2007 From the US Patent and Trademark Office Re.: U.S. Appl. No. 90/008,312.
Request for Ex Parte Reexamination of US Patent No. 6,463,324—Official Action, Interview Summary and References Considered Dated Nov. 6, 2007 From the US Patent and Trademark Office Re.: U.S. Appl. No. 90/008,312.
Request for Ex Parte Reexamination of US Patent No. 6,463,324 Dated Nov. 1, 2006 From the US Patent and Trademark Office Re.: U.S. Appl. No. 90/008,312.

Summons to Attend Oral Proceedings Pursuant to Rule 115(1) EPC Dated Dec. 22, 2008 From the European Patent Office Re.: Application No. 97929480.8.
Supplemental Response Dated Apr. 18, 2011 to Response of Apr. 10, 2011 to Official Action of Jan. 6, 2011 From the US Patent and Trademark Office Re.: U.S. Appl. No. 11/931,724.
Supplementary European Search Report and the European Search Opinion Dated Nov. 28, 2008 From the European Patent Office Re.: Application No. 006759102.4.
Supplementary European Search Report and the European Search Opinion Dated Nov. 28, 2008 From the European Patent Office Re.: Application No. 05853465.2.
Supplementary Partial European Search Report Dated Nov. 4, 2010 From the European Patent Office Re. Application No. 04719312.3.
Translation of Notice of Reasons for Rejection Dated Jul. 18, 2006 From the Japanese Patent Office Re.: Application No. 09-529637.
Translation of Notice of Reasons for Rejection Dated Apr. 27, 2010 From the Japanese Patent Office Re.: Application No. 2007-206282.
Translation of Office Action Dated Aug. 3, 2011 From the State Intellectual Property Office (SIPO) of the People's Republic of China Re.: Application No. 200480012687.5.
Translation of Office Action Dated Apr. 20, 2011 From the State Intellectual Property Office (SIPO) of the People's Republic of China Re.: Application No. 200480012687.5.
USPTO Public Print Out of Interference File Content of Interference Dated Apr. 4, 2011 From the US Patent and Trademark Office Re. Interference No. 105,765.
USPTO Public Print Out of Interference File Content of Interference Dated Apr. 4, 2011 From the US Patent and Trademark Office Re. Interference No. 105,768.
Blank et al. "Initial Interactions in Electromagnetic Field-Induced Biosynthesis", Journal of Cellular Physiology, 199: 359-363, 2004.
Gardner "Natriuretic Peptides: Markers or Modulators of Cardiac Hypertrophy?", Trends in Endocrinology and Metabolism, 14(9): 411-416, Nov. 2003.
Gilmour Jr. et al. "Overdrive Suppression of Conduction at the Canine Purkinje-Muscle Junction", Circulation, 76(6): 1388-1396, 1987.
Hammond et al. "Motor Innervation of the Cricopharyngeus Muscle by the Recurrent Lanryngeal Nerve", Journal of Applied Physiology, JAP, 83: 89-94, 1997.
Highfill et al. "Large-Scale Production of Murine Bone Marrow Cells in an Airlift Packed Bed Bioreactor", Biotechnology and Bioengineering, 50(5): 514-520, 1996.
Meurer et al. "Properties of Native and in Vitro Glycosylated Forms of the Glucogan-Like Peptide-1 Receptor Antagonist Exendin(9-39)", Metabolism: Clinical and Experimental, 48(6): 716-724, Jun. 1999. Abstract.
San Mauro et al. "Nerves of the Heart: A Comprehensive Review With A Clinical Point of View", Neuroanatomy, 8: 28-31, 2009.
Sukhorukov et al. "The Effect of Electrical Deformation Forces on the Electropermeabilization of Erythrocyte Membranes in Low-and High-Conductivity Media", The Journal of Membrane Biology, 163(3): 235-245, 1998. Abstract.
Sutton et al. "The Foundation of Cardiac Pacing, Part I: An Illustrated Practical Guide to Basic Pacing", The Bakken Research Center Series, Chap.4: 50-59, 1991.
Sutton et al. "What Is A Pacemaker?", The Foundations of Cardiac Pacing, Part I: An Illustrated Practical Guide to Basic Pacing, Chap. 4.5: 73-74, 1991.
Webster "Electrodes, Leads, and Biocompatibility", Design of Cardiac Pacemakers, IEEE Press, p. 141-144, 1995.
Wright et al. "Structure of Fab hGR-2 F6, A Competitive Antagonist of the Glucagon Receptor", Acta Crystallographica, Section D, Biological Crystallography, 56(Pt.5): 573-580, May 2000. Abstract.
Notice of Allowance Dated Jul. 11, 2012 From the US Patent and Trademark Office Re. U.S. Appl. No. 11/550,560.
International Search Report and The Written Opinion Dated Sep. 2, 2011 From the International Searching Authority Re. Application No. PCT/IL 11/00116.
Office Action Dated May 10, 2012 in U.S. Appl. No. 10/599,015.
Official Action Dated Jun. 12, 2012 From the US Patent and Trademark Office Re. U.S. Appl. No. 11/573,722.

(56) References Cited

OTHER PUBLICATIONS

Official Action Dated Aug. 30, 2012 From the US Patent and Trademark Office Re. U.S. Appl. No. 12/160,616.
Communication Pursuant to Article 94(3) EPC Dated Oct. 10, 2011 From the European Patent Office Re. Application No. 07110023.4.
Communication Pursuant to Article 94(3) EPC Dated Jan. 27, 2010 From the European Patent Office Re. Application No. 07110023.4.
Communication Pursuant to Article 94(3) EPC Dated Jan. 28, 2009 From the European Patent Office Re.: Application No. 03794043.4.
Communication Pursuant to Article 94(3) EPC Dated Aug. 30, 2012 From the European Patent Office Re. Application No. 07110023.4.
Communication Pursuant to Rules 70(2) and 70a(2) EPC Dated Oct. 12, 2012 From the European Patent Office Re.: Application No. 06711186.4.
European Search Report and the European Search Opinion Dated Jul. 27, 2007 From the European Patent Office Re. Application No. 07110023.4.
Examination Report Dated Mar. 13, 2012 From the Government of India, Patent Office, Intellectual Property Building Re. Application No. 2988/CHENP/2007.
Examination Report Dated May 18, 2011 From the Government of India, Patent Office, Intellectual Property Building Re. Application No. 2988/CHENP/2007.
Examination Report Dated Jun. 26, 2009 From the Government of India, Patent Office Re.: Application No. 1161/CHENP/2006.
Examination Report Dated Nov. 30, 2010 From the Government of India, Patent Office Re. Application No. 212/MUMNP/2006.
International Preliminary Report on Patentability Dated Dec. 1, 2004 From the International Preliminary Examining Authority Re.: Application No. PCT/IL03/00736.
International Preliminary Report on Patentability Dated Aug. 30, 2007 From the International Bureau of WIPO Re.: Application No. PCT/IL2006/000204.
International Search Report and the Written Opinion Dated Sep. 29, 2006 From the International Searching Authority Re.: Application No. PCT/IL06/00204.
International Search Report Dated Sep. 13, 2004 From the International Searching Authority Re.: Application No. PCT/IL03/00736.
Notice of Allowance Dated Sep. 7, 2006 From the US Patent and Trademark Office Re.: U.S. Appl. No. 10/804,560.
Notice of Allowance Dated May 11, 2011 From the US Patent and Trademark Office Re.: U.S. Appl. No. 10/237,263.
Notice of Allowance Dated Nov. 29, 2010 From the US Patent and Trademark Office Re. U.S. Appl. No. 10/237,263.
Notice of Allowance Dated Aug. 31, 2012 From the US Patent and Trademark Office Re. U.S. Appl. No. 11/318,845.
Notification of Reasons of Rejection Dated Sep. 29, 2008 From the Japanese Patent Office Re.: Application No. 2004-534013 and Its Translation Into English.
Office Action Dated Dec. 4, 2009 From the State Intellectual Property Office of the People's Republic of China Re.: Application No. 03824661.9 and Its Translation Into English.
Office Action Dated Nov. 7, 2008 From the State Intellectual Property Office of the People's Republic of China Re.: Application No. 03824661.9 and Its Translation Into English.
Office Action Dated May 8, 2009 From the State Intellectual Property Office of the People's Republic of China Re.: Application No. 03824661.9 and Its Translation Into English.
Office Action Dated Apr. 13, 2010 From the State Intellectual Property Office of the People's Republic of China Re. Application No. 200480027293.3 and Its Translation into English.
Official Action Dated Nov. 1, 2011 From the US Patent and Trademark Office Re.: U.S. Appl. No. 10/804,560.
Official Action Dated Oct. 1, 2009 From the US Patent and Trademark Office Re.: U.S. Appl. No. 10/237,263.
Official Action Dated Dec. 3, 2009 From the US Patent and Trademark Office Re.: U.S. Appl. No. 11/318,845.
Official Action Dated Sep. 3, 2009 From the US Patent and Trademark Office Re.: U.S. Appl. No. 10/804,560.
Official Action Dated Dec. 4, 2009 From the US Patent and Trademark Office Re.: U.S. Appl. No. 11/884,389.
Official Action Dated Jan. 4, 2011 From the US Patent and Trademark Office Re.: U.S. Appl. No. 11/318,845.
Official Action Dated May 5, 2010 From the US Patent and Trademark Office Re.: U.S. Appl. No. 11/884,389.
Official Action Dated Dec. 6, 2011 From the US Patent and Trademark Office Re.: U.S. Appl. No. 11/318,845.
Official Action Dated Aug. 8, 2007 From the US Patent and Trademark Office Re.: U.S. Appl. No. 10/804,560.
Official Action Dated Dec. 8, 2008 From the US Patent and Trademark Office Re.: U.S. Appl. No. 10/804,560.
Official Action Dated Jun. 8, 2011 From the US Patent and Trademark Office Re. U.S. Appl. No. 11/566,775.
Official Action Dated Oct. 8, 2009 From the US Patent and Trademark Office Re. U.S. Appl. No. 11/566,775.
Official Action Dated Dec. 9, 2010 From the US Patent and Trademark Office Re. U.S. Appl. No. 11/566,775.
Official Action Dated Jul. 9, 2007 From the US Patent and Trademark Office Re.: U.S. Appl. No. 10/237,263.
Official Action Dated Mar. 10, 2011 From the US Patent and Trademark Office Re.: U.S. Appl. No. 11/884,389.
Official Action Dated May 11, 2011 From the US Patent and Trademark Office Re.: U.S. Appl. No. 10/804,560.
Official Action Dated Sep. 11, 2008 From the US Patent and Trademark Office Re.: U.S. Appl. No. 10/237,263.
Official Action Dated Oct. 13, 2010 From the US Patent and Trademark Office Re.: U.S. Appl. No. 10/237,263.
Official Action Dated Sep. 13, 2007 From the US Patent and Trademark Office Re.: U.S. Appl. No. 10/237,263.
Official Action Dated Dec. 14, 2010 From the US Patent and Trademark Office Re.: U.S. Appl. No. 11/884,389.
Official Action Dated Jul. 14, 2008 From the US Patent and Trademark Office Re.: U.S. Appl. No. 10/526,708.
Official Action Dated Dec. 15, 2010 From the US Patent and Trademark Office Re.: U.S. Appl. No. 10/804,560.
Official Action Dated Apr. 16, 2010 From the US Patent and Trademark Office Re. U.S. Appl. No. 11/566,775.
Official Action Dated Apr. 16, 2010 From the US Patent and Trademark Office Re.: U.S. Appl. No. 11/566,775.
Official Action Dated Apr. 18, 2007 From the US Patent and Trademark Office Re.: U.S. Appl. No. 10/804,560.
Official Action Dated Aug. 18, 2009 From the US Patent and Trademark Office Re.: U.S. Appl. No. 10/570,576.
Official Action Dated Jul. 19, 2007 From the US Patent and Trademark Office Re.: U.S. Appl. No. 10/526,708.
Official Action Dated Jun. 19, 2008 From the US Patent and Trademark Office Re.: U.S. Appl. No. 10/237,263.
Official Action Dated Jan. 21, 2009 From the US Patent and Trademark Office Re.: U.S. Appl. No. 10/570,576.
Official Action Dated Dec. 24, 2008 From the US Patent and Trademark Office Re.: U.S. Appl. No. 10/237,263.
Official Action Dated Feb. 24, 2009 From the US Patent and Trademark Office Re.: U.S. Appl. No. 11/318,845.
Official Action Dated Mar. 25, 2010 From the US Patent and Trademark Office Re.: U.S. Appl. No. 10/804,560.
Official Action Dated Sep. 25, 2009 From the US Patent and Trademark Office Re.: U.S. Appl. No. 10/526,708.
Official Action Dated May 26, 2010 From the US Patent and Trademark Office Re.: U.S. Appl. No. 11/318,845.
Official Action Dated Apr. 27, 2010 From the US Patent and Trademark Office Re.: U.S. Appl. No. 10/570,576.
Official Action Dated Mar. 27, 2008 From the US Patent and Trademark Office Re.: U.S. Appl. No. 10/804,560.
Official Action Dated Sep. 27, 2010 From the US Patent and Trademark Office Re.: U.S. Appl. No. 10/804,560.
Official Action Dated Oct. 30, 2012 From the US Patent and Trademark Office Re. U.S. Appl. No. 12/160,616.
Official Action Dated Jul. 31, 2008 From the US Patent and Trademark Office Re.: U.S. Appl. No. 11/318,845.
Official Action Dated Mar. 31, 2010 From the US Patent and Trademark Office Re.: U.S. Appl. No. 10/237,263.

(56) References Cited

OTHER PUBLICATIONS

Response Dated Aug. 1, 2010 to Notification of Reasons of Rejection of Apr. 12, 2010 From the Japanese Patent Office Re.: Application No. 2006-525265.
Response Dated Aug. 2, 2010 to Official Action of Mar. 31, 2010 From the US Patent and Trademark Office Re.: U.S. Appl. No. 10/237,263.
Response Dated Mar. 3, 2010 to Official Action of Sep. 3, 2009 From the US Patent and Trademark Office Re.: U.S. Appl. No. 10/804,560.
Response Dated May 3, 2010 to Official Action of Dec. 3, 2009 From the US Patent and Trademark Office Re.: U.S. Appl. No. 11/318,845.
Response Dated Feb. 4, 2010 to Official Action of Dec. 4, 2009 From the US Patent and Trademark Office Re.: U.S. Appl. No. 11/884,389.
Response Dated Jan. 5, 2010 to Official Action of Oct. 8, 2009 From the US Patent and Trademark Office Re. U.S. Appl. No. 11/566,775.
Response Dated Oct. 5, 2010 to Official Action of May 5, 2010 From the US Patent and Trademark Office Re.: U.S. Appl. No. 11/884,389.
Response Dated Jun. 6, 2011 to Official Action of Jan. 4, 2011 From the US Patent and Trademark Office Re.: U.S. Appl. No. 11/318,845.
Response Dated May 7, 2007 to Examination Report of Mar. 2, 2007 From the Government of India, Patent Office Re.: Application No. 533/CHENP/2005.
Response Dated Feb. 8, 2010 to Official Action Dated Oct. 1, 2009 From the US Patent and Trademark Office Re.: U.S. Appl. No. 10/237,263.
Response Dated Oct. 10, 2011 to Official Action Dated May 11, 2011 From the US Patent and Trademark Office Re.: U.S. Appl. No. 10/804,560.
Response Dated Dec. 12, 2011 to Communication Pursuant to Article 94(3) EPC of Oct. 10, 2011 From the European Patent Office Re. Application No. 07110023.4.
Response Dated May 16, 2011 to Official Action of Dec. 14, 2010 From the US Patent and Trademark Office Re.: U.S. Appl. No. 11/884,389.
Response Dated Feb. 18, 2010 to Official Action of Aug. 18, 2009 From the US Patent and Trademark Office Re.: U.S. Appl. No. 10/570,576.
Response Dated Aug. 24, 2010 to the Supplementary European Search Report of Jun. 7, 2010 From the European Patent Office Re. Application No. 04770468.9.
Response Dated Feb. 24, 2011 to Notice of Allowance of Nov. 29, 2010 From the US Patent and Trademark Office Re. U.S. Appl. No. 10/237,263.
Response Dated Jan. 25, 2007 to Examination Report of Jul. 7, 2006 From the Government of India, Patent Office Re.: Application No. 533/CHENP/2005.
Response Dated Mar. 25, 2010 to Official Action of Sep. 25, 2009 From the US Patent and Trademark Office Re.: U.S. Appl. No. 10/526,708.
Response Dated Aug. 26, 2010 to Official Action of May 26, 2010 From the US Patent and Trademark Office Re.: U.S. Appl. No. 11/318,845.
Response Dated Aug. 26, 2011 to the Summons to Oral Proceedings of Jul. 4, 2011 From the European Patent Office Re.: Application No. 03794043.4.
Response Dated Jul. 26, 2010 to Official Action of Mar. 25, 2010 From the US Patent and Trademark Office Re.: U.S. Appl. No. 10/804,560.
Response Dated Jan. 27, 2011 to Official Action of Sep. 27, 2010 From the US Patent and Trademark Office Re.: U.S. Appl. No. 10/804,560.
Response Dated Jul. 27, 2010 to Communication Pursuant to Article 94(3) EPC of Jan. 27, 2010 From the European Patent Office Re. Application No. 07110023.4.
Response Dated Sep. 27, 2010 to Official Action of Apr. 27, 2010 From the US Patent and Trademark Office Re.: U.S. Appl. No. 10/570,576.
Response Dated Aug. 28, 2011 to Summons to Attend Oral Proceedings Pursuant to Rule 115(1) EPC of Jul. 4, 2011 From the European Patent Office Re.: Application No. 03794043.4.

Summons to Attend Oral Proceedings Pursuant to Rule 115(1) EPC Dated Jul. 4, 2011 From the European Patent Office Re.: Application No. 03794043.4.
Supplemental Response Dated Mar. 28, 2010 After an Interview of Mar. 4, 2010 From the US Patent and Trademark Office Re. U.S. Appl. No. 10/237,263.
Supplementary European Search Report and the European Search Opinion Dated Sep. 25, 2012 From the European Patent Office Re.: Application No. 06711186.4.
Supplementary European Search Report Dated Jun. 7, 2010 From the European Patent Office Re. Application No. 04770468.9.
Supplementary European Search Report Dated Jan. 12, 2011 From the European Patent Office Re. Application No. 05718889.8.
Supplementary Notice of Allowability Dated Nov. 22, 2006 From the US Patent and Trademark Office Re.: U.S. Appl. No. 10/804,560.
Translation of Decision of Rejection Dated Apr. 22, 2009 From the Japanese Patent Office Re.: Application No. 2004-534013.
Translation of Notification of Reasons of Rejection Dated Apr. 12, 2010 From the Japanese Patent Office Re.: Application No. 2006-525265.
Translation of Office Action Dated Sep. 12, 2008 From the State intellectual Property Office of the People's Republic of China Re.: Application No. 200480032636.9.
Antman et al. "Treatment of 150 Cases of Life-Threatening Digitalis Intoxication With Digoxin-Specific Fab Antibody Fragments", Circulation, 81(6): 1744-1752, 1990.
Antoni et al. "Polarization Effects of Sinusoidal 50-Cycle Alternating Current on Membrane Potential of Mammalian Cardiac Fibres", Pflueger's Archiv European Journal of Physiology, 314(4): 274-291, 1970. Abstract.
Bakker et al. "Beneficial Effects of Biventricular Pacing of Congestive Heart Failure", Pace, 17(Part II): 318, 1994.
Bargheer et al. "Prolongation of Monophasic Action Potential Duration and the Refractory Period in the Human Heart by Tedisamil, A New Potassium-Blocking Agent", Journal European Heart, 15(10): 1409-1414, 1994, Abstract.
Bers "Excitation Contraction Coupllng and Cardiac Contractile Force", Internal Medicine, 237(2): 17, 1991, Abstract.
Borst et al. "Coronary Artery Bypass Grafting Without Cardiopulmonary Bypass and Without Interuption of Native Coronary Flow Using A Novel Anastomosis Site Restraining Device (Octupus)", Journal of the American College of Cardiology, 27(6): 1356-1364, 1996. Abstract only!
Bouaziz et al. "Direct Electrical Stimulation of Insulin Secretion by Intact Murine Islets of Langerhans Through the Culture Support", Electromagnetic Biology and Medicine, 17(2): 171-184, 1998. Abstract.
Bronzino "Biomedical Engineering Handbook", IEEE Press/CRC Press, Chap. 82.5: 1288, 1995.
Cano et al. "Dose-Dependent Reversal of Dixogin-Inhibited Activity of An In-Vitro Na+K+ATPase Model by Digoxin-Specific Antibody", Toxicology Letters, 85(2): 107-1011, 1996.
Cazeau et al. "Multisite Pacing for End-Stage Heart Failure: Early Experience", Pacing and Clinical Electrophysiology, 19(11/Pt.2): 1748-1757, 1996. Abstract.
Cheng et al. "Calcium Sparks: Elementary Events Underlying Excitation-Contraction Coupling in Heart Muscle", Science, 262(5134): 740-744, 1993. Abstract.
Cooper "Postextrasystolic Potention. Do We Really Know What It Means and How to Use It?", Circulation, 88: 2962-2971, 1993.
Coulton et al. "Magnetic Fields and Intracellular Calcium; Effects on Lymphocytes Exposed to Conditions for 'Cyclotron Resonance'", Phys. Med. Biol., 38: 347-360, 1993, Abstract.
Dillion "Optial Recordings in the Rabbit Heart Show That Defibrillation Strength Shocks Prolong the Duration of Depolarization and the Refractory Period", Circulation Research, 69: 842-856, 1991.
Dillon "Synchronized Repolarization After Defibrillation Shocks. A Possible Component of the Defibrillation Process Demonstration by Optical Recordings in Rabbit Heart", Circulation, 85(5): 1865-1878, 1992.
Fain et al. "Improved Internal Defibrillation Efficacy With a Biphasic Waveform", American Heart Journal, 117(2): 358-364, 1989, Abstract.

(56) References Cited

OTHER PUBLICATIONS

Fleg et al. "Impact of Age on the Cardiovasvular Response to Dynamic Upright Exercise in Healthy Men and Women", Journal of Applied Physiologyl, 78: 890-900, 1995, Abstract.

Fleischhauer et al. "Electrical Resistances of Interstitial and Microvascular Space as Determinants of the Extracellular Electrical Field and Velocity of Propagation in Ventricular Myocardium", Circulation, 92: 587-594, 1995.

Foster et al. "Acute Hemodynamic Effects of Atrio—Biventricular Padng in Humans", The Society of Thoracic Surgeons, 59: 294-300, 1995, Abstract.

Franz "Bridging the Gap Between Basic Clinical Electrophysiology: What Can Be Learned From Monophasic Action Potential Recordings?", Journal Cardiovasc Electrophysiology, 5(8): 699-710, 1994, Abstract.

Franz "Method and Theory of Monophasic Action Potential Recording", Progress in Cardiovascular Diseases, 33(6): 347-368, 1991. Abstract.

Fu et al. "System Identification of Electrically Coupled Smooth Music Cells: The Passive Electrically Coupled Smooth Muscle Cells: The Passive Electrical Properties", IEEE Transactions on Biomedical Engineering, 38(11): 1130-1140, 1991.

Gill et al. "Refractory Period Extension During Ventricular Pacing at Fibrillatory Pacing Rates", Pacing and Clinical Elctrophysiology, 20(3): 647-653, 1997, Abstract.

Ham et al. "Classification of Cardiac Arrhythmias Using Fuzzy Artmap", IEEE Transactions on Biomedical Engineering, 43(4): 425-429, 1996, Abstract.

Hoffman et al. "Effects of Postextrasystolic Potentiation on Normal and Failing Hearts", Bulletin of the New York Academy of Medicine, 41(5): 498-534, 1965.

Josephson "Clinical Cardiac Electrophysiology: Techniques and Interpertations", Lea & Febiger, 2nd Ed., 2 P., 1991.

King et al. "The Inotropic Action of Paired Pulse Stimulation in the Normal and Failing Heart: An Experimental Study", Cardiovascular Research, 2: 122-129, 1968.

Knisley et al. "Effect of Field Stimulation on Cellular Repolarization in Rabbit Myocardium. Implications for Reentry Induction", Circulation Research, 70(4): 707-715, Apr. 1992.

Knisley et al. "Prolongation and Shortening of Action Potentials by Electrical Shocks in Frog Ventricular Muscle", American Journal of Physiology, 266(6): H2348-H2358, 1994, Abstract.

Koller et al. "Relation Between Repolarization and Refractoriness During Programmed Electrical Stimulation in the Human Right Ventricle", Circulation, 91(9): 2378-2384, 1995, Abstract.

Langberg et al. "Identification of Ventricular Tachycardia With Use of the Morphology of the Endocardial Electrogram", Circulation, 77(6): 1363-1369, 1988.

Lindstroem et al. "Intracellular Calcium Oscillations in A T-Cell Line After Exposure to Extremely-Low-Frequency Magnetic Fields With Variable Frequencies and Flux Densities", Bioelectromagnetics, 16(1): 41-47, 1995. Abstract.

Loginov et al. "Effects of an Impulse Electromagnetic Field on Calcium Ion Accumulation in the Sarcoplasmic . . . ", Kosm. Biol. Aviakosm. Med., 15: 51-53, 1991.

Lubart et al. "Effect of Light on Calcium Transport in Bull Sperm Cells", Journal of Photochemistry and Photobiology B, Biology, 15(4): 337-341, Sep. 15, 1992. Abstract.

Matheny et al. "Vagus Nerve Stimulation as A Method to Temporarily Slow or Arrest the Heart", Annals of Thoracic Surgery, 63(6): S28-29, 1997, Abstract.

McVeigh et al. "Noninvasive Measurement of Transmural Gradients in Myocardial Strain With MR Imaging", Radiology, 180(3): 677, 679-684, 1991.

Mercando et al. "Automated Detection of Tachycardias by Antitachycardia Devices", Cardiac Electrophysiology: From Cell to Bedside, Chap.100: 943-948, 2004.

Moran et al. "Digoxin-Specific Fab Fragments Impair Renal Function in the Rat", Journal of Pharmacy and Pharmacology, 46(10): 854-856, 1994, Abstract.

Morse et al. "A Guide to Cardiac Pacemakers, Defibrillators and Related Products", Droege Computing Services, Inc., vol. I, Nov. 19, 1996.

Nannini et al. "Muscle Recruitment With Intrafascicular Electrodes", IEEE Transactions on Biomedical Engineering, 38: 769-776, 1991, Abstract.

Paul et al. "Automatic Recognition of Ventricular Arrhythmias Using Temporal Electrogram Analysis", PACE, 14: 1265-1273, 1991.

Pumir et al. "Control of Rotating Waves in Cardiac Muscle: Analysis of the Effect of Electric Fields", Proceedings of the Royal Society B: Biological Sciences, 257(1349): 129-134, 1994. Abstract.

Ranjan et al. "Electrical Stimulation of Cardiac Myocytes", Annals of Biomedical Engineering, 23(6): 812-821, 1995, Abstract.

Saksena et al. "Prevention of Recurrent Atrial Fibrillation With Chronic Dual-Site Right Atrial Pacing", Journal of the American College of Cardiology, 28(3): 687-694, 1996, Abstract.

Saveliev et al. "Guidebook on Clinical Endoscopy", Moscow Medicine, p. 21, 35, Extract, 1985.

Schwartz et al. "Exposure of Frog Hearts to CW or Amplitude-Modified VHF Fields: Selective Efflux of Calcium Ions at 16 Hz", Bioelectromagnetics, 11(4): 349-358, 1990, Abstract.

Shumaik et al. "Oleander Poisoning: Treatment With Digoxin-Specific Fab Antibody Fragments", Annals of Emergency Medicine, 17(7): 732-735, 1988.

Skale et al. "Inhibition of Premature Ventricular Extrastimuli by Subthreshold Conditioning Stimuli", Journal of the American College of Cardiology, 6: 133-140, 1985. Abstract.

Solomonow et al. "Control of Muscle Contractile Force Through Indirect High-Frequency Stimulation", American Journal of Physical Medicine, 62(2): 71-82, Apr. 1983. Abstract.

Stevenson et al. "Electrophysiologic Characteristics of Ventricular Tachycardia or Fibrillation in Relation to Age of Myocardial Infarction", The American Journal of Cardiology, 57(6): 387-391, Feb. 15, 1986. Abstract.

Sweeny et al. "Countershock Strength-Duration Relationship for Myocardial Refractory Period Extension", Academic Emergency Medicine, 2(1): 57-62, 1995, Abstract.

Sweeny et al. "Refractory Interval After Transcardiac Shocks During Ventricular Fibrillation", Circulation, 94(11): 2947-2952, 1996.

Sweeny et al. "Ventricular Refractory Period Extension Caused by Defibrillation Shocks", Circulation, 82(3): 965-972, 1990.

Talit et al. "The Effect of External Cardiac Pacing on Stroke Volume", Pace, 13(5): 598-602, 1990. Abstract.

Taniguchi et al. "Inhomogeneity of Cellular Activation Time and Vmax in Normal Myocardial Tissue Under Electrical Field Stimulation", Am. J. Physiol., 267: H694-H705, 1994, Abstract.

Thakor et al. "Effect of Varying Pacing Waveform Shapes on Propagation and Hemodynamics in the Rabbit Heart", The Americal Journal of Cardiology, 79(6A): 36-43, 1997, Abstract.

Tsong "Electroporation of Cell Membranes", Biophysical Journal, 60: 297-306, 1991.

Verrier et al. "Electrophysiologic Basis for T Wave Alternans as An Index of Vulnerability to Ventricular Fibrillation", Journal of Cardiovascular Electrophysiology, 5(5): 445-461, 1994. Abstract.

Webster "Design of Cardiac Pacemakers", IEEE Press, p. xi-xiii, 1995.

Wessale et al. "Stroke Volume and the Three Phase Cardiac Output Rate Relationship With Ventricular Pacing", PACE, 13: 673-680, 1990.

Windle et al. "Subthreshold Conditioning Stimuli Prolong Human Ventricular Refractoriness", American Journal of Cardiology, 57(6): 381-386, 1986. Abstract.

Wirtzfeld et al. "Physiological Pacing: Present Status and Future Developments", Pace, 10(Part I): 41-57, 1987. Abstract.

Yokoyama "The Phase of Supernormal Excitation in Relation to the Strength of Subthreshold Stimuli", Japanese Heart Journal, 17(3): 315-325, May 1976.

Zipes et al. "Cardiac Electrophysiology—From Cell to Bedside", Saunders Co., 4th Ed., 1990.

Communication Pursuant to Article 94(3) EPC Dated Mar. 11, 2008 From the European Patent Office Re.: Application No. 06127216.7.

Communication Under Rule 71(3) EPC Dated Oct. 7, 2008 From the European Patent Office Re.: Application No. 06127216.7.

(56) References Cited

OTHER PUBLICATIONS

Notice of Allowance Dated Aug. 9, 2010 From the US Patent and Trademark Office Re.: U.S. Appl. No. 11/736,183.
Notice of Allowance Dated Feb. 15, 2011 From the US Patent and Trademark Office Re.: U.S. Appl. No. 11/932,963.
Notice of Allowance Dated Apr. 19, 2010 From the US Patent and Trademark Office Re.: U.S. Appl. No. 11/932,812.
Notice of Allowance Dated Mar. 29, 2012 From the US Patent and Trademark Office Re.: U.S. Appl. No. 11/736,183.
Notice of Reason for Rejection Dated Jun. 12, 2007 From the Japanese Patent Office Re.: Application No. 2000-502823.
Notice of Reasons for Rejection Dated Oct. 3, 2006 From the Japanese Patent Office Re.: Application No. 2000-502823.
Office Action Dated Nov. 29, 2004 From the Israeli Patent Office Re.: Application No. 133902.
Official Action Dated Mar. 8, 2010 From the US Patent and Trademark Office Re.: U.S. Appl. No. 11/736,183.
Official Action Dated Dec. 11, 2009 From the US Patent and Trademark Office Re.: U.S. Appl. No. 11/932,881.
Official Action Dated Sep. 15, 2009 From the US Patent and Trademark Office Re.: U.S. Appl. No. 11/736,183.
Official Action Dated Jun. 22, 2010 From the US Patent and Trademark Office Re.: U.S. Appl. No. 11/736,183.
Official Action Dated Feb. 23, 2010 From the US Patent and Trademark Office Re.: U.S. Appl. No. 11/932,963.
Official Action Dated Jun. 26, 2009 From the US Patent and Trademark Office Re.: U.S. Appl. No. 11/932,812.
Official Action Dated Jun. 28, 2010 From the US Patent and Trademark Office Re.: U.S. Appl. No. 11/932,963.
Official Action Dated Aug. 31, 2011 From the US Patent and Trademark Office Re.: U.S. Appl. No. 11/736,183.
Requisition by the Examiner Dated Sep. 5, 2008 From the Canadian Intellectual Property Office Re.: Application No. 2,296,632.
Requisition by the Examiner Dated Jul. 14, 2004 From the Canadian Intellectual Property Office Re.: Application No. 2,296,632.
Requisition by the Examiner Dated Nov. 23, 2006 From the Canadian Intellectual Property Office Re.: Application No. 2,296,632.
Antoni et al. "Polarization Effects of Sinusoidal 50-Cycle Alternating Current on Membrane Potential of Mammalian Cardiac Fibres", Pfl?gers Archiv European Journal of Physiology, 314(4): 274-291, 1970. Abstract.
Babsky et al. Translation of Physiology of Man, Moscow Medicine, p. 115, 348-351, 376, Extracts.
Devedeux et al. "Uterine Electromyography: A Critical Review", American Journal of Obstetric Gynecology, 169: 1636-1653, 1993.
Holst et al. "Nervous Contril of Pancreatic Endocrine Secretion in Pigs. I. Insulin and Glucagon Responses to Electrical Stimulation of the Vagus Nerves", Acta Physiologica Scandinavica, 111(1): 1-7, Jan. 1981. Abstract.
Holst et al. "Nervous Control of Pancreatic Endocrine Secretion in Pigs. II. The Effect of Pharmacological Blocking Agents on the Response to Vagal Stimulation", Acta Physiologica Scandinavica, 111(1): 9-14, Jan. 1981. Abstract.
Park et al. "Significant Cholinergic Role in Secretin-Stimulated Exocrine Secretion in Isolated Rat Pancreas", American Journal of Physiology, AJP—Gastrointestinal and Liver Physiology, 274(2): G413-G418, Feb. 1998.
Pokrovsky et al. Physiology of Man, 1: 82-83, 94, 2: 42, 54.
Saveliev et al. Guidebook on Clinical Endoscopy, p. 21, 35, Extract.
Shmit et al. Physiology of Man, 1: 78, 1996.
Shuba et al. Physiology of Vessel Smooth Muscles, p. 11-15, 142, 1988.
Singh et al. "Effects of Islet Hormones on Nerve-Mediated and Acetylcholine-Evoked Secretory Responses in the Isolated Pancreas of Normal and Diabetic Rats", International Journal of Molecular Medicine, 1(3): 627-634, Mar. 1998. Abstract.
Van Riper et al. "Electrical Field Stimulation—Mediated Relaxation of A Rabbit Middle Cerebral Artery. Evidence of A Cholinergic Endothelium-Dependent Component", Circulation Research, 70: 1104-1112, 1992.
Zhou et al. "Prevention of Action Potentials During Extracellular Electrical Stimulation of Long Duration", Journal of Cardiovascular & Electrophysiology, 8(7): 779-789, 1997. Abstract.
Communication Pursuant to Article 94(3) EPC Dated Jun. 18, 2013 From the European Patent Office Re.: Application No. 04745004.4.
Official Action Dated Jun. 14, 2013 From the U.S. Appl. No. 10/526,708.
Official Action dated Jul. 2, 2013 From the U.S. Appl. No. 10/570,576.
Notice of Allowance Dated Aug. 1, 2013 From the U.S. Appl. No. 10/599,015.
Official Action Dated Jul. 2, 2013 From U.S. Appl. No. 10/570,576.
Official Action Dated Sep. 12, 2013 From the U.S. Appl. No. 10/804,560.
Official Action Dated Nov. 14, 2013 From U.S. Appl. No. 11/884,389.
Official Action Dated Nov. 27, 2013 From U.S. Appl. No. 10/570,576.

* cited by examiner

GASTROINTESTINAL METHODS AND APPARATUS FOR USE IN TREATING DISORDERS AND CONTROLLING BLOOD SUGAR

CROSS-REFERENCES TO RELATED APPLICATIONS

This application is a continuation of co-pending PCT Patent Application No. PCT/IL2004/000664, filed Jul. 21, 2004, which is based upon and claims priority from U.S. Provisional Patent Application Ser. No. 60/488,964 to Ben-Haim et al., filed Jul. 21, 2003, entitled, "Gastrointestinal methods and apparatus for use in treating disorders and controlling blood sugar," which is assigned to the assignee of the present patent application and is incorporated herein by reference.

FIELD OF THE INVENTION

The present invention relates generally to treatment of metabolic conditions, and specifically to invasive techniques and apparatus for treating metabolic and behavioral conditions.

BACKGROUND OF THE INVENTION

Invasive treatments for obesity are often recommended for patients with a body mass index (mass/height$^2$ [kg/m$^2$]) which is greater than 35 or 40. For such patients, their weight is commonly associated with increased risk of heart disease, diabetes, and arthritis. Preferably, the invasive treatments are accompanied by changes in lifestyle, such as improved eating habits and an appropriate exercise regimen.

U.S. patent application Ser. No. 09/734,358 to Flesler et al., which published as U.S. Patent Application Publication 2002/0161414, and which is assigned to the assignee of the present patent application and is incorporated herein by reference, describes apparatus for treating a condition such as obesity. The apparatus includes a set of one or more electrodes, which are adapted to be applied to one or more respective sites in a vicinity of a body of a stomach of a patient. A control unit is adapted to drive the electrode set to apply to the body of the stomach a signal, configured such that application thereof increases a level of contraction of muscle tissue of the body of the stomach, and decreases a cross-sectional area of a portion of the body of the stomach for a substantially continuous period greater than about 3 seconds.

PCT Publication WO 02/082968 to Policker et al., which is assigned to the assignee of the present application and is incorporated herein by reference, describes a diet evaluation gastric apparatus, which detects when a patient swallows, and detects the type and amount of matter ingested. The apparatus includes electrodes adapted to be coupled to the fundus and antrum of the patient and to measure electrical and mechanical activity therein, and a control unit to analyze such electrical and mechanical activity and optionally apply electrical energy to modify the activity of tissue of the patient.

PCT Publication WO 02/053093 to Policker et al., which is assigned to the assignee of the present application and is incorporated herein by reference, describes a method for treating a subject, including receiving a sensor signal responsive to the subject eating, analyzing the sensor signal, and driving a current into tissue of the subject responsive to analyzing the signal. The current is typically driven into muscle tissue of the subject's stomach. Typically, receiving the sensor signal includes sensing electrical potential change generated responsive to contraction of a muscle such as a stomach muscle of the subject.

U.S. Pat. No. 5,690,691 to Chen et al., which is incorporated herein by reference, describes a gastric pacemaker for treating obesity and other conditions. The pacemaker includes multiple electrodes which are placed at various positions on the gastrointestinal (GI) tract, and which deliver phased electrical stimulation to pace peristaltic movement of material through the GI tract.

U.S. Pat. No. 6,243,607 to Mintchev et al., which is incorporated herein by reference, describes a gastrointestinal electrical pacemaker, including multiple electrodes which are arranged around a portion of the GI tract. The electrodes stimulate smooth muscle so that local contractions of the portion of the GI tract are artificially propagated therethrough, in order to facilitate a partial emptying of the portion. Preferably, the local contractions are artificially propagated by phase locking or time shifting the electrical stimulus, which is applied to the smooth muscle circumferentially about the portion at two or more locations.

U.S. Pat. No. 5,423,872 to Cigaina, which is incorporated herein by reference, describes apparatus for applying electrical pulses to the distal gastric antrum of a patient, so as to reduce the motility of the stomach and to thereby treat obesity or another condition.

U.S. Pat. No. 5,231,988 to Wernicke et al., which is incorporated herein by reference, describes techniques for treating and controlling diabetes and other systemic pancreatic endocrine disorders attributable to abnormal levels of secretion of endogenous insulin. An electrical stimulator implanted into or worn external to the patient's body is adapted, when activated, to generate a programmable electrical waveform for application to electrodes implanted on the vagus nerve of the patient. The electrical waveform is programmed using parameter values selected to stimulate or inhibit the vagus nerve to modulate the electrical activity thereof to increase or decrease secretion of natural insulin by the patient's pancreas. The stimulator is selectively activated manually by the patient in response to direct measurement of blood glucose or symptoms, or is activated automatically by programming the activation to occur at predetermined times and for predetermined intervals during the circadian cycle of the patient. Alternatively, the automatic activation is achieved using an implanted sensor to detect the blood glucose concentration, and is triggered when the patient's blood glucose concentration exceeds or falls below a predetermined level depending on whether diabetes or hypoglycemia is being treated.

U.S. Pat. Nos. 5,188,104 and 5,263,480 to Wernicke et al., which are incorporated herein by reference, describe a method for stimulating the vagus nerve of a patient so as to alleviate an eating disorder.

U.S. Pat. Nos. 6,104,955, 6,091,992, and 5,836,994 to Bourgeois, U.S. Pat. No. 6,026,326 to Bardy, and U.S. Pat. No. 3,411,507 to Wingrove, which are incorporated herein by reference, describe the application of electrical signals to the GI tract to treat various physiological disorders.

PCT Patent Publication WO 99/03533 to Ben-Haim et al., entitled, "Smooth muscle controller," and U.S. patent application Ser. No. 09/481,253 in the national phase thereof, both of which are assigned to the assignee of the present patent application and are incorporated herein by reference, describe apparatus and methods for applying signals to smooth muscle so as to modify the behavior thereof. In particular, apparatus for controlling the stomach is described in which a controller applies an electrical field to electrodes on the stomach wall so as to modify the reaction of muscle tissue therein to an activation signal, while not generating a propagating action potential in the tissue. In the context of the present patent application and in the claims, the use of such a non-excitatory signal to modify the response of one or more cells to electrical activation thereof, without inducing action potentials in the cells, is referred to as Excitable-Tissue Control (ETC). Use of an ETC signal is described with respect to treating obesity, by applying the ETC signal to the stomach so as to delay or prevent emptying of the stomach. In addition, a method is described for increasing the motility of the gastrointestinal tract, by applying an ETC signal to a portion of the tract in order to increase the contraction force generated in the portion.

U.S. Pat. No. 6,317,631 to Ben-Haim et al., which is assigned to the assignee of the present patent application and is incorporated herein by reference, describes methods for modifying the force of contraction of a heart chamber by applying an ETC signal to the heart.

U.S. Pat. No. 5,716,385 to Mittal et al., which is incorporated herein by reference, describes a crural diaphragm pacemaker for treating gastroesophageal reflux. The pacemaker includes one or more electrodes which are placed in contact with the crural diaphragm, either by implantation or by connecting the electrodes to the skeletal muscles of the crural diaphragm through the skin. During spontaneous intermittent relaxations of the diaphragm, the electrodes stimulate the skeletal muscles of the crural diaphragm, in order to cause contraction of the lower esophageal sphincter.

U.S. Pat. No. 6,535,764 to Imran et al., which is incorporated herein by reference, describes techniques for diagnosing and treating gastric disorders. A functional device resides within the patient's stomach and is secured to the stomach wall by an attachment device. The functional device may be a sensor for sensing various parameters of the stomach or stomach environment, or may be a therapeutic delivery device. The functional device in one embodiment comprises stimulating electrodes for gastric electrical stimulation.

U.S. Pat. No. 4,696,288 to Kuzmak et al., which is incorporated herein by reference, describes calibrating apparatus adapted to be inserted into and proceeded within the stomach of human body.

U.S. Pat. No. 4,592,339 to Kuzmak et al., which is incorporated herein by reference, describes a gastric band for forming a stoma opening in a stomach for treating morbid obesity. The band is invasively placed around the stomach, and an expandable portion of the band is used to adjust the diameter of the stoma opening.

U.S. Pat. Nos. 5,449,368, 5,226,429, and 5,074,868 to Kuzmak, which are incorporated herein by reference, describe adjustable gastric bands. The size of the stoma opening of the bands can be adjusted by injecting into or removing fluid from an expandable section of the gastric bands.

U.S. Pat. No. 5,601,604 to Vincent, which is incorporated herein by reference, describes a gastric band for placement around the stomach for treating morbid obesity. The inner surface of the band is inflatable through a remote fill port. The band is invasively placed in an encircling position around the stomach by the facile closure of a single fastening means. After the band is fastened around the stomach, a fluid is injected into the inflatable inner surface, thereby constricting the stoma of the stomach.

U.S. Pat. No. 5,658,298 to Vincent et al., which is incorporated herein by reference, describes a tool for tightening a band or ligature having a buckle end and a free end during laparoscopic surgery.

PCT Publication WO 01/83019 to Vincent, which is incorporated herein by reference, describes apparatus and methods for transferring particles and fluids to or from a body of a patient, including inflating a balloon inside the body during surgical procedures to facilitate the identification of anatomical landmarks and to provide guidance for surgical dissections.

U.S. Pat. No. 5,938,669 to Klaiber et al., which is incorporated herein by reference, describes an adjustable gastric band for contracting a patient's stomach in order to fight obesity. A gastric band of a known type, implanted around the stomach and including a cavity filled with liquid, is connected by a tube to a control box and a balancing reservoir which are implanted under the skin of the patient. The box contains an electric pump and an electronic control unit capable of communicating by radio with a monitor carried by the patient and with a controller intended for the doctor. The controller can operate the pump by remote control to transfer determined volumes of liquid in a closed circuit from the gastric band to the reservoir or vice versa, to adjust the diameter of a passage in the stomach. The monitor receives and signals alarms from the control box.

U.S. Pat. No. 6,067,991 to Forsell, which is incorporated herein by reference, describes an adjustable gastric band including an elongated non-inflatable restriction member, a forming device for forming the restriction member into at least a substantially closed loop around the stomach or the esophagus to define a restriction opening, and a post-operation non-invasive adjustment device for mechanically adjusting the restriction member in the loop to change the size of the restriction opening.

U.S. Pat. No. 6,210,347 to Forsell, which is incorporated herein by reference, describes a food intake restriction device for forming a stoma opening in the stomach or esophagus of a patient.

U.S. Pat. No. 6,460,543 to Forsell, which is incorporated herein by reference, describes a food intake restriction device for forming a stoma opening in the stomach or esophagus of a patient.

U.S. Pat. No. 6,453,907 to Forsell which is incorporated herein by reference, describes an adjustable gastric band that includes an energy transmission device for wireless transmission of energy of a first form from outside the body of the patient.

U.S. Pat. No. 6,454,699 to Forsell, which is incorporated herein by reference, describes food intake restriction apparatus that includes a restriction device implanted in a patient, which engages the stomach or esophagus to form an upper pouch and a restricted stoma opening in the stomach or esophagus.

U.S. Patent Application Publication 2003/0066536 to Forsell, which is incorporated herein by reference, describes food intake restriction apparatus, including an operable restriction device implanted in a patient and engaging the stomach or esophagus to form a restricted stoma opening in the stomach or esophagus.

U.S. Patent Application Publication 2001/0011543 to Forsell, which is incorporated herein by reference, describes apparatus for treating morbid obesity or heartburn and reflux disease, including an elongated restriction member formed in a substantially closed loop around a stomach or esophagus of a human to form a stoma opening in the stomach or esophagus.

PCT Publication WO 01/41671 to Cigaina, which is incorporated herein by reference, describes a removable gastric band for controlling obesity by allowing control and/or modification of the diameter of a stomach of a patient. The gastric band comprises a closure mechanism, which allows the elongated body to close around a portion of the stomach. The gastric band can be used in conjunction with a gastric electrostimulator, and is therefore described as being potentially useful for inducing forced slimming in the initial phase of treatment for morbigenous obesity. Such electrostimulation devices may either be incorporated into the removable gastric band or located at a distance from the removable gastric band.

European Patent Application Publication 1 036 545 A2 to Moshe, which is incorporated herein by reference, describes a gastric band for attaching around a circumference of a stomach of a patient, so as to define the diameter of the stomach opening.

U.S. Pat. No. 6,511,490 to Robert, which is incorporated herein by reference, describes a gastric banding device for implantation within a person for the treatment of morbid obesity. The gastric banding device includes an inflatable band portion dimensioned to encircle the stomach, and an inflation conduit operable for conducting a percutaneously injected inflation fluid into the band portion.

U.S. Pat. No. 6,547,801 to Dargent et al., which is incorporated herein by reference, describes an implantable gastric constriction device comprising a constriction member forming a ring in its operational configuration.

U.S. Pat. No. 5,259,399 to Brown, which is incorporated herein by reference, describes a method and apparatus for causing weight loss in obese patients by occupying a segment of the stomach volume using a variable volume bladder filled with fluid.

U.S. Pat. No. 5,234,454 to Bangs, which is incorporated herein by reference, describes a method for controlling the body weight of a patient.

U.S. Pat. No. 4,416,267 to Garren et al., which is incorporated herein by reference, describes a stomach insert for treating obesity in humans by reducing the stomach volume.

U.S. Pat. No. 6,454,785 to De Hoyos Garza, which is incorporated herein by reference, describes a percutaneous intragastric balloon catheter for the treatment of obesity. The balloon is non-surgically placed in the stomach, and is collocated by percutaneous endoscopic gastrostomy (PEG). The balloon includes a valve for regulating the amount of fluid introduced or evacuated from the balloon.

INAMED Corporation (Santa Barbara, Calif.) manufactures and markets the LAP-BAND® System, an FDA-approved adjustable and reversible gastric band for treatment of obesity.

Glucagon-like-peptide-1 (GLP-1) is a known modulator of insulin secretion in the early phases of a meal and a mediator of satiety. In response to ingestion of a meal, GLP-1 is secreted into the blood by L-cells mainly located in the colon and distal small intestine. Administration of GLP-1, either subcutaneously or peripherally, has been shown to improve glycemic control, partially by restoring the first-phase insulin response and suppressing glucagon, and is therefore considered a potential treatment for obesity and Non-Insulin Dependent Diabetes Mellitus (NIDDM).

Todd J F et al., in an article entitled, "Glucagon-like peptide-1 (GLP-1): a trial of treatment in non-insulin-dependent diabetes mellitus," Eur J Clin Invest 27(6):533-6 (1997), which is incorporated herein by reference, write that "GLP-1 has the advantages of both suppressing glucagon secretion and delaying gastric emptying." They conclude, "GLP-1 improves glycaemic control even in the absence of an insulinotropic effect and is a potential treatment for NIDDM."

U.S. Pat. No. 6,191,102 to DiMarchi et al., which is incorporated herein by reference, describes pharmaceutical compositions comprising a glucagon-like peptide-1 compound for reducing body weight and treating obesity. The compositions are peripherally administered.

Luiken et al., in an article entitled, "Contraction-induced fatty acid translocase/CD36 translocation in rat cardiac myocytes is mediated through AMP-activated protein kinase signaling," Diabetes, July, 2003, 52(7):1627-34, which is incorporated herein by reference, write that contraction of rat cardiac myocytes induces translocation of fatty acid translocase (FAT)/CD36 and GLUT4 from intracellular stores to the sarcolemma, leading to enhanced rates of long-chain fatty acid (FA) and glucose uptake, respectively. Luiken et al. note that because intracellular AMP/ATP is elevated in contracting cardiac myocytes, they investigated whether activation of AMP-activated protein kinase (AMP kinase) is involved in contraction-inducible FAT/CD36 translocation. The cell-permeable adenosine analog 5-aminoimidazole-4-carboxamide-1-beta-D-ribofuranoside (AICAR) and the mitochondrial inhibitor oligomycin, similar to 4-Hz electrostimulation, are described as evoking a more than threefold activation of cardiomyocytic AMP kinase. Both AICAR and oligomycin are described as stimulating FA uptake into noncontracting myocytes by 1.4- and 2.0-fold, respectively, but ineffective in 4 Hz-contracting myocytes. These findings are interpreted to indicate that both agents stimulate FA uptake by a similar mechanism as electrostimulation, involving activation of AMP kinase, as evidenced from phosphorylation of acetyl-CoA carboxylase. Furthermore, the stimulating effects of both AICAR and oligomycin were reported as being antagonized by blocking FAT/CD36 with sulfo-N-succinimidylpalmitate, but not by inhibiting phosphatidylinositol 3-kinase with wortmannin, indicating the involvement of FAT/CD36, but excluding a role for insulin signaling. Subcellular fractionation showed that oligomycin was able to mobilize intracellularly stored FAT/CD36 to the sarcolemma. Luiken et al. conclude that AMP kinase regulates-cardiac FA use through mobilization of FAT/CD36 from a contraction-inducible intracellular storage compartment.

The following articles, which are incorporated herein by reference, may be of interest:

Gutniak M K et al., "Subcutaneous injection of the incretin hormone glucagon-like peptide 1 abolishes postprandial glycemia in NIDDM," Diabetes Care 17(9):1039-44 (1994)

Robertson M D et al., "The influence of the colon on postprandial glucagon-like peptide 1 (7-36) amide concentration in man," J Endocrinol 161(1):25-31 (1999)

Schirra J et al., "Mechanisms of the antidiabetic action of subcutaneous glucagon-like peptide-1 (7-36) amide in non-insulin dependent diabetes mellitus," J Endocrinol 156(1):177-86 (1998)

Todd J F et al., "Subcutaneous glucagon-like peptide-1 improves postprandial glycaemic control over a 3-week period in patients with early type 2 diabetes," Clin Sci (Lond) 95(3):325-9 (1998).

Vilsboll T et al., "Reduced postprandial concentrations of intact biologically active glucagon-like peptide 1 in type 2 diabetic patients," Diabetes 50(3):609-13 (2001)

SUMMARY OF THE INVENTION

In some embodiments of the present invention, gastric control apparatus for treating obesity comprises a controllable mechanical and/or electrical gastric device for modifying a volume of a stomach of a patient, and a set of one or more sensors for sensing physiological parameters indicative of ingestion by the patient. The gastric device is adapted to reduce the stomach volume below an initial stomach volume, so as to cause a sensation of satiety felt by the patient, and therefore generally reduce the patient's appetite. A control unit is adapted to receive one or more signals from the sensors, to analyze the signals, and to drive the gastric device to modify the stomach volume in real-time responsive to the analysis.

In some embodiments of the present invention, the gastric device comprises a gastric band, adapted to be placed around the stomach, and to be tightened and loosened in real time, responsive to signals received from the control unit. Tightening of the band causes a narrowing of the stomach, thereby reducing the volume of the stomach. In other embodiments, the gastric device comprises a gastric balloon, adapted to be placed in the stomach, and to be inflated and deflated in real time, responsive to signals received from the control unit. Inflation of the balloon reduces the effective volume of the stomach, and, directly or indirectly, induces distention of the stomach wall. In still other embodiments, the gastric device comprises a set of one or more electrodes which are applied to the stomach, and apply an electrical signal as to modify a contraction pattern of some of the stomach's muscles, in order to reduce the cross-sectional area of a portion of the stomach.

In some embodiments of the present invention, the control unit is adapted to drive the gastric device to reduce the stomach volume during eating by the patient. The control unit employs an eating detection algorithm to detect the eating, responsive to changes in one or more sensed parameters. The eating detection algorithm typically utilizes one or both of the following sub-algorithms for detecting eating: an impedance sub-algorithm and an electrical slow wave sub-algorithm. An increase in impedance is generally caused by stomach distension resulting from eating. Typically, impedance measurements using electrodes placed on or near the fundus detect eating somewhat earlier than do impedance measurements using electrodes placed on or near the antrum. A decrease in electrical activity in the antrum is generally caused by digestive activity resulting from the stomach filling with food.

The impedance eating detection sub-algorithm typically uses a slow-reacting formula to calculate and remove a baseline impedance value. The formula is slow reacting in order to reduce the effect of noise on the calculation of the baseline impedance value. The sub-algorithm then processes raw real-time impedance measurements by applying both a high-pass filter and a low-pass filter to the measurements, in order to effect a band-pass filter. The resulting processed impedance value is compared to a threshold value, and if found to be greater, is interpreted as an indication of eating. For some applications, the impedance sub-algorithm interprets sudden substantial changes in impedance as indications of changes in posture of the patient, rather than as indications of eating. At least one value in the filter (e.g., the baseline impedance value) is modified in response to the posture-change indication, such that the filter, during this time, operates in a non-linear fashion. Such interpretations of sudden substantial changes in impedance may reduce false detections of eating caused by changes in posture.

The electrical slow-wave eating detection sub-algorithm analyzes real-time electrical measurements, in order to detect electrical events indicative of eating by the patient. The sub-algorithm calculates the average time difference (lag) between successive recent electrical events, and interprets an average greater than a threshold value as indicative of eating. (In general, a decrease in the rate of electrical slow-waves in the antrum occurs during digestive activity caused by the stomach filling with food.) For some applications, the sub-algorithm also compares the average time difference to an upper threshold value, and interprets an average greater than the upper threshold value as indicative of a false eating detection rather than a real eating event. Such false positives may be caused by an occasional lack of detection of a slow wave by the sensors, which erroneously increases the average time difference.

In some embodiments of the present invention, a colonic stimulation system comprises a control unit and one or more electrodes, which are adapted to be applied to respective sites in a vicinity of a colon or a distal small intestine of a patient. The control unit drives the electrodes to apply electrical signals to the sites, and configures the signals to stimulate L-cells or other target tissue, which, responsive to such stimulation, increase secretion of glucagon-like-peptide-1 (GLP-1). Such secretion of GLP-1 generally improves glycemic control of the patient, and therefore serves to treat patients suffering from insulin-resistance-related conditions, such as obesity, NIDDM, heart disease, and hypertension, or healthy patients considered at risk for such conditions. For some applications, the colonic stimulation system further comprises an eating detection unit, and the control unit is configured to drive the electrodes to apply the signals responsive to a detection of eating.

The inventors hypothesize that stimulation of the colon or the distal portion of the small intestine, as described herein, may induce up-regulation of insulin sensitivity in some types of cells. This up-regulation may occur by means of (a) an indirect response to the stimulation, and/or (b) secretion of a hormone in response to the stimulation.

In some embodiments of the present invention, a stomach signal application system comprises a control unit and one or more electrodes, which are adapted to be applied to respective sites in a vicinity of a stomach of a patient. The control unit drives the electrodes to apply an Excitable-Tissue Control (ETC) signal to the sites, and configures the signal to reduce a blood glucose level of the patient. Such an improvement in glycemic control of the patient is generally useful for treating patients suffering from insulin-resistance-related conditions, such as obesity, NIDDM, heart disease, and hypertension, or healthy patients considered at risk for such conditions. For some applications, the stomach stimulation application system further comprises an eating detection unit (e.g., using techniques described herein), and the control unit is configured to drive the electrodes to apply the signal responsive to a detection of eating.

The inventors hypothesize that application of an ETC signal to the stomach, as described herein, may induce up-regulation of insulin sensitivity, either (a) systemically, or (b) in certain types of cells. This up-regulation may occur by means of (a) an indirect response to the stimulation, such as a neural pathway, and/or (b) secretion of a hormone in response to the stimulation. The inventors further hypothesize that the reduction in blood glucose level achieved using these techniques may, at least in part, be mediated by a mechanism other than an increase in insulin secretion by the patient. In particular, the inventors hypothesize that the glucose reduction may occur even in the absence of a rise in insulin.

For some applications, ETC signals are applied in response to a sensed physiological event (e.g., within 10, 100, or 1000 ms of sensing a slow wave). For some applications, ETC signals (which, as described, are non-excitatory) are applied following an artificially-applied excitatory signal (e.g., within 10, 100, or 1000 ms of the application of the excitatory signal). It is noted that although some embodiments of the present invention are described herein with respect to application of an ETC signal, this is by way of illustration and not limitation. For some applications, another signal (e.g., an excitatory signal) is applied without application of an ETC signal.

There is therefore provided, in accordance with an embodiment of the present invention, a method for detecting a change in posture of a subject, the method including:

measuring an electrical impedance between two or more sites on a stomach of the subject, and generating an impedance signal responsive thereto; and analyzing the impedance signal in order to detect the change in posture.

For some applications, the method includes:

further analyzing the impedance signal in order to detect an indication of potential eating by the subject; and interpreting the indication of potential eating as an indication of eating only if the change in posture has not been detected.

There is further provided, in accordance with an embodiment of the present invention, a method for detecting eating by a subject, the method including:

measuring an electrical impedance between two or more sites on a stomach of the subject, and generating an impedance signal responsive thereto;

analyzing the impedance signal in order to detect a change in posture of the subject;

further analyzing the impedance signal in order to detect an indication of potential eating by the subject; and interpreting the indication of potential eating as an indication of eating only if the change in posture has not been detected.

There is yet further provided, in accordance with an embodiment of the present invention, a method for treating a subject, including:

applying an electrical signal to a colon or a distal small intestine of the subject; and configuring the signal to stimulate cells to increase secretion of glucagon-like-peptide-1 (GLP-1), in order to treat the subject.

In an embodiment, the method includes detecting eating by the subject, and applying the electrical signal includes applying the signal responsive to detecting the eating.

There is also provided, in accordance with an embodiment of the present invention, a method for treating a subject, including:

applying an electrical signal to a stomach of the subject; and configuring the electrical signal to reduce a blood glucose level of the subject, in order to treat the subject.

In an embodiment, the method includes detecting eating by the subject, wherein applying the electrical signal includes applying the electrical signal responsive to detecting the eating.

Alternatively or additionally, applying the electrical signal includes applying an Excitable-Tissue Control (ETC) signal.

There is additionally provided, in accordance with an embodiment of the present invention, a method for treating a subject, including:

applying an electrical signal to a small intestine of the subject; and configuring the electrical signal to reduce a blood glucose level of the subject, in order to treat the subject.

There is yet additionally provided, in accordance With an embodiment of the present invention, a method for treating a subject, including:

applying an Excitable-Tissue Control (ETC) signal to a smooth muscle of the subject; and configuring the ETC signal to reduce a blood glucose level of the subject, in order to treat the subject.

For some applications, applying the ETC signal includes applying the ETC signal to a site of a gastrointestinal tract of the subject. In an embodiment, applying the ETC signal includes applying the ETC signal to a duodenal site of the subject Alternatively or additionally, applying the ETC signal includes applying the ETC signal to a site of a colon of the subject.

There is still additionally provided, in accordance with an embodiment of the present invention, a method for treating a subject, including:

applying an Excitable-Tissue Control (ETC) signal to cardiac muscle tissue of the subject; and configuring the ETC signal to reduce a blood glucose level of the subject, in order to treat the subject.

There is further provided, in accordance with an embodiment of the present invention, a method for treating a subject, including:

applying an electrical signal to at least one stomach site of the subject; and configuring the electrical signal to reduce a rise in a blood glucose level of the subject, in order to treat the subject.

In an embodiment, applying the electrical signal includes applying an Excitable-Tissue Control (ETC) signal.

There is still further provided, in accordance with an embodiment of the present invention, a method for treating a subject, including:

applying an electrical signal to at least one small intestine site of the subject; and configuring the electrical signal to reduce a rise in a blood glucose level of the subject, in order to treat the subject.

There is yet further provided, in accordance with an embodiment of the present invention, a method for treating a subject, including:

applying an Excitable-Tissue Control (ETC) electrical signal to at least one smooth muscle site of the subject; and configuring the ETC electrical signal to reduce a rise in a blood glucose level of the subject, in order to treat the subject.

In an embodiment, the smooth muscle site includes a gastrointestinal tract site of the subject, and applying the ETC electrical signal includes applying the ETC electrical signal to the gastrointestinal tract site.

In an embodiment, the gastrointestinal tract site includes a duodenal site of the subject, and applying the ETC electrical signal includes applying the ETC electrical signal to the duodenal site.

In an embodiment, the gastrointestinal tract site includes a colon site of the subject, and applying the ETC electrical signal includes applying the ETC electrical signal to the colon site.

In an embodiment, the at least one site includes a gastric corpus site and a gastric antrum site, and applying the signal includes applying the signal between the gastric corpus site and the gastric antrum site.

In an embodiment, the gastric corpus site includes a posterior gastric corpus site, and applying the signal includes applying the signal between the posterior gastric corpus site and the gastric antrum site.

In an embodiment, the gastric antrum site includes a posterior gastric antrum site, and applying the signal includes applying the signal between the posterior gastric corpus site and the posterior gastric antrum site.

In an embodiment, the gastric antrum site includes an anterior gastric antrum site, and applying the signal includes applying the signal between the posterior gastric corpus site and the anterior gastric antrum site.

In an embodiment, the gastric corpus site includes an anterior gastric corpus site, and applying the signal includes applying the signal between the anterior gastric corpus site and the gastric antrum site.

In an embodiment, the gastric antrum site includes a posterior gastric antrum site, and applying the signal includes applying the signal between the anterior gastric corpus site and the posterior gastric antrum site.

In an embodiment, the gastric antrum site includes an anterior gastric antrum site, and applying the signal includes applying the signal between the anterior gastric corpus site and the anterior gastric antrum site.

In an embodiment, the at least one site includes a first gastric corpus site and a second gastric corpus site, and applying the signal includes applying the signal between the first gastric corpus site and the second gastric corpus site.

In an embodiment, the first gastric corpus site includes a posterior first gastric corpus site, and applying the signal includes applying the signal between the posterior first gastric corpus site and the second gastric corpus site.

In an embodiment, the second gastric corpus site includes a posterior second gastric corpus site, and applying the signal includes applying the signal between the posterior first gastric corpus site and the posterior second gastric corpus site.

In an embodiment, the second gastric corpus site includes an anterior second gastric corpus site, and applying the signal includes applying the signal between the posterior first gastric corpus site and the anterior second gastric corpus site.

In an embodiment, the first gastric corpus site includes an anterior first gastric corpus site, and applying the signal includes applying the signal between the anterior first gastric corpus site and the second gastric corpus site.

In an embodiment, the second gastric corpus site includes a posterior second gastric corpus site, and applying the signal includes applying the signal between the anterior first gastric corpus site and the posterior second gastric corpus site.

In an embodiment, the second gastric corpus site includes an anterior second gastric corpus site, and applying the signal includes applying the signal between the anterior first gastric corpus site and the anterior second gastric corpus site.

In an embodiment, the at least one site includes a first gastric antrum site and a second gastric antrum site, and applying the signal includes applying the signal between the first gastric antrum site and the second gastric antrum site.

In an embodiment, the first gastric antrum site includes a posterior first gastric antrum site, and applying the signal includes applying the signal between the posterior first gastric antrum site and the second gastric antrum site.

In an embodiment, the second gastric antrum site includes a posterior second gastric antrum site, and applying the signal includes applying the signal between the posterior first gastric antrum site and the posterior second gastric antrum site.

In an embodiment, the second gastric antrum site includes an anterior second gastric antrum site, and applying the signal includes applying the signal between the posterior first gastric antrum site and the anterior second gastric antrum site.

In an embodiment, the first gastric antrum site includes an anterior first gastric antrum site, and applying the signal includes applying the signal between the anterior first gastric antrum site and the second gastric antrum site.

In an embodiment, the second gastric antrum site includes a posterior second gastric antrum site, and applying the signal includes applying the signal between the anterior first gastric antrum site and the posterior second gastric antrum site.

In an embodiment, the second gastric antrum site includes an anterior second gastric antrum site, and applying the signal includes applying the signal between the anterior first gastric antrum site and the anterior second gastric antrum site.

There is also provided, in accordance with an embodiment of the present invention, a method for treating a subject, including:

applying an Excitable-Tissue Control ETC) electrical signal to at least one cardiac muscle tissue site of the subject; and configuring the ETC electrical signal to reduce a rise in a blood glucose level of the subject, in order to treat the subject.

In an embodiment, configuring the electrical signal includes configuring the electrical signal to reduce a rise in a blood insulin level of the subject.

In an embodiment, applying the electrical signal includes applying five or more pulses to the site during each of a plurality of slow wave cycles of the subject.

In an embodiment, applying the electrical signal includes applying 1 to 5 pulses to the site during each of a plurality of slow wave cycles of the subject. In an embodiment, applying 1 to 5 pulses includes applying one pulse to the site during each of the plurality of slow wave cycles.

In an embodiment, applying the electrical signal includes configuring a frequency of the electrical signal to be between 1 and 30 Hz. In an embodiment, configuring the frequency includes configuring the frequency to be between 10 and 30 Hz. In an embodiment, configuring the frequency includes configuring the frequency to be between 1 and 10 Hz. configuring the frequency includes configuring the frequency to be between 2.5 and 7.5 Hz.

In an embodiment, applying the electrical signal includes configuring a frequency of the electrical signal to be between 30 and 200 Hz. In an embodiment, configuring the frequency includes configuring the frequency to be between 100 and 200 Hz. In an embodiment, configuring the frequency includes configuring the frequency to be between 30 and 100 Hz. In an embodiment, configuring the frequency includes configuring the frequency to be between 60 and 100 Hz.

In an embodiment, applying the electrical signal includes applying pulses and configuring a pulse amplitude of the pulses to be between 2 and 15 mA. In an embodiment, configuring the pulse amplitude includes configuring the pulse amplitude to be between 2.5 and 7.5 mA.

In an embodiment, applying the electrical signal includes applying pulses in a pulse train and configuring a length of the pulse train to be between 1 and 6 seconds. In an embodiment, configuring the length of the pulse train includes configuring the length of the pulse train to be between 3 and 6 seconds.

In an embodiment, applying the electrical signal includes applying a train of biphasic pulses. In an embodiment, applying the train of biphasic pulses includes setting a duration of each phase of the biphasic pulses to be between 1 and 10 ms. In an embodiment, setting the duration includes setting the duration of each phase of the biphasic pulses to be between 4 and 6 ms.

In an embodiment, applying the electrical signal includes sensing a physiological attribute of the subject and applying the electrical signal responsive thereto. In an embodiment, sensing the physiological attribute of the subject includes sensing that the subject is eating. In an embodiment, sensing the physiological attribute includes sensing a gastrointestinal tract attribute. In an embodiment, sensing the gastrointestinal tract attribute includes sensing a slow wave.

In an embodiment, applying the electrical signal includes:
applying an initiating pulse; and
applying a burst of pulses at least 100 ms following a termination of the initiating pulse.

In an embodiment, applying the initiating pulse includes applying the initiating pulse not responsively to any physiological attribute of the subject sensed within one minute prior to the applying of the initiating pulse.

In an embodiment, applying the initiating pulse includes applying the initiating pulse not responsively to any sensing of a slow wave within one minute prior to the applying of the initiating pulse.

In an embodiment, applying the burst of pulse includes configuring a frequency of the burst of pulses to be between 1 and 10 Hz.

In an embodiment, applying the burst of pulse includes configuring a frequency of the burst of pulses to be between 10 and 100 Hz.

In an embodiment, applying the initiating pulse includes sensing a physiological attribute of the subject and applying the initiating pulse responsive thereto. In an embodiment, sensing the physiological attribute includes sensing a gastrointestinal tract attribute of the subject. In an embodiment, sensing the gastrointestinal tract attribute includes sensing an indication of a slow wave. In an embodiment, sensing the gastrointestinal tract attribute includes sensing an indication of eating by the subject.

In an embodiment, applying the burst of pulses at least 100 ms following the termination of the initiating pulse includes initiating applying the burst of pulses less than 4 seconds following the termination of the initiating pulse. In an embodiment, applying the burst of pulse includes initiating applying the burst of pulses between 100 and 500 ms following the termination of the initiating pulse. In an embodiment, applying the initiating pulse includes configuring a duration of the initiating pulse to be between 50 and 500 ms. In an embodiment, configuring the duration includes configuring the duration to be between 50 and 150 ms.

There is additionally provided, in accordance with an embodiment of the present invention, apparatus for treating a subject, including:

a set of at least one electrode, adapted to be applied to a respective at least one stomach site of the subject, and a control unit, adapted to drive the electrode set to apply an electrical signal configured to reduce a rise in a blood glucose level of the subject.

There is still additionally provided, in accordance with an embodiment of the present invention, apparatus for treating a subject, including:

a set of at least one electrode, adapted to be applied to a respective at least one small intestine site of the subject; and a control unit, adapted to drive the electrode set to apply an electrical signal configured to reduce a rise in a blood glucose level of the subject.

There is yet additionally provided, in accordance with an embodiment of the present invention, apparatus for treating a subject, including:

a set of at least one electrode, adapted to be applied to a respective at least one smooth muscle site of the subject; and a control unit, adapted to drive the electrode set to apply an Excitable-Tissue Control (ETC) electrical signal configured to reduce a rise in a blood glucose level of the subject.

There is further provided, in accordance with an embodiment of the present invention, apparatus for treating a subject, including:

a set of at least one electrode, adapted to be applied to a respective at least one cardiac muscle tissue site of the subject; and a control unit, adapted to drive the electrode set to apply an Excitable-Tissue Control (ETC) electrical signal configured to reduce a rise in a blood glucose level of the subject.

The present invention will be more fully understood from the following detailed description of the embodiments thereof, taken together with the drawings, in which:

DETAILED DESCRIPTION OF EMBODIMENTS

Figure 1:
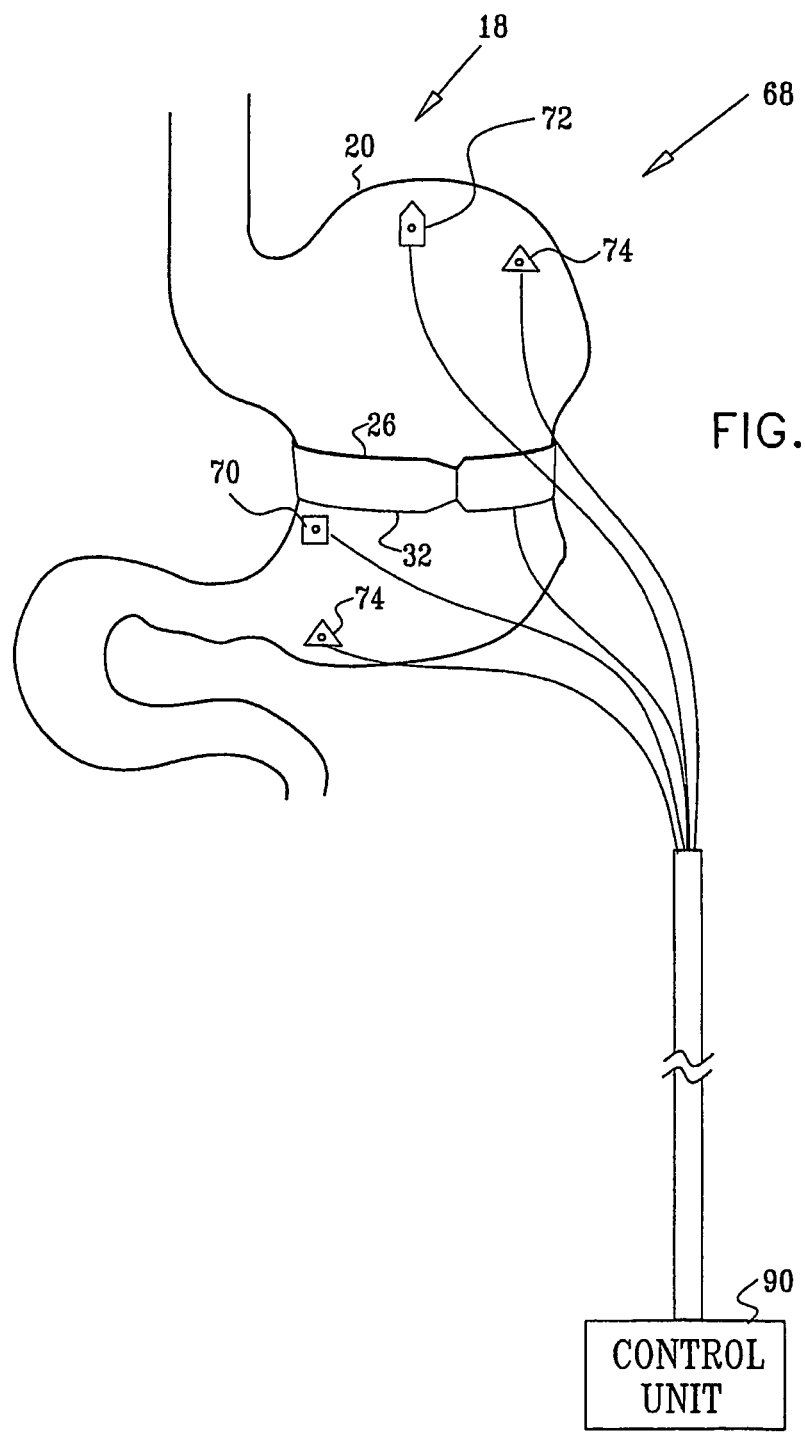
FIG. 1 is a schematic illustration of gastric control apparatus comprising an adjustable gastric band, in accordance with an embodiment of the present invention.
Figure 2:
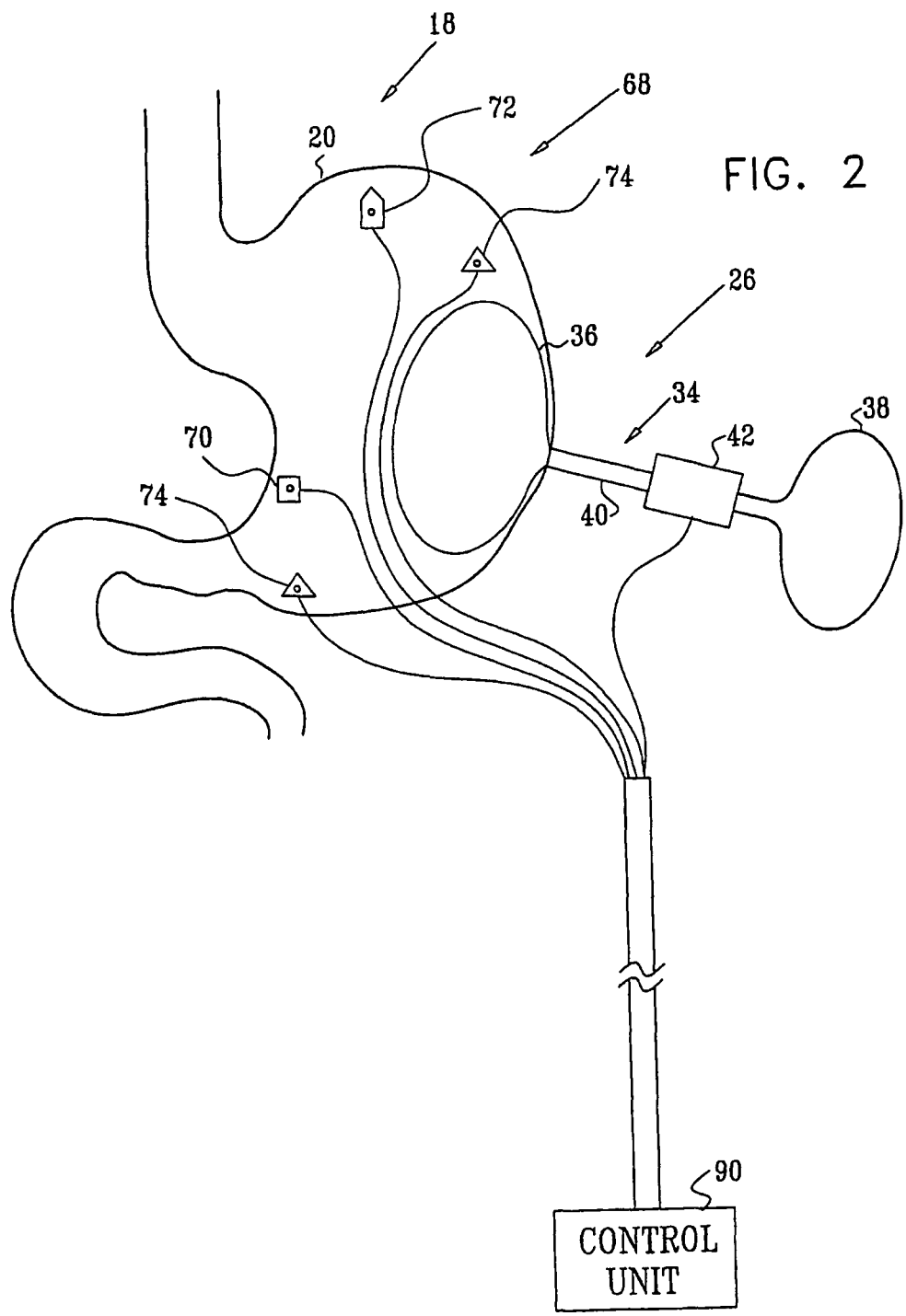
FIG. 2 is a schematic illustration of gastric control apparatus comprising a gastric balloon assembly, in accordance with an embodiment of the present invention.
Figure 3:
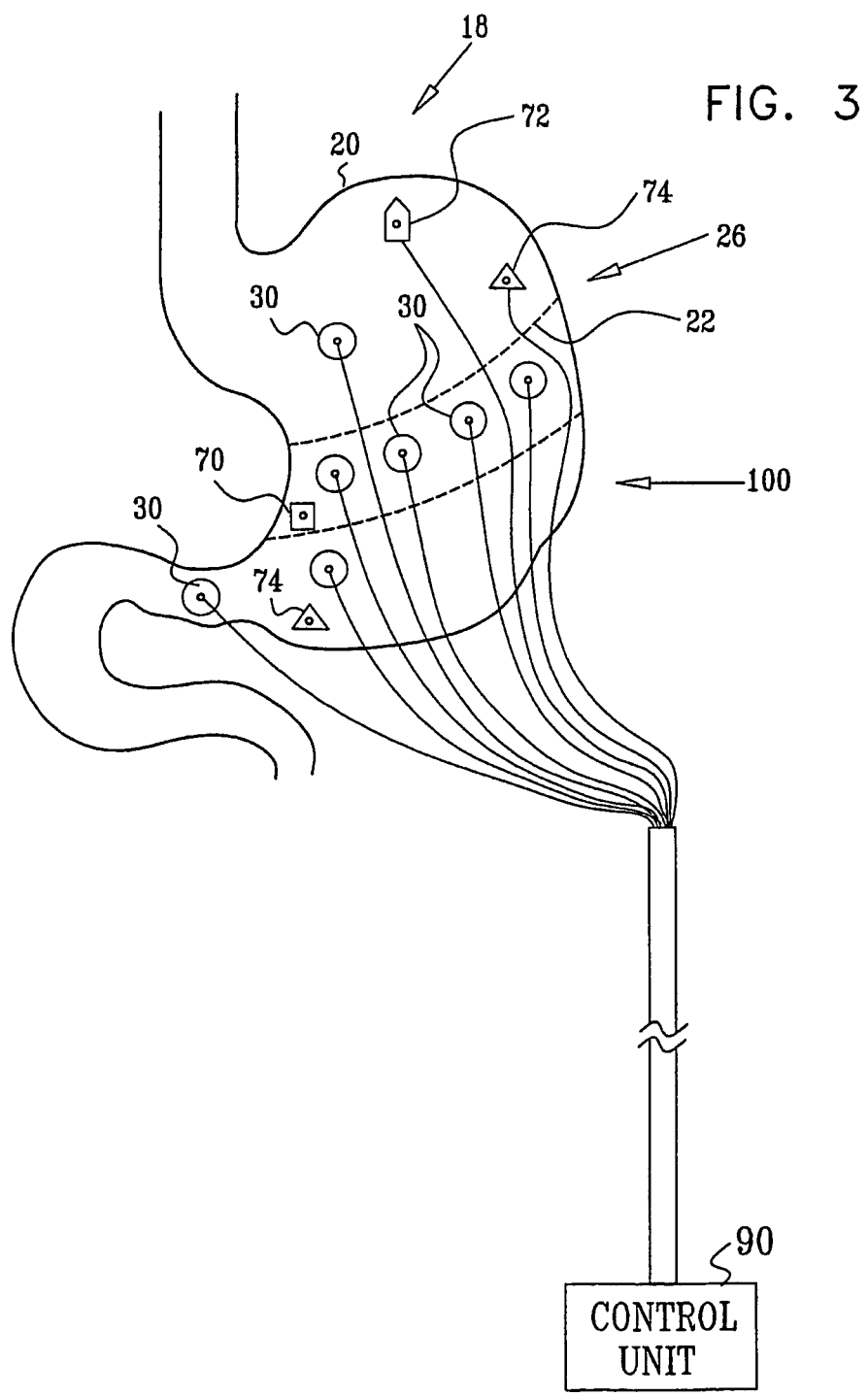
FIG. 3 is a schematic illustration of gastric control apparatus comprising one or more stimulation electrodes, in accordance with an embodiment of the present invention.

Reference is now made to FIGS. 1, 2, and 3, which are schematic illustrations of gastric control apparatus 18, in accordance with respective embodiments of the present invention. Apparatus 18 comprises an implantable or external control unit 90, and a gastric device 26, adapted to mechanically or electrically modify a volume of a stomach 20 of a patient. In the embodiment shown in FIG. 1, gastric device 26 comprises an adjustable gastric band 32, adapted to be placed around stomach 20 and tightened so as to cause a narrowing of stomach 20, thereby reducing the volume of the stomach 20. In the embodiment shown in FIG. 2, gastric device 26 comprises a gastric balloon assembly 34, a balloon 36 of which is adapted to be placed in stomach 20 and inflated so as to reduce the effective volume of stomach 20 (i.e., the volume of the stomach available for holding food before physiological indications of satiety are generated). In the embodiment shown in FIG. 3, gastric device 26 comprises one or more electrodes 100, which are driven by control unit 90 to apply an enhancement signal to respective sites on or in a vicinity of stomach 20, in order to modify a contraction pattern of some of the stomach's muscles so as to reduce the cross-sectional area of a portion of the stomach.

Apparatus 18 typically further comprises a set of one or more sensors 68 for sensing physiological parameters indicative of ingestion by the patient. Sensors 68 may comprise, for example, one or more dedicated local sense electrodes 74, which are typically placed on or in stomach 20, and convey electrical signals to control unit 90 responsive to natural gastric electric activity. Alternatively or additionally, sensors 68 comprise one or more mechanical sensors 70 (e.g., accelerometers, force transducers, strain gauges, or pressure gauges), which are placed on or in stomach 20 and are coupled to control unit 90. Further alternatively or additionally, sensors 68 comprise one or more supplemental sensors 72 (e.g., pH sensors, blood sugar sensors, intragastric pressure sensors and/or sonometric sensors), which are placed on or in the gastrointestinal tract or elsewhere on or in the body of the patient, and are coupled to control unit 90. In an embodiment, one or more of sensors 68 are fixed to a surface of gastric device 26 that comes in contact with tissue of stomach 20, such as the inner surface of gastric band 32 or the outer surface of balloon 36.

Control unit 90 is adapted to receive one or more signals from sensors 68, to analyze the signals, and to drive gastric device 26 to adjust in real-time the magnitude of stomach volume reduction responsive to the analysis. The reduced stomach volume increases the sensation of satiety felt by the patient compared to that which would be felt without such stomach volume reduction, and therefore generally reduces the patient's appetite so as to treat the obesity. Typically, control unit 90 and sensors 68 are permanently or semi-permanently implanted in or coupled to the body of the patient. The number of sensors, as well as the positions thereof, are shown in FIGS. 1-3 by way of example, and other sites on stomach 20 or in a vicinity thereof are appropriate for sensor placement in other applications of the present invention.

Figure 4:
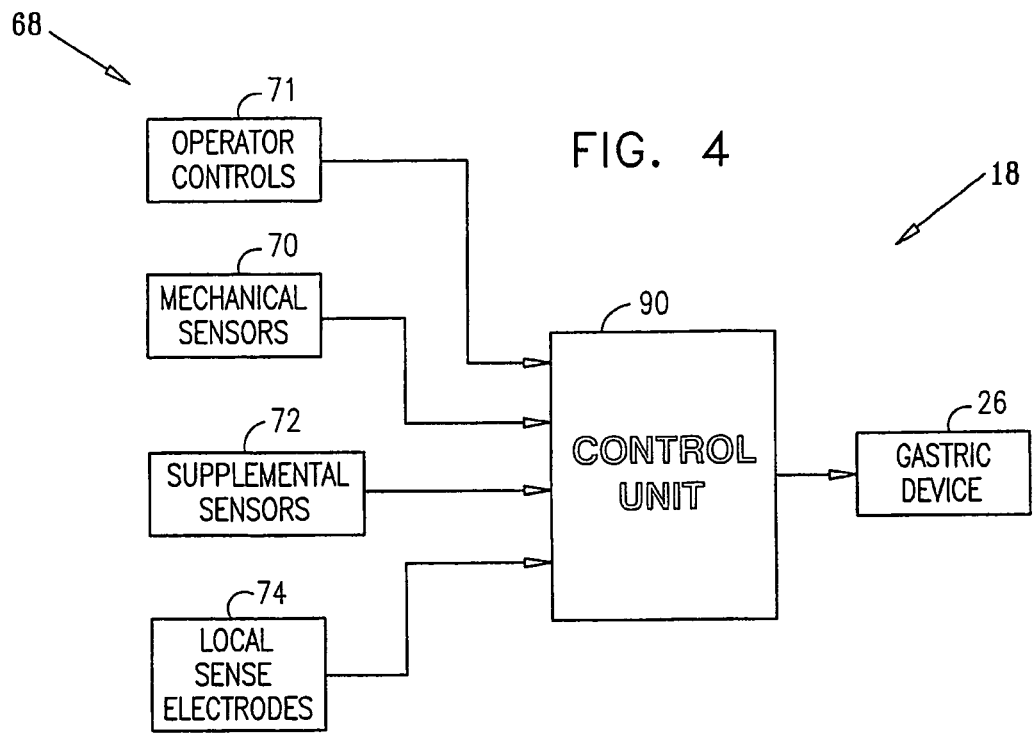
FIG. 4 is a schematic block diagram of gastric control apparatus, in accordance with an embodiment of the present invention.

FIG. 4 is a schematic block diagram of gastric control apparatus 18, in accordance with an embodiment of the present invention. Sensors 68 are typically coupled to provide feedback signals to control unit 90. The feedback signals generally provide control unit 90 with information about various aspects of the present state of the stomach (e.g., empty or full) and the level of activity of the stomach (e.g., indications of current or recent ingestion by the patient), so as to enable control unit 90 to analyze the signals and drive gastric device 26 responsive to the analysis. Typically, the magnitude of stomach volume reduction is adjusted by control unit 90 responsive to the feedback signals in order to yield a desired response, e.g., an indication by mechanical sensors 70 of a desired level of stomach contraction, or an indication by supplemental sensors 72 of maintenance of the blood sugar level of the patient within a desired range. For some applications, operator controls 71 enable the patient and/or healthcare provider to control various aspects of operation of gastric device 26.

In an embodiment of the present invention, control unit 90 employs an eating detection algorithm to detect eating by the patient, responsive to changes in one or more sensed parameters. The eating detection algorithm typically utilizes one or both of the following sub-algorithms for detecting eating: an impedance sub-algorithm and an electrical slow wave sub-algorithm. An increase in impedance is generally caused by stomach distension resulting from eating. A decrease in the rate of electrical activity in the antrum is generally caused by digestive activity resulting from the stomach filling with food.

Upon detection of an eating event, control unit 90 drives gastric device 26 to reduce a volume of stomach 20, so as to limit an ability of the patient to eat, because over-eating results in nausea, vomiting, and/or loss of appetite. Cessation of eating is typically determined by: (a) no longer detecting a particular indication of eating, and/or (b) running analogous algorithms to those described herein, but establishing different thresholds, indicative of, for example, reduction of findic pressure or restoration of basal slow-wave rates. Upon identifying the cessation of eating, the control drives gastric device 26 to restore the original stomach volume, so as, for example, to prevent counterproductive remodeling of the stomach. Alternatively or additionally, upon detection of an eating event, control unit 90 applies:

the colonic stimulation techniques described hereinbelow with reference to FIGS. 9-11; and/or the hepatic portal vein stimulation techniques described in a U.S. Provisional Patent Application entitled, "Hepatic device for treatment, eating detection, and glucose level detection," filed on Jun. 20, 2003, which is assigned to the assignee of the present patent application and is incorporated herein by reference.

Further alternatively or additionally, upon detection of an eating event, control unit 90 uses one or more techniques known in the art, including, but not limited to:

activating an insulin pump;

activating a cholecystokinin (CCK) pump (which, for some applications, is performed to treat a metabolic or behavioral disorder, in the absence of some or all of the other techniques described herein);

stimulating the pancreas using techniques described in U.S. Pat. No. 5,919,216 to Houben et al., which is incorporated herein by reference; and stimulating the vagus nerve in order to modulate insulin secretion, such as described in U.S. Pat. Nos. 5,188,104, 5,231,988, and/or 5,263,480 to Wernicke et al., which are incorporated herein by reference.

The control unit is typically configured to invoke the eating detection algorithm periodically, e.g., by sampling once every 100 milliseconds. In an embodiment of the present invention, control unit 90 implements the eating detection algorithms and sub-algorithms as a state machine.

Control unit 90 is typically configurable to allow a healthcare worker to specify which of the sub-algorithms the eating detection algorithm utilizes. If the use of both sub-algorithms is specified, the control unit performs both of the sub-algorithms essentially simultaneously, e.g., by using two microprocessors, or, alternatively, by time-sharing a single microprocessor. In addition, in such a case, the control unit is typically further configurable to specify whether an indication from both sub-algorithms is required in order for the eating detection algorithm to determine that an eating event is occurring (i.e., a logical AND operation), or whether an indication from just one of the sub-algorithms is sufficient (i.e., a logical OR operation). If an AND operation is specified, the control unit is typically still further configurable to specify the required degree of synchrony between eating detection by the two sub-algorithms, as described hereinbelow with reference to FIG. 8.

Figure 5:
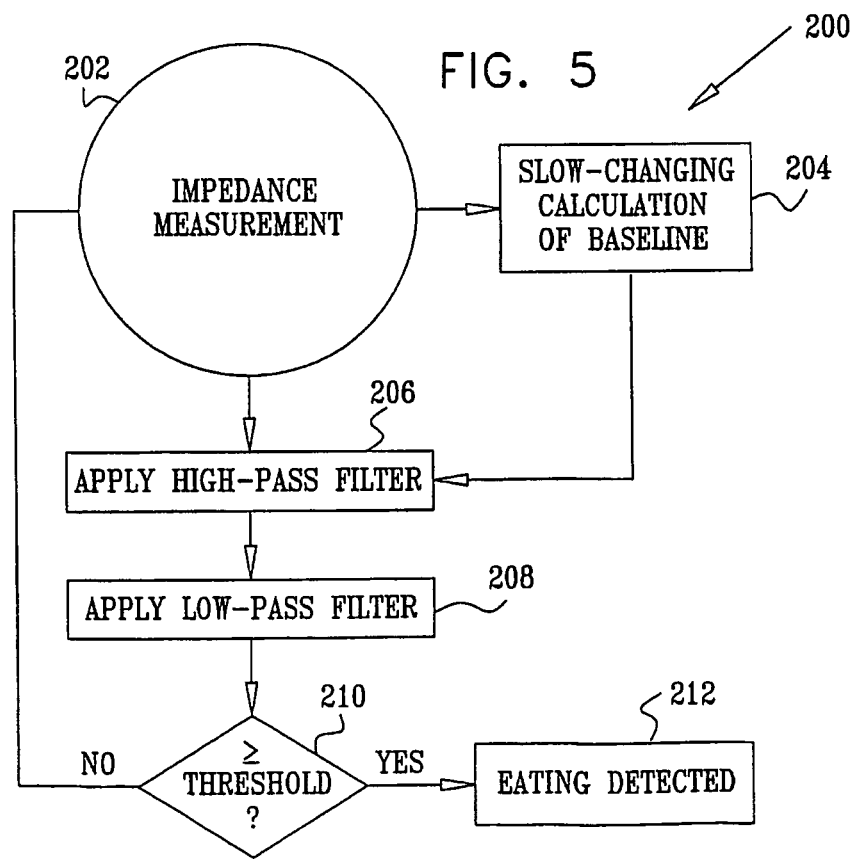
FIG. 5 is a flow chart illustrating an impedance sub-algorithm for detecting eating, in accordance with an embodiment of the present invention.

Reference is made to FIG. 5, which is a flow chart illustrating an impedance sub-algorithm 200 for detecting eating, in accordance with an embodiment of the present invention. Impedance sub-algorithm 200 has as an input an impedance measurement 202 generated by one or more local sense electrodes 74, which are typically placed on or in the findus and/or the antrum of stomach 20 for this purpose (FIGS. 1-3). In this embodiment, local sense electrodes 74 comprise two or more electrodes through which a small current is driven. A simultaneous measurement of the resultant voltage drop yields the impedance. When local sense electrodes 74 have been placed on or in both the fundus and the antrum, the control unit is typically configurable to allow a healthcare worker to select whether the impedance from the fundus and/or the antrum is used. Impedance measurement 202 is generated and inputted into the sub-algorithm periodically, e.g., once every 100 ms. It is noted that although successive impedance measurements are generally described herein as being separated by 100 ms, this is by way of illustration and not limitation. For applications in which battery life is not a significant concern, measurement periods of every 10 ms may be used. Alternatively, for some applications, impedance measurements are carried out approximately once every 1-10 seconds.

Upon receipt of impedance measurement 202, sub-algorithm 200 uses the impedance measurement to calculate a baseline value of the impedance, at a baseline calculation step 204. Sub-algorithm 200 typically uses a slow-reacting formula for calculating the baseline value, in order to avoid having high frequency noise affect the calculation of the baseline. For example, the sub-algorithm may use the following equation to calculate and update the baseline value:

$$B=[B*(N1-1)+X]/(N1*N3)$$

where B is the baseline value (initialized to zero), N1 is a constant, e.g., 512, X is impedance measurement 202, and N3 is a configurable parameter, typically having a value between about 1 and about 10. For example, N3 may have a value selected from 1, 2, 4, and 8. Higher values of N3 result in slower convergences of B to the baseline.

Sub-algorithm 200 applies a high-pass filter to impedance measurement 202, by comparing the measurement to the baseline value, at a high-pass filter step 206. Typically, the sub-algorithm performs this comparison by subtracting the baseline value from impedance measurement 202, resulting in an impedance variance value, i.e., the extent to which the impedance measurement varies from the baseline. Upon initialization of sub-algorithm 200, the sub-algorithm may repeat step 204 for a certain number of periods, so as to obtain a reasonable convergence on the baseline value, prior to performing step 206 for the first time. For some applications, this repetition of step 204 is performed during each cycle through sub-algorithm 200.

At a low-pass filter step 208, sub-algorithm 200 applies a low-pass filter to the impedance variance value, resulting in a processed impedance value. This low-pass filtering serves to smooth variations in the impedance variance value, and to filter out spurious high values. For example, sub-algorithm 200 may use the following equation to perform the low-pass filtering:

$$S=[S*(2^{N4}-1)+\Delta X]/2^{N4}$$

wherein S is the processed impedance value (initialized to zero), N4 is a configurable parameter, typically having a value between about 1 and about 5, and $\Delta X$ is the impedance variance value. For example, N4 may have a value selected from 1, 2, 3, and 4. Higher values of N4 tend to reduce false positive indications of eating, while lower values tend to reduce false negatives. In general, any of the values 1-4 is suitable.

Sub-algorithm 200 compares the processed impedance value to a configurable threshold value, at a threshold check step 210. The threshold value typically is between about 2 and about 80 ohms. For example, the threshold value may be between about 30 and about 40 ohms when local sense electrodes 74 are placed about 2.5 cm apart, approximately 2 cm inferior to the gastroesophageal junction. Because the processed impedance value represents a difference between impedance measurement 202 and the baseline value, the threshold value is typically expressed as an absolute value (i.e., in ohms), rather than as a percentage change. If sub-algorithm 200 finds that the processed impedance value is greater than the threshold, the sub-algorithm generates an impedance condition signal, at an eating detected step 212. Otherwise, the sub-algorithm waits until a new impedance measurement 202 is generated, and repeats the method. (In embodiments of the present invention that include the AND synchrony techniques described hereinbelow with reference to FIG. 8, the sub-algorithm includes the current time ($t_Z$) with the impedance eating detection signal. In addition, when the sub-algorithm does not detect eating, the sub-algorithm generates a non-impedance condition signal, including the current time ($t_{Non\ Z}$).)

Figure 6:
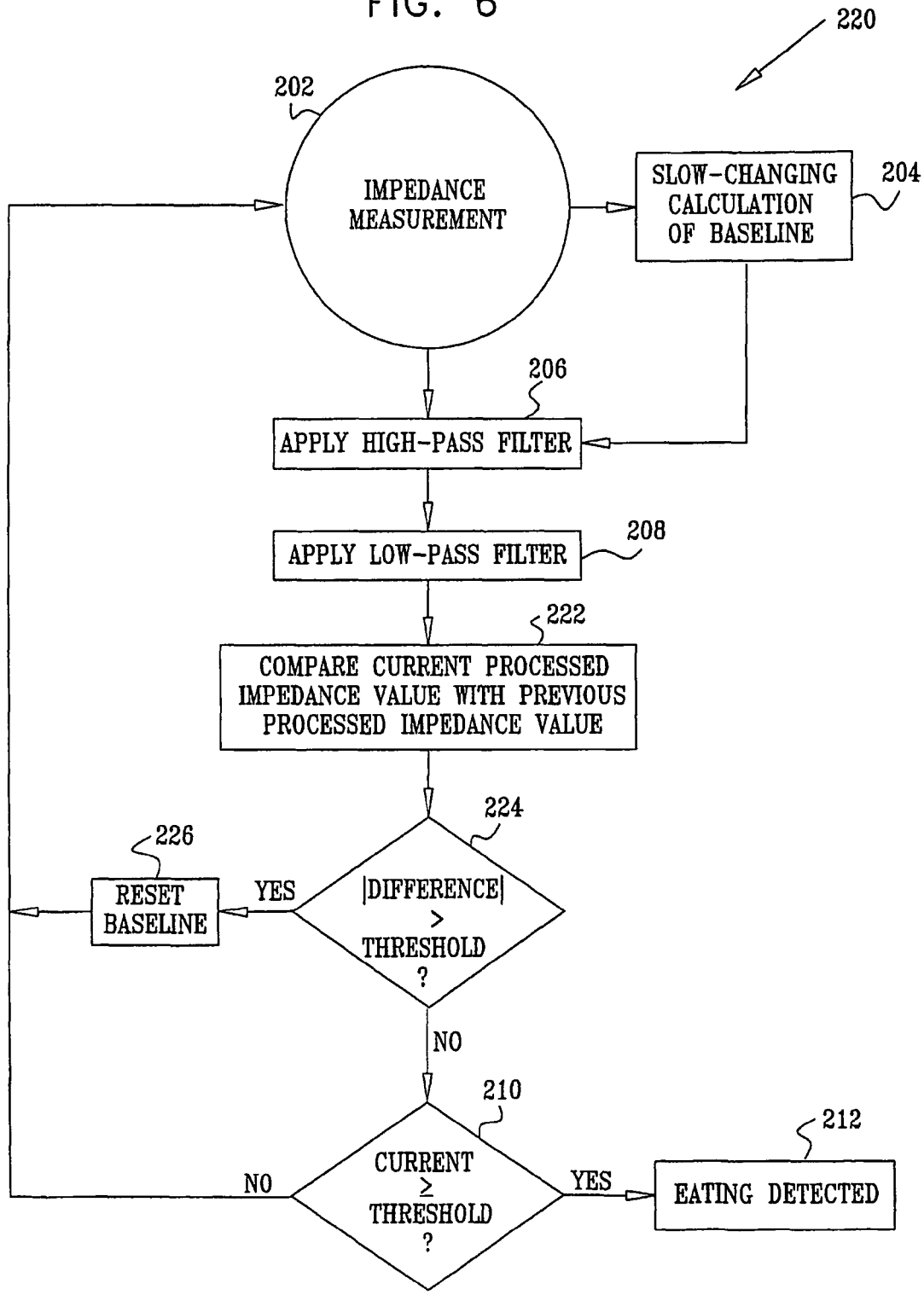
FIG. 6 is a flow chart illustrating another impedance sub-algorithm for detecting eating, in accordance with an embodiment of the present invention.

Reference is now made to FIG. 6, which is a flow chart illustrating an impedance sub-algorithm 220 for detecting eating, in accordance with an embodiment of the present invention. Impedance sub-algorithm 220 typically includes the same steps 204 through 212 as sub-algorithm 200. Sub-algorithm 220, however, contains additional steps, as described hereinbelow.

After applying the low-pass filter at step 208, as described hereinabove with reference to FIG. 5, sub-algorithm 220 compares the current processed impedance value received from the low-pass filter with a processed impedance value determined during a previous cycle through sub-algorithm 220, at a comparison step 222. The following equation expresses this comparison:

$$d=S_t-S_{t-N5}$$

where d is a difference between the current and previous processed impedance values, $S_t$ is the current processed impedance value, and $S_{t-N5}$ is the processed impedance value calculated based on the impedance measurement taken N5 periods earlier. As mentioned above, each measurement period may have a duration of 100 ms. For protocols having different measurement periods, N5 and other parameters may be suitably changed, mutatis mutandis. N5 is a configurable parameter, which typically has a value between about 1 and about 500 measurement periods, when such measurement periods have a duration of 100 ms. For example, N5 may have a value selected from 1, 5, 10, 20, 30, 50, 100, and 200 measurement periods.

The absolute value of the difference d is compared to a preconfigured threshold value, at a difference check step 224. If the difference is greater than the threshold, at a reset baseline step 226 sub-algorithm 220 resets the baseline value, by adding the current processed impedance value to the baseline value. (If the current processed impedance value is negative, such addition decreases the baseline value.) Sub-algorithm 220 waits until a new impedance measurement 202 is generated, and repeats the method. If, however, sub-algorithm 220 finds at step 224 that the difference is less than or equal to the threshold value, the sub-algorithm proceeds to check step 210, as described hereinabove with reference to FIG. 5.

For some applications, if N5 is greater than 1, sub-algorithm 220 performs check steps 224 and 210 only once per every N5 impedance measurements. Such reduced-frequency testing generally reduces power consumption and thus extends battery life of battery-operated implementations of gastric control apparatus 18.

The performance of steps 222, 224, and 226 may serve to reduce false detections of eating caused by changes in posture of the patient Changes in posture sometimes cause sudden substantial changes in impedance measurement 202. Such changes in impedance are typically larger and more sudden than changes generally caused by the commencement of eating (and the resultant gradual increase in stomach volume), and generally continue as long as the patient maintains the new posture. By resetting the baseline value at step 226, sub-algorithm 220 incorporates the sudden change in impedance into the baseline value. Sub-algorithm 220 uses the reset baseline value for the high-pass filter at step 206, beginning with the next cycle through the algorithm. It is noted that any false negatives that may be caused by the performance of steps 222, 224, and 226 are generally transient. The short delay before sub-algorithm 220 subsequently detects eating generally does not meaningfully affect the performance of gastric control apparatus 18.

Figure 7:
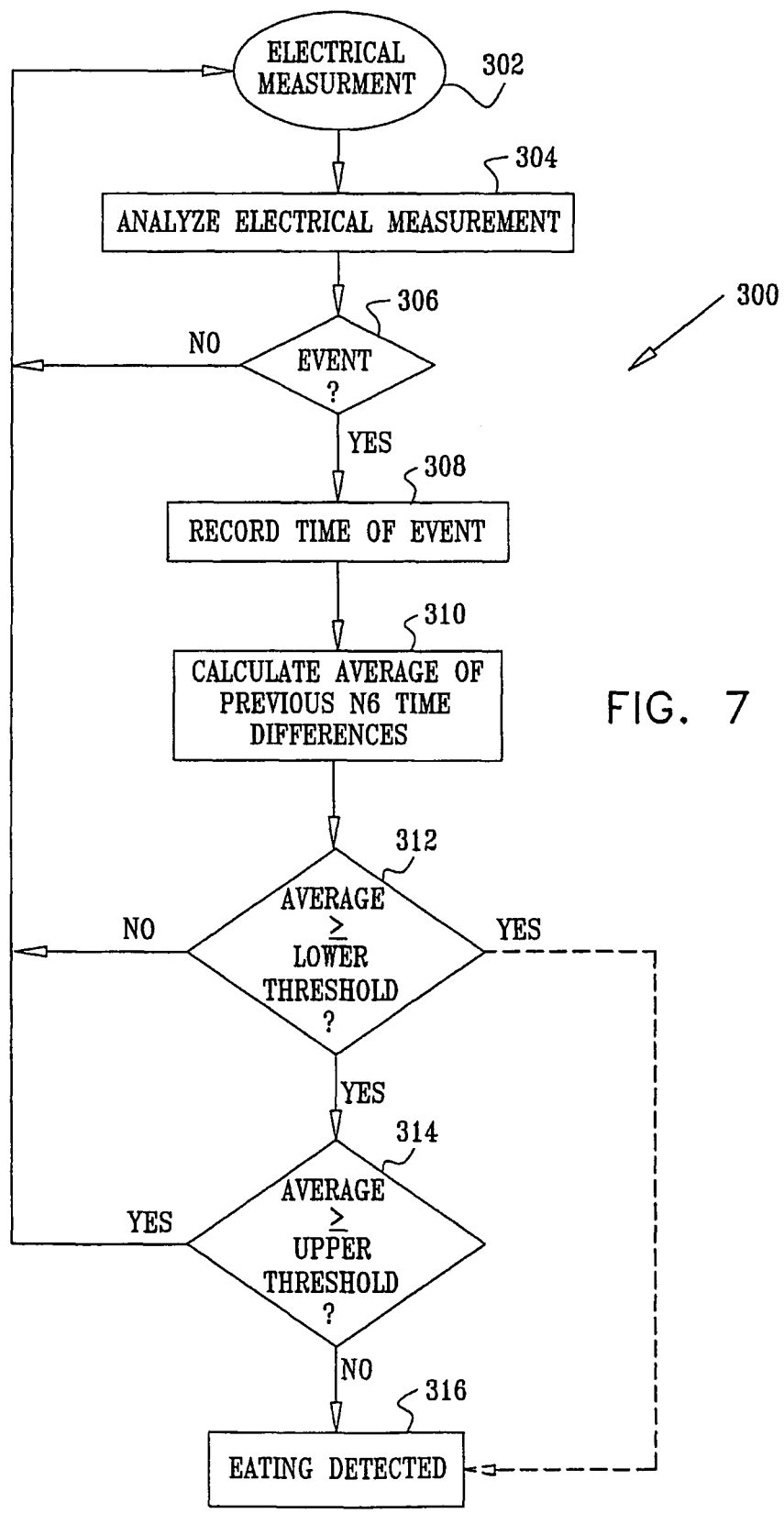
FIG. 7 is a flow chart illustrating an electrical slow-wave sub-algorithm for detecting eating, in accordance with an embodiment of the present invention.

Reference is now made to FIG. 7, which is a flow chart illustrating an electrical slow-wave sub-algorithm 300 for detecting eating, in accordance with an embodiment of the present invention. Slow-wave sub-algorithm 300 has as an input an electrical measurement 302 generated by one or more local sense electrodes 74 (FIGS. 1-3). In applications in which impedance is measured, as described hereinabove, these local sense electrodes 74 may be the same local sense electrodes 74 used for the impedance measurements, or may be separate therefrom. The sub-algorithm analyzes the electrical measurement, in order to determine whether an electrical event indicative of a slow wave has occurred, at an analysis step 304. Techniques known in the art for detecting slow waves may be utilized in analysis step 304. At an event check step 306, if the sub-algorithm does not detect an event, the sub-algorithm waits until another electrical measurement 302 is taken, and returns to the beginning of the method.

If, however, sub-algorithm 300 detects an event at step 306, the sub-algorithm records the time of the event, at a record time step 308. The sub-algorithm then calculates the time difference (lag) between the current event and the most recent previous event, and averages the most recent N6 time differences (including the current time difference), at an average calculation step 310. N6 typically has a value between about 1 and about 10; for example, N6 may be configurable to be selected from 1, 2, 4, and 6. Sub-algorithm 300 compares the average with a lower threshold value, which is typically between about 20 and about 30 seconds, at a lower threshold comparison step 312. In general, a decrease in the rate of electrical slow-waves in the antrum occurs during digestive activity caused by the stomach filling with food. Therefore, if sub-algorithm 300 finds that the average is greater than or equal to the lower threshold value, the sub-algorithm interprets such a finding as indicative of potential eating by the patient, and proceeds to an upper threshold comparison step 314, described below. On the other hand, if the sub-algorithm finds that the average is less than the lower threshold value, the sub-algorithm waits until another electrical measurement 302 is taken, and returns to the beginning of the method.

At upper threshold comparison step 314, sub-algorithm 300 compares the average time difference with an upper threshold value, which is typically between about 25 and about 80 seconds, e.g., between about 60 and 80 seconds. (The upper threshold value is typically between about 3 and about 4 times greater than the basal level of the time difference.) This comparison generally reduces false eating detections that may be caused by an occasional lack of detection of a slow wave by local sense electrodes 74. If sub-algorithm 300 finds that the average is less than the upper threshold value, the sub-algorithm generates a slow-wave condition signal, at an eating detected step 316. On the other hand, if the sub-algorithm finds that the average is greater than or equal to the upper threshold value, the sub-algorithm waits until another electrical measurement 302 is taken, and returns to the beginning of the method. For some applications, sub-algorithm omits step 314, and proceeds directly from step 312 to step 316 if the sub-algorithm finds that the average is greater than or equal to the lower threshold value. (In embodiments of the present invention that include the AND synchrony techniques described hereinbelow with reference to FIG. 8, the sub-algorithm includes the current time (trate) with the slow-wave eating detection signal.)

In an embodiment, eating detection based on interpreting electrical activity of the stomach, as described hereinabove, is supplemented by or replaced by one or more of the following protocols:

Analysis of action potential propagation velocity within slow waves. Action potential propagation velocity is typically determined by measuring the duration of a slow wave. If, for example, the average basal duration of a slow-wave is 5 seconds, then an increase of the duration by greater than about 7-15% (e.g., by 10% to 5.5 seconds) is interpreted as an indication of stomach distention or anticipation of imminent eating. A subsequent decrease in the duration towards the average basal duration is indicative of cessation of eating. Alternatively or additionally, changes in morphological features of the slow wave besides duration are analyzed to determine the onset and termination of eating.

Sensing antral contractions indicative of the onset or imminent onset of eating. An increased presence of sensed energy within a particular frequency band indicates that antral contractions are occurring, and are interpreted to indicate that eating has started or is about to start. For some applications, the energy band ranges from about 0.5 Hz to about 3 Hz, and is typically between about 1 and 2 Hz. Correspondingly, a decrease of sensed energy in the frequency band is interpreted to indicate cessation of eating.

Detecting ectopic sites of natural gastric pacing. When a sensed dysrhythmia is determined to initiate at an ectopic site, this is interpreted to indicate that the stomach is changing state (for example, filling or emptying).

Sensing efferent neural modulation of gastric electrical activity. The initiation of sensed electrical activity above about 5 Hz (e.g., between about 5 and 15 Hz) is interpreted to indicate the anticipation of imminent eating, or the onset of eating. Electrodes placed on the stomach detect this activity even when they are not placed directly on a nerve propagating the action potentials.

For some applications, multiple possible indications of eating are analyzed in combination, to increase the reliability of a determination by control unit 90 that eating is beginning. For example, if five possible indicators are evaluated, then a determination of eating may be made only if at least four out of five of the indicators are positive. In an embodiment, some of the indicators (e.g., changes in impedance and/or changes in the spacing between successive slow waves) are given a higher weight than the others.

Figure 8:
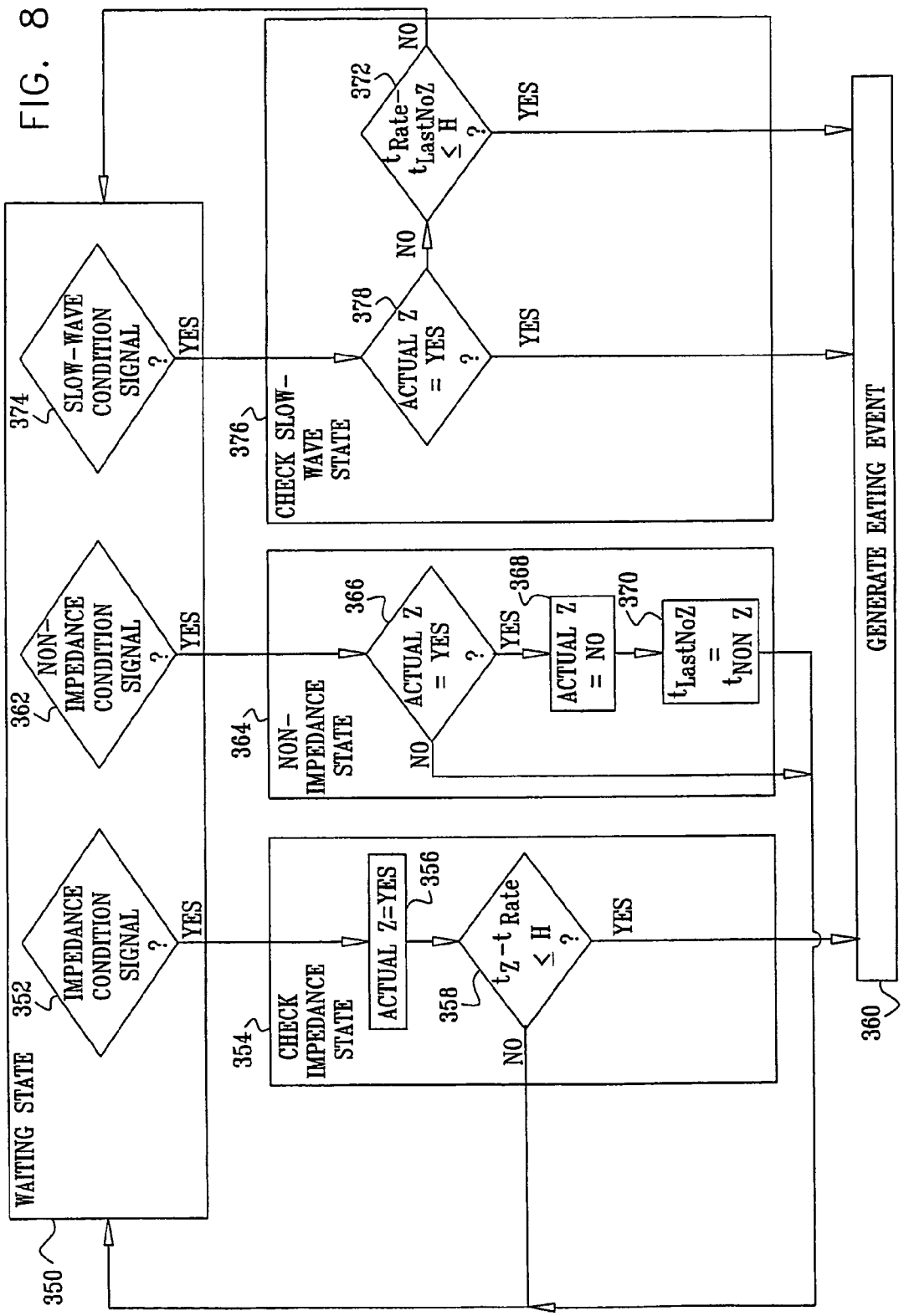
FIG. 8 is a block diagram that schematically illustrates states of a control unit during application of "AND synchrony," in accordance with an embodiment of the present invention.

Reference is made to FIG. 8, which is a block diagram that schematically illustrates states of control unit 90 during application of "AND synchrony," in accordance with an embodiment of the present invention. Control unit 90 typically implements these states when the control unit has been configured to utilize both the impedance and slow-wave sub-algorithms, and to combine the outputs from the two sub-algorithms using an AND operation with a required degree of synchrony. The control unit makes an eating determination only when the two sub-algorithms detect eating simultaneously or within a certain period of time from one another. Equivalent techniques for implementing AND synchrony will be evident to those skilled in the art who have read the present application, and are within the scope of the present invention.

The default state of control unit 90 is a waiting state 350. Upon initialization of this state, the control unit initializes the following variables (each of which is described hereinbelow): (a) Actual Z is set equal to NO, (b) $t_{LastNoZ}$ is set equal to negative infinity (or a number representative thereof, such as −32768), and (c) $t_{Rate}$ is set equal to negative infinity (or a number representative thereof, such as −32768). While in the waiting state, the control unit periodically or substantially constantly monitors whether sub-algorithms 200 and 220 generate signals, by performing the following three check steps substantially simultaneously, or by rapidly cycling through the following three check steps:

At an impedance check step 352, control unit 90 checks for an impedance condition signal, as generated at step 212, described hereinabove with reference to FIG. 5;

At an impedance check step 362, control unit 90 checks for a non-impedance condition signal, as generated as described hereinabove with reference to FIG. 5; and At a slow-wave check step 374, control unit 90 checks for a slow-wave condition signal, as generated at step 316, described hereinabove with reference to FIG. 7.

If the control unit detects an impedance condition signal at check step 352, the control unit transitions to a check impedance state 354. Upon entering check impedance state 354, control-unit 90 sets an Actual Z flag equal to YES, at a set flag step 356. This flag indicates that an impedance condition is currently occurring. The control unit then subtracts $t_{Rate}$ (which is equal to negative infinity, until a value has been received together with a slow-wave signal, as described hereinabove with reference to step 316 of FIG. 7) from $t_Z$ (which has been received together with the impedance condition signal, as described hereinabove with reference to step 212 of FIG. 5). At a synchrony check step 358, the control unit compares the resulting difference with a synchrony constant H, which is typically between 0 and about 300 seconds, e.g., 180 seconds. If the difference is less than H, indicating the control unit received impedance condition and slow-wave signals within H seconds of one another, the control unit generates an eating event, at an eating event generation step 360, and concludes the algorithm. On the other hand, if the control unit finds that the difference is greater than or equal to H, the control unit transitions back to waiting state 350.

While in waiting state 350, if the control unit detects a non-impedance condition signal at check step 362, the control unit transitions to a non-impedance state 364. If, at an Actual Z check step 366, the control unit finds that Actual Z equals YES, the control unit sets Actual Z to NO, at an Actual Z set step 368. In addition, at a $t_{LastNoZ}$ set step 370, the control unit sets $t_{LastNoZ}$ equal to $t_{non\ Z}$, which was generated as described hereinabove with reference to FIG. 5. Thus, $t_{LastNoZ}$ now indicates the time when the most recent active impedance condition terminated. $t_{LastNoZ}$ is used as described hereinbelow with reference to a comparison step 372. The control unit then transitions back to waiting state 350.

While in waiting state 350, if the control unit detects a slow-wave condition signal at check step 374, the control unit transitions to a check slow-wave state 376. The control unit checks whether Actual Z equals YES, at an Actual Z check step 378. If the control unit finds that Actual Z does equal YES, indicating that the control unit has received the slow-wave condition signal during an active impedance condition, then the control unit generates an eating event, at eating event generation step 360, and concludes the algorithm. On the other hand, if the control unit finds that Actual Z does not equal YES, the control unit checks whether $t_{Rate}-t_{LastNoZ}$ is less than H, at check step 372. If the control unit finds that $t_{Rate}-t_{LastNoZ}$ is less than H, indicating that the most recent impedance event concluded within H seconds of detection of the current slow-wave, then the control unit generates an eating event, at eating event generation step 360, and concludes the algorithm Otherwise, the control unit transitions back to waiting state 350.

For some applications, control unit 90 drives gastric device 26 to reduce and/or restore the stomach volume according to a schedule, so as to induce reduction of the stomach volume at times when the patient might choose to eat but should not be eating, or when the patient's eating should be minimized. At other times, e.g., when the patient is sleeping, control unit 90 drives gastric device 26 to restore the stomach volume. Alternatively or additionally, control unit 90 (a) reduces the stomach volume during one or more meals during the day, so as to reduce the patient's appetite during those meals, and (b) restores the stomach volume during meals eaten during the remainder of the day, so as to prevent undesired side effects (e.g., nutritional deficiencies) which might occur in some patients from any inappropriate, excessive use of the stomach volume reduction techniques described herein.

Alternatively or additionally, the patient activates, deactivates, and modulates the level of stomach volume reduction in accordance with physician's instructions, aspects of the patient's diet, or other factors. For example, the patient may eat soup and salad at dinner, and then activate the control unit using operator controls 71, so as to increase the sense of satiety prior to being presented with a large selection of high-calorie options for an entree. The patient may subsequently input a command for a higher level of stomach volume reduction during dessert, such that the patient will feel very full, and, in fact, not have space for the dessert It is seen through this example that this embodiment of the present invention can be used to encourage the patient to fully satisfy all nutritional needs, while simultaneously reducing or eliminating the hunger sensation which the patient would otherwise feel if stomach 20 were not in the reduced volume state caused by gastric device 26.

Reference is again made to FIG. 1. In this embodiment, the circumference of gastric band 32 is bidirectionally adjustable in real time responsive to input from control unit 90. The gastric band typically, but not necessarily, utilizes one or more of the following techniques for controllably adjusting the circumference thereof:

Gastric band 32 comprises a motor, such as a linear motor or a rotary motor, which is adapted to contract and expand gastric band 32. For example, motorized adjustment techniques may be used that are described in the above-referenced U.S. Pat. Nos. 6,067,991 and/or 6,454,699, and/or in the above-referenced U.S. Patent Application Publications 2003/0066536 and/or 2001/0011543.

At least a portion of gastric band 32 comprises a temperature-sensitive material, the compliance and/or length of which varies in response to temperature changes. Control unit 90 applies changes in temperature to the material so as to achieve a desired stomach volume Gastric band 32 comprises a portion that is inflatable through a fill port. For example, an inner surface of the band may comprise the inflatable portion. Typically, the portion is inflated with a liquid, such as saline solution. The inflatable portion is typically connected by a tube to a balancing reservoir that is implanted under the skin of the patient. Band 32 further comprises a pump, which, responsive to input from control unit 90, transfers determined volumes of liquid in a closed circuit from the band to the reservoir or vice versa, to adjust the circumference of the band. For example, adjustable band inflation techniques may be used that are described in the above-referenced U.S. Pat. Nos. 5,938,669, 6,460,543, 6,453,907, and/or 6,454,699, and/or in the above-referenced US Patent Application Publications 2003/0066536 and/or 2001/0011543.

Alternatively or additionally, other techniques described in one or more of the publications referred to in the Background of the Invention are utilized for controllably adjusting the circumference of gastric band 32.

Reference is again made to FIG. 2. The volume of balloon 36 is bidirectionally adjustable in real time responsive to input from control unit 90. Typically, gastric balloon assembly 34 comprises a fluid reservoir 38 connected to balloon 36 by a tube 40. A valve 42, responsive to input from control unit 90, controls the amount of fluid introduced into or released from the balloon, in order to control the volume of the balloon, and thus the volume of stomach 20 remaining for containing food. For some applications, valve 42 comprises a pump. Adjustable balloon inflation techniques may be used that are described in the above-referenced U.S. Pat. No. 5,259,399. Alternatively or additionally, other techniques described in one or more of the publications referred to in the Background of the Invention are utilized for controllably adjusting the volume of balloon 36.

Reference is again made to FIG. 3. At least some of the sites to which electrodes 100 are applied are typically located on the body of the stomach, i.e., that portion of the stomach located between the lower-esophageal sphincter and the pyloric sphincter. The enhancement signal applied by electrodes 100 is typically configured so as to modulate contraction of muscles of the stomach and to thereby treat obesity. Typically, the enhancement signal includes, as appropriate, an Excitable-Tissue Control (ETC) signal and/or an excitatory signal which induces contraction of muscles of the stomach. Aspects of ETC signal application are typically performed in accordance with techniques described in the above-referenced PCT Publications WO 99/03533 and its corresponding U.S. national phase application Ser. No. 09/481,253, and/or U.S. Pat. No. 6,317,631 to Ben-Haim et al., mutatis mutandis. For some applications, the ETC signal is applied responsive to natural electrical activity of stomach 20, for example, after a designated delay following a detected activation of a portion of the stomach. For these applications, apparatus and methods may be used that are described in Israel Patent Application 129,257, entitled "Trigger-based regulation of excitable tissue control in the heart," mutatis mutandis. This application is assigned to the assignee of the present invention and is incorporated herein by reference.

Typically, control unit 90 drives electrodes 100 to apply the enhancement signal so as to create a contraction pattern of some of the muscles of stomach 20, in order to reduce the cross-sectional area of a portion 22 of the stomach. This reduction is believed to increase the sensation of satiety felt by the patient compared to that which was felt prior to application of the enhancement signal. Typically, the enhancement signal is configured such that the cross-sectional area of the stomach is reduced by at least 20%, and this reduction is maintained in one region of the stomach for a period of at least 1 minute. It is to be understood that for some applications, greater or lesser reductions in cross-sectional area may be desirable, and these may be maintained for periods greater or less than 1 minute.

Electrodes 100 typically comprise one or more signal application electrodes 30, which may also operate in a sensing mode. Electrodes 100 are typically coupled to the serosal layer of the stomach and/or inserted into the muscular layer of the stomach. Alternatively or additionally, the electrodes are coupled elsewhere on the stomach, gastrointestinal tract, or to other suitable locations in or on the body of the patient. The number of electrodes, as well as the positions thereof, are shown in FIG. 3 by way of example, and other sites on stomach 20 or in a vicinity thereof are appropriate for electrode placement in other applications of the present invention. Different types of electrodes known in the art are typically selected based on the specific manifestation of the patient's condition, and may comprise stitch, coil, screw, patch, basket, needle and/or wire electrodes, or substantially any other electrode known in the art of electrical stimulation or sensing in tissue.

For some applications, techniques described herein are performed in combination with techniques described in the above-referenced U.S. Patent Application Publication 2002/0161414. For example, in embodiments of the present invention that comprise electrodes 100, control unit 90 may utilize the techniques described in the '414 patent application publication with reference to FIG. 2 thereof (regarding the operation of the control unit).

For some applications, electrodes 100 apply electrical stimulation in combination with the mechanical stomach volume modification techniques described hereinabove with reference to FIGS. 1 and 2. For example, electrical stimulation may be applied in order to achieve greater stomach volume reduction than is achievable by use of these mechanical techniques alone. In an embodiment, one or more of electrodes 100 is fixed to a surface of (a) gastric band 32 (FIG. 1) that comes in contact with tissue of stomach 20, such as the inner surface of gastric band 32, or (b) a surface of gastric balloon assembly 34 (FIG. 2) that comes in contact with tissue of stomach 20.

Figure 9:
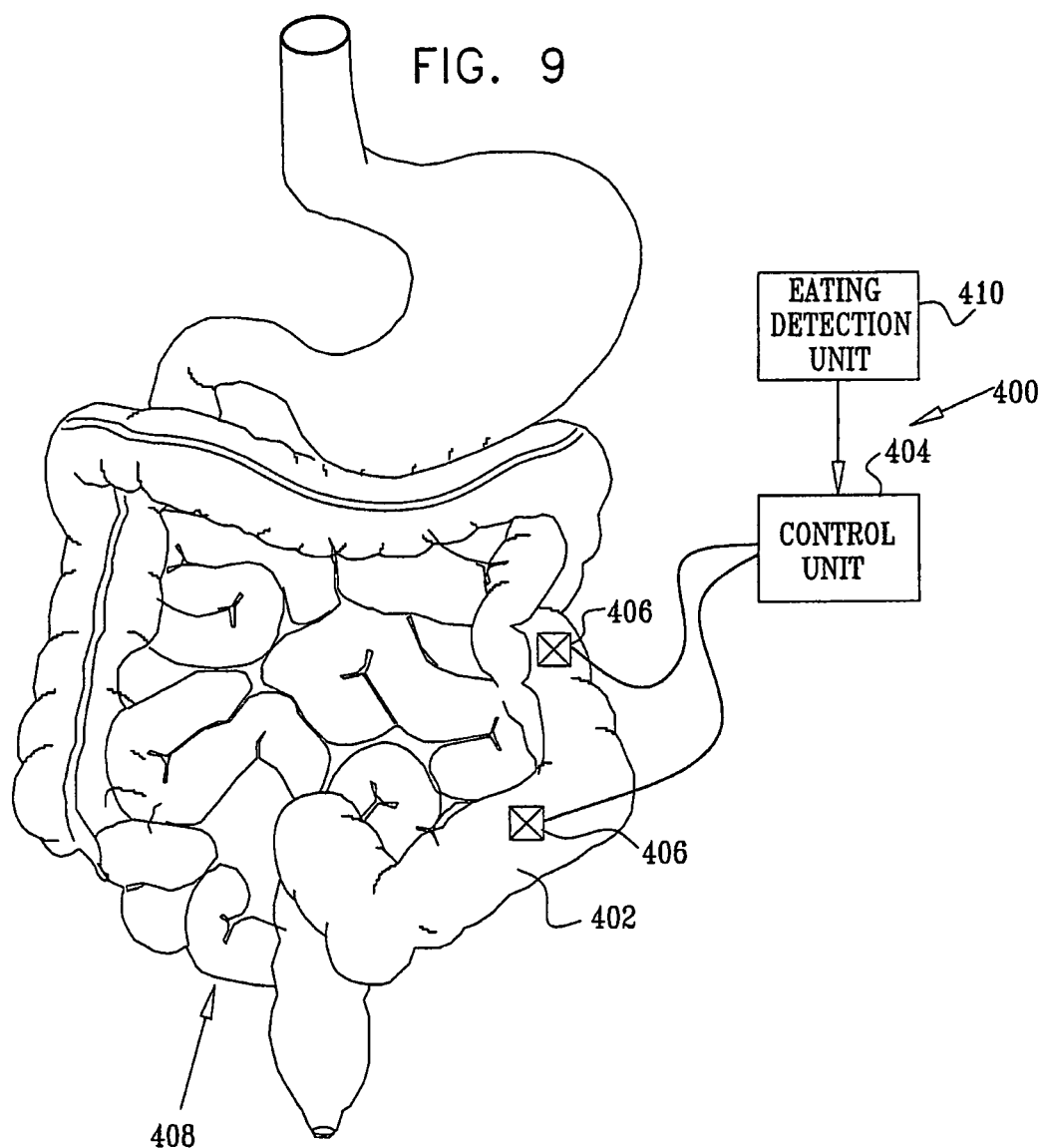
FIG. 9 is a schematic illustration of a colonic stimulation system applied to a colon of a patient, in accordance with an embodiment of the present invention.

Reference is now made to FIG. 9, which is a schematic illustration of a colonic stimulation system 400 applied to a colon 402 of a patient, in accordance with an embodiment of the present invention. System 400 comprises a control unit 404 and one or more electrodes 406, which are driven by control unit 404 to apply an electrical signal to respective sites on or in a vicinity of colon 402 or a distal small intestine 408 of the patient. Control unit 404 configures the signals to stimulate L-cells, which, responsive to such stimulation, increase secretion of glucagon-like-peptide-1 (GLP-1). Such secretion of GLP-1 generally improves glycemic control of the patient, and therefore serves to treat patients suffering from insulin-resistance-related conditions, such as obesity, NIDDM, heart disease, and hypertension, or healthy patients considered at risk for such conditions. Alternatively or additionally, the secretion of GLP-1 induces proliferation of beta cells, thereby improving pancreatic function.

Using known calibration and optimization procedures, a range of suitable waveforms could be determined by a person of ordinary skill in the art who has read the disclosure of the present patent application. For some applications, the electrical signals are applied in bursts of pulses, where the frequency of the pulses within each burst is typically between about 1 and 200 Hz. In an embodiment, this frequency is between about 5 and 50 Hz. Each burst is typically spaced from a following burst by a spacing of approximately 1-15 seconds. For some applications, pre-selected parameters are fixed, or varied occasionally (for example, upon a visit to a physician). For other applications, the parameters are varied in real time. In one such application, detection of eating, excessive eating, or high glucose levels causes control unit 404 to increase the frequency of the pulses in each burst and/or to decrease the spacing between successive bursts.

In an embodiment, signals are applied to the colon using signal parameters described in the above-referenced PCT Patent Publication WO 99/03533 to Ben-Haim et al., entitled, "Smooth muscle controller," and U.S. patent application Ser. No. 09/481,253. In this embodiment, natural electrical activity of the colon is typically sensed, and an ETC signal is applied responsive thereto.

In an embodiment of the present invention, colonic stimulation system 400 further comprises an eating detection unit 410, which is adapted to detect eating by the patient. Control unit 404 is configured to drive electrodes 406 responsive to the detection of eating. The control unit typically drives the electrodes to begin stimulation (a) substantially simultaneously with the commencement of eating, (b) between about one and about 5 minutes after the commencement of eating, or (c) between about one and about 5 minutes prior to commencement of eating. (Option (c) is possible because some of the techniques for eating detection described hereinbelow detect the anticipation of imminent eating.)

Eating detection unit 410 detects eating using (a) one or more of the techniques described hereinabove, (b) eating detection techniques known in the art, and/or (c) eating detection techniques described in one or more of the following patents and patent application publications:

the above-mentioned '414 patent application publication;
the above-mentioned PCT Publication WO 02/082968;
the above-mentioned PCT Publication WO 02/053093;
the above-mentioned U.S. Provisional Patent Application entitled, "Hepatic device for treatment and eating detection," filed on Jun. 20, 2003;
U.S. Provisional Patent Application 60/259,925, filed Jan. 5, 2001, entitled, "Regulation of eating habits," which is assigned to the assignee of the present application and is incorporated herein by reference;
a U.S. provisional patent application, entitled, "Gastrointestinal methods and apparatus for use in treating disorders," filed Jun. 20, 2003, which is assigned to the assignee of the present patent application and is incorporated herein by reference, and/or
the patents, patent application publications, and/or articles mentioned in the Background of the Invention section hereinabove.

In another embodiment of the present invention, control unit 404 is configured to drive electrodes 406 generally constantly, not responsive to detection of eating. Alternatively, the stimulation is applied periodically, such as once to several times an hour, during certain times of day or night, or in response to a command from the subject.

Figure 10:
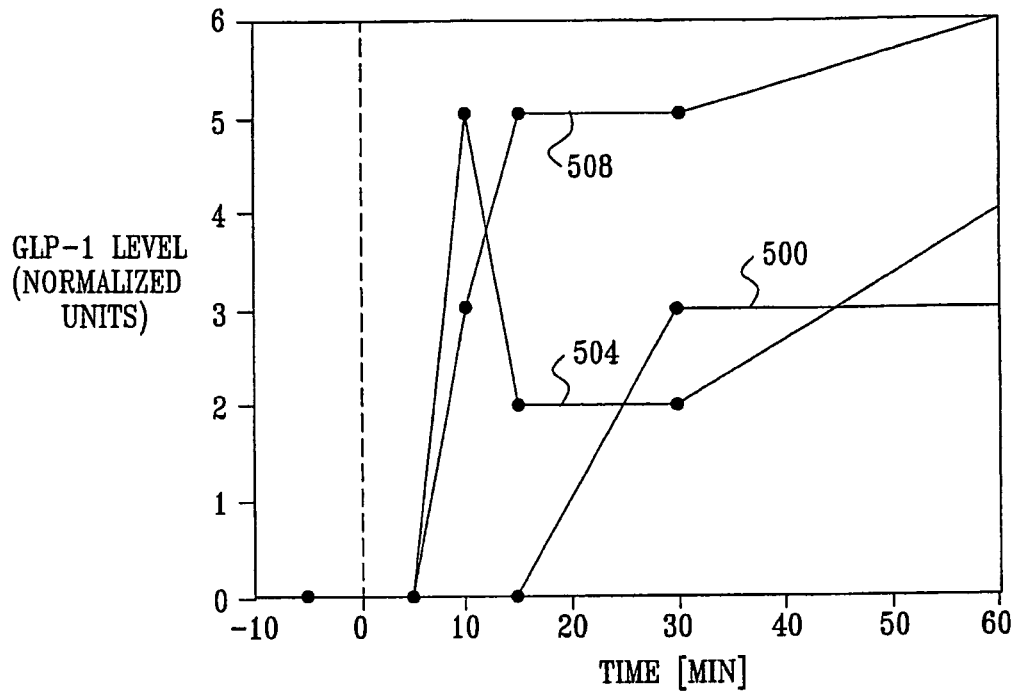
FIGS. 10 and 11 are graphs showing measurements of hormone levels taken during experiments performed in accordance with an embodiment of the present invention.
Figure 11:
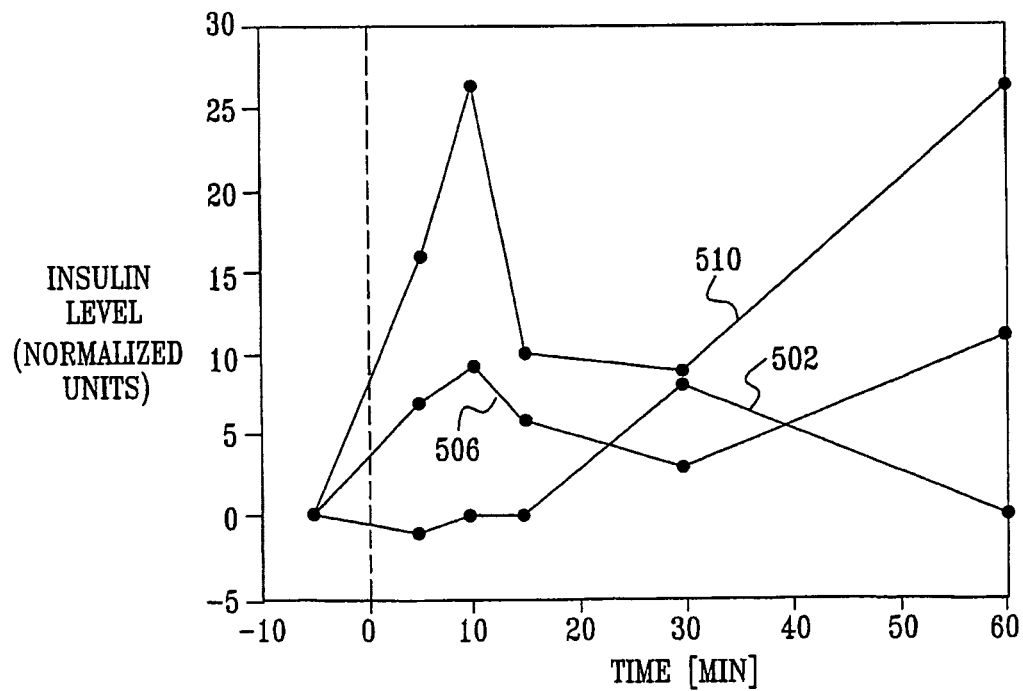

Reference is made to FIGS. 10 and 11, which are graphs showing measurements of hormone levels taken during experiments performed in accordance with an embodiment of the present invention. A single dog was anesthetized, and two pacing electrodes were implanted on an external surface of the distal colon of the dog. The electrodes were driven to apply non-synchronized stimulation with a sweep in parameters, ranging from 1 to 10 mA, at 5-200 Hz.

Measurements were taken on three separate days, each following twenty-four-hour fasting, while the dog was conscious. Stimulation was applied on two of these days, and the third day served as a control. On each of the days, eating began at time 0 and continued for about 10 minutes. The graphs in FIGS. 10 and 11 show GLP-1 levels and insulin levels, respectively, as measured during the same respective experiments on these three days. A line 500 (FIG. 10) and a line 502 (FIG. 11) show the measurements taken on the control day. The y-axis in each graph is labeled "normalized units." This indicates that the baseline values of GLP-1 and insulin (i.e., the measured values at T=−5 minutes) were subtracted from the respective data sets. Thus, the graphs show the increase from baseline of GLP-1 and insulin.

On the two stimulation days, stimulation was applied for 20 minutes beginning substantially simultaneously with the commencement of eating (at 0 minutes). A line 504 (FIG. 10) and a line 506 (FIG. 11) show the measurements taken on one of the stimulation days, while a line 508 (FIG. 10) and a line 510 (FIG. 11) show the measurements taken on the other stimulation day. As can be seen, there is a strong correlation between GLP-1 and insulin levels on all three days. Colonic stimulation enhanced GLP-1 and insulin peaks, and caused GLP-1 and insulin levels to rise earlier after the commencement of eating than occurred without such stimulation. In particular, GLP-1 and insulin levels had risen within 10 minutes of the onset of stimulation, while a measured response on the control day did not occur until 30 minutes after eating started.

Figure 12:
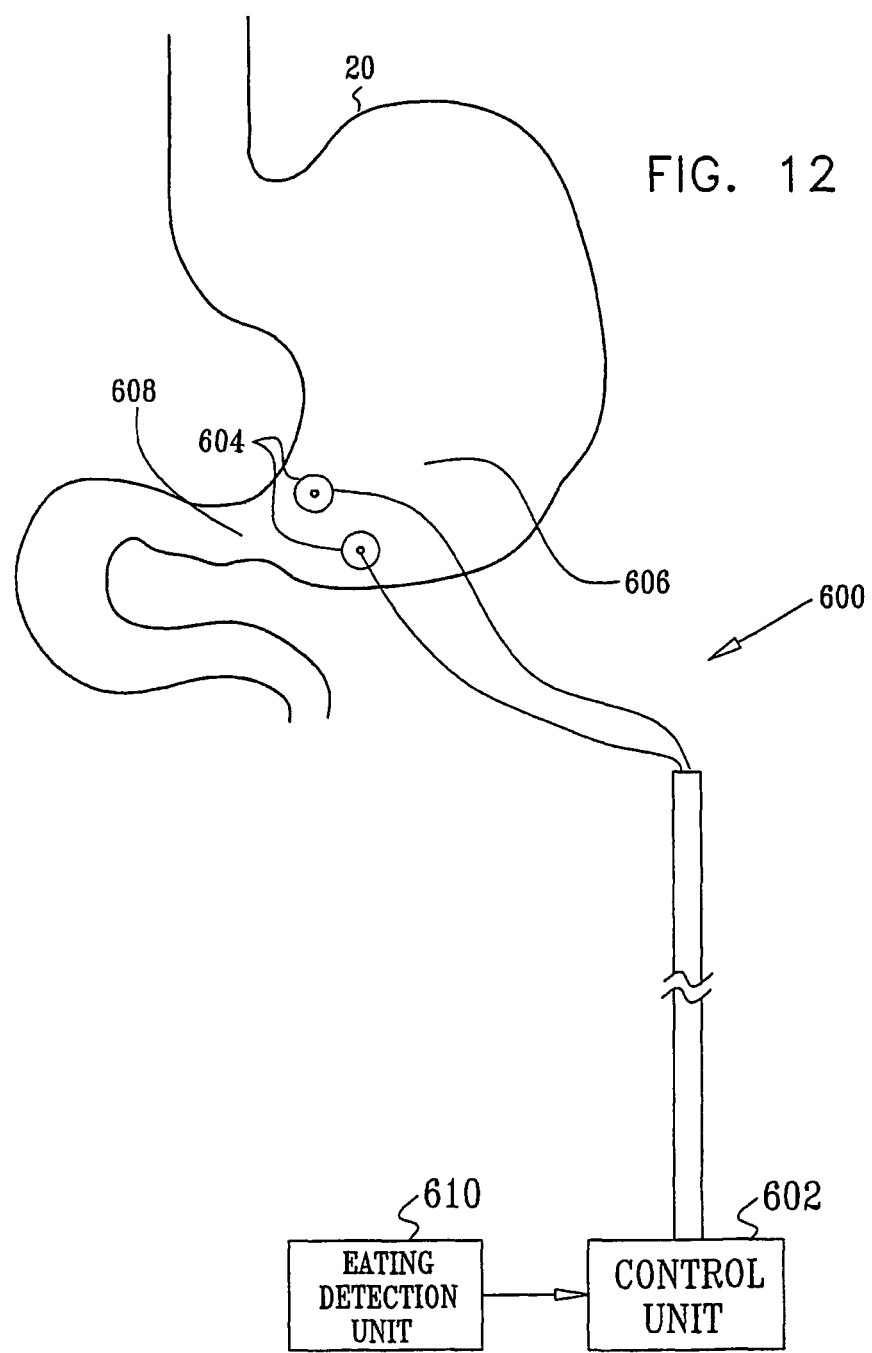
FIG. 12 is a schematic illustration of a stomach signal application system applied to a stomach of a patient, in accordance with an embodiment of the present invention.

Reference is now made to FIG. 12, which is a schematic illustration of a stomach signal application system 600 applied to stomach 20, in accordance with an embodiment of the present invention. System 600 comprises a control unit 602 and one or more electrodes 604, which are driven by control unit 602 to apply an Excitable-Tissue Control (ETC) signal to respective sites on or in a vicinity of stomach 20, responsive to detection of natural electrical activity of the stomach. For example, electrodes 604 may be applied to an anterior wall of an antrum 606 of stomach 20, such as in a vicinity of a pylorus 608 of the patient.

Control unit 602 configures the ETC signal to reduce a blood glucose level of the patient. Such an improvement in glycemic control of the patient is generally useful for treating patients suffering from insulin-resistance-related conditions, such as obesity, NIDDM, heart disease, and hypertension, or healthy patients considered at risk for such conditions.

In an embodiment, the ETC signals are applied to the stomach using signal parameters described in the above-referenced PCT Patent Publication WO 99/03533 to Ben-Haim et al. and U.S. patent application Ser. No. 09/481,253. For some applications, control unit 602 configures the ETC signal to have a waveform having between about 1 and about 150 biphasic pulses, e.g., 100 pulses, each phase of each pulse having an amplitude of between about 3 mA and about 12 mA, e.g., about 8 mA, and a duration of between about 3 ms and about 10 ms, e.g., 6 ms. For some applications, the waveform is applied following detection of the onset of each slow wave of stomach 20 (typically about 3 times per minute). For some applications, pre-selected parameters are fixed, or varied occasionally (for example, upon a visit to a physician). For other applications, the parameters are varied in real time.

In an embodiment of the present invention, stomach signal application system 600 further comprises an eating detection unit 610, which is adapted to detect eating by the patient. Control unit 602 is configured to drive electrodes 604 responsive to the detection of eating. The control unit typically drives the electrodes to begin stimulation (a) substantially simultaneously with the commencement of eating, (b) between about one and about 5 minutes after the commencement of eating, or (c) between about one and about 5 minutes prior to commencement of eating. (Option (c) is possible because some of the techniques for eating detection described herein detect the anticipation of imminent eating.)

Eating detection unit 610 detects eating using (a) one or more of the techniques described hereinabove, (b) eating detection techniques known in the art, and/or (c) eating detection techniques described in one or more of the following patents and patent application publications:

the above-mentioned '414 patent application publication;

the above-mentioned PCT Publication WO 02/082968;
the above-mentioned PCT Publication WO 02/053093;
the above-mentioned U.S. Provisional Patent Application entitled, "Hepatic device for treatment and eating detection," filed on Jun. 20, 2003;
the above-mentioned U.S. Provisional Patent Application 60/259,925;
the above-mentioned U.S. Provisional Patent Application, entitled, "Gastrointestinal methods and apparatus for use in treating disorders," filed on Jun. 20, 2003, and/or
the patents, patent application publications, and/or articles mentioned in the Background of the Invention section hereinabove.

In another embodiment of the present invention, control unit 602 is configured to drive electrodes 604 generally constantly, not responsive to detection of eating. Alternatively, the stimulation is applied periodically, such as once to several times an hour, during certain times of day or night, or in response to a command from the subject.

Figure 13:
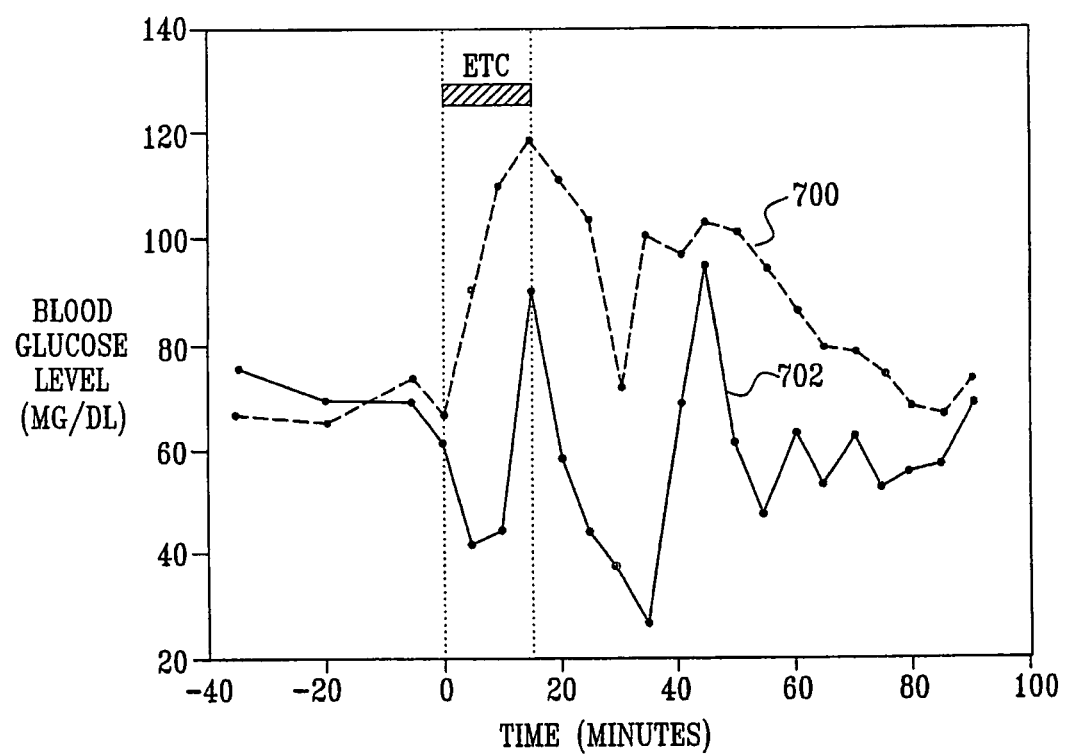
FIGS. 13 and 14 are graphs showing measurements of blood glucose levels taken during experiments performed in accordance with an embodiment of the present invention.

Reference is made to FIG. 13, which is a graph showing measurements of blood glucose levels taken during experiments performed in accordance with an embodiment of the present invention. A single dog was anesthetized, and 2 electrodes were implanted on an external anterior wall of the antrum of the dog, between about 2 cm and about 3 cm from the pylorus. The electrodes were driven to apply an ETC signal with a square waveform having 100 biphasic pulses, each phase of each pulse having an amplitude of 8 mA and a duration of 6 ms. The waveform was applied following detection of the onset of each slow wave of the stomach of the dog (about 4 to 5 times per minute).

Measurements were taken on two separate days, at about the same time on each day, following twelve-hour fasting, while the dog was conscious. An ETC signal was applied on one of these days, and the other day served as a control. On each of the days, eating began at time 0 and continued for about two minutes. The ETC signal was applied beginning at time 0 and continuing for about 15 minutes. Measurements were taken using the same glucose meter on both days, and validation of each measurement was performed using two different sets of measurement kits.

A dashed line 700 and a solid line 702 show the measurements taken on the control day and the signal application day, respectively. As can be seen, application of the ETC signal resulted in a substantial reduction in blood glucose level at all points during the measurement period.

Figure 14:
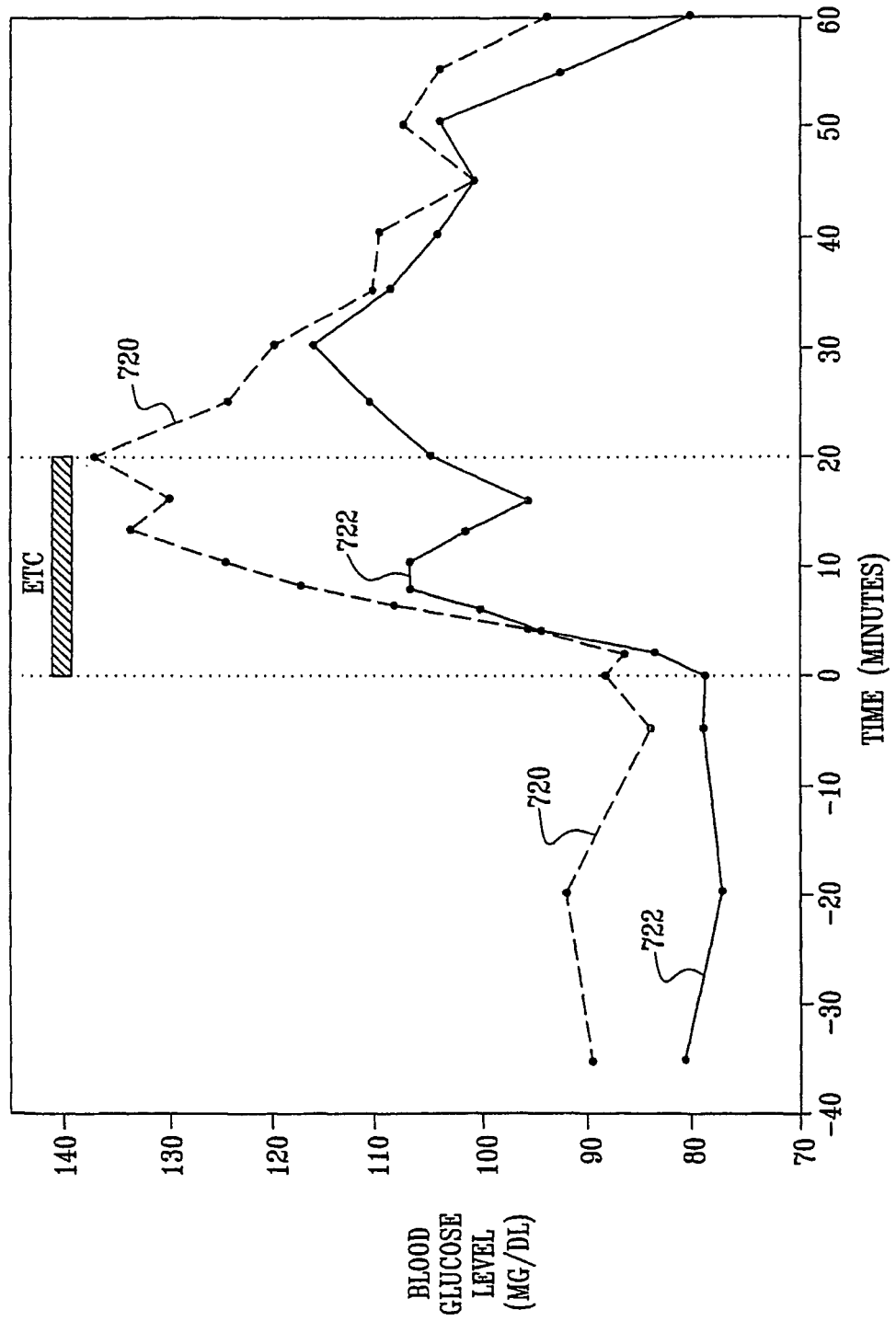

Reference is made to FIG. 14, which is a graph showing measurements of blood glucose levels taken during experiments performed in accordance with an embodiment of the present invention. A second dog, different from the dog described with reference to FIG. 13, was anesthetized, and 2 electrodes were implanted on an external anterior wall of the antrum of the dog. The electrodes were implanted between about 2 cm and about 3 cm from the pylorus. An ETC signal like that described with reference to FIG. 13 was applied, and the same experimental protocol was followed. In the experiment whose results are shown in FIG. 14, however, the ETC signal was applied for approximately 20 minutes.

A dashed line 720 and a solid line 722 show the measurements taken on the control day and the signal application day, respectively. As can be seen, application of the ETC signal resulted in a substantial reduction in blood glucose level during the measurement period.

Although the experiments described hereinabove with reference to FIGS. 13 and 14 include applying an ETC signal to the stomach, reduction of blood glucose by application of an ETC signal to other sites on or in the gastrointestinal tract is considered to be within the scope of the present invention, as well. For example, an ETC signal may be applied to the colon, or to a site of the small intestine, such as the duodenum. Alternatively or additionally, for some applications, an ETC signal is applied to smooth muscle not of the gastrointestinal tract, or an ETC signal is applied to cardiac muscle tissue.

Figure 15:
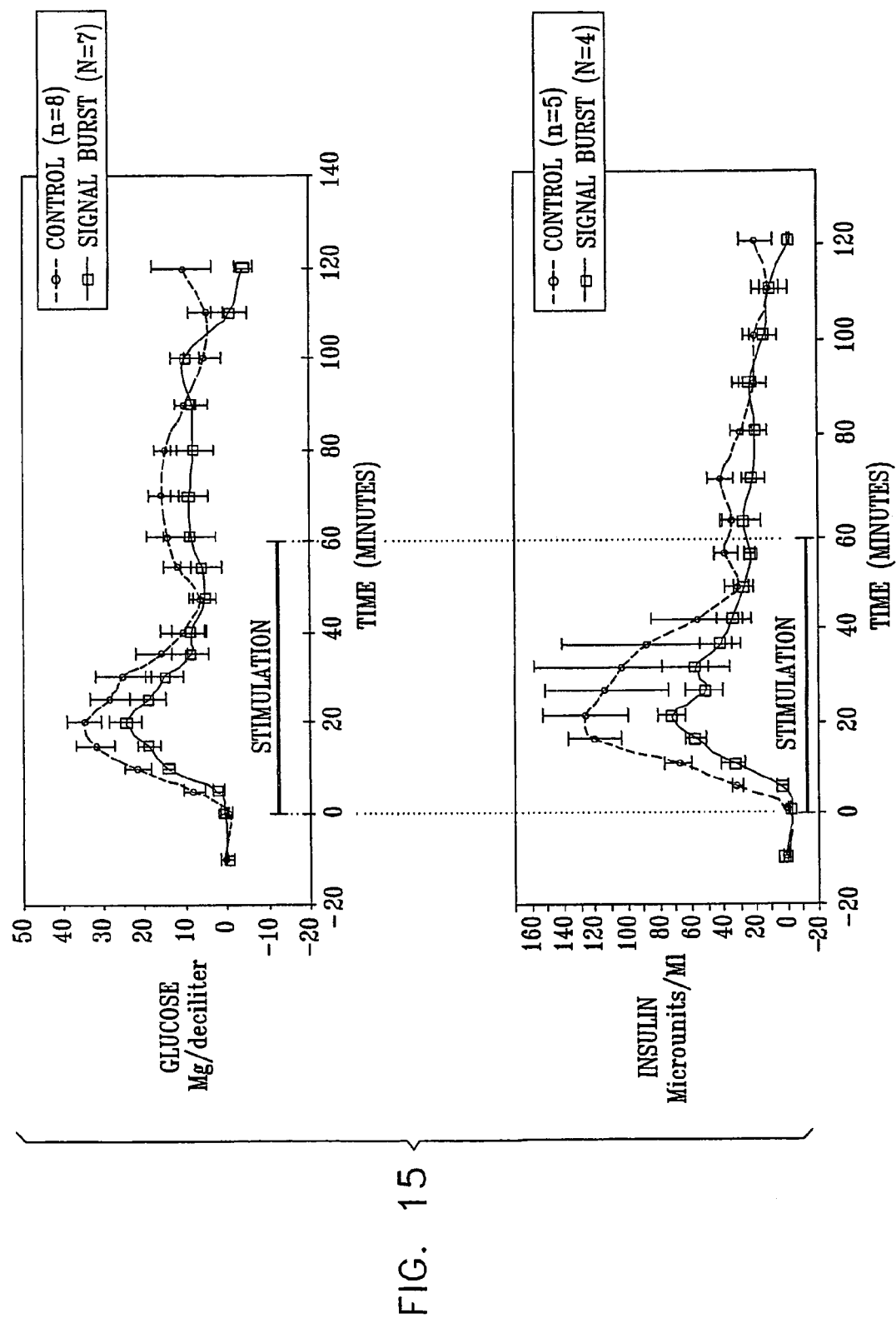
FIG. 15 is a graph showing measurements of blood glucose and insulin levels taken during experiments performed in accordance with an embodiment of the present invention.

FIG. 15 is a two-part graph showing measurements of blood glucose and blood insulin levels taken during experiments performed in accordance with an embodiment of the present invention. For these experiments, a single Sinclair minipig had four pairs of electrodes sutured to its stomach, one pair on the anterior side of the antrum, one pair on the posterior side of the antrum, one pair on the anterior side of the corpus, and one pair on the posterior side of the corpus. (It is noted that in these experiments, the electrical potential of both electrodes in any given pair of electrodes was equal.) Antral electrical activity was sensed by means of summing the signal recorded by the electrode pairs sutured to the antrum. A normal rate of antral electrical activity was determined to be approximately every 14 seconds.

At time zero (as shown in FIG. 15), the mimipig was administered an oral glucose tolerance test (OGTT), and, at the same time, a 60 minute stimulation period was initiated. At the beginning of the stimulation period, antral electrical activity characteristic of a slow wave was recorded, and, in response, an initiating monophasic pulse (5 mA, 100 ms) was applied between the electrodes on the corpus and the electrodes on the antrum. After a delay of 300 ms, a signal burst was applied between the electrodes on the corpus and the electrodes on the antrum. The signal burst was composed of biphasic pulses, each biphasic pulse having a positive 5 ms portion and a negative 5 ms portion. The magnitude of each portion was 5 mA. The pulse repetition interval (duration between the onset of each successive biphasic pulse) was set at 200 ms, such that the frequency of the signal burst was 5 Hz. The burst lasted 4 seconds.

Subsequently, a second initiating pulse was applied twelve seconds after the first initiating pulse, i.e., approximately 20% earlier than the next slow wave would typically be expected to be recorded. The second initiating pulse was also followed by a signal burst, as described hereinabove. (In an embodiment for which experiments have not been performed, values between 10% and 30% are used.) The second initiating pulse and/or associated signal burst triggered antral electrical activity to occur which was measured and which appeared characteristic of a slow wave. Subsequently, additional initiating pulses and signal bursts were applied at 12 second intervals, for the remainder of the 60 minute stimulation period.

Blood samples were taken approximately every 7 minutes, prior to, during, and following the stimulation period. In the upper graph of FIG. 15, glucose levels are shown that were measured in fifteen experiments (control: n=8; experimental group: n=7). In the lower graph of FIG. 15, insulin levels are shown that were measured in nine experiments (control: n=5; experimental group: n=4). (Because these experiments were carried out shortly before the filing date of the present patent application, laboratory analysis of the insulin levels from the remaining experiments have not yet been obtained.) The fifteen experiments were carried out by alternating (a) an experimental protocol, in which the initiating pulses and signal bursts described hereinabove were applied, and (b) a control protocol, in which no signal was applied. All experiments were spaced by at least 48 hours.

In both the glucose and the insulin graphs of FIG. 15, data are shown with respect to a baseline set to zero. Error bars represent standard error of the mean. FIG. 15 shows that the experimental group (to which the initiating pulses and signal bursts were applied as described hereinabove in accordance with an embodiment of the present invention) had substantially lower levels of blood glucose and blood insulin than did the control group.

In an embodiment, antral electrical activity is not sensed in a patient, but the initiating pulses and signal bursts are applied at intervals 10-30% faster than a normal slow wave cycle in the patient. For some applications, the initiating pulses and signal bursts are applied not responsively to any measured gastrointestinal tract activity.

In an embodiment, instead of or in addition to the 5 ms pulse durations described with respect to FIG. 15, the pulse duration is set to 1 to 10 ms, e.g., 5 to 6 ms.

In an embodiment, instead of or in addition to the 5 mA pulses described with respect to FIG. 15, the pulse amplitude is set to 2 to 15 mA.

In an embodiment, instead of or in addition to the 300 ms delay between the initiating pulse and the signal burst described with respect to FIG. 15, the delay is set to 100 to 4000 ms, e.g., 100 to 800 ms.

In an embodiment, instead of or in addition to the 100 ms pulse duration of the initiating pulse described with respect to FIG. 15, the pulse duration of the initiating pulse is set to 50 to 500 ms.

In an embodiment, instead of or in addition to the 4 second signal burst duration described with respect to FIG. 15, the burst duration is set to 1 to 6 seconds.

In an embodiment, instead of or in addition to the 5 Hz frequency of the signal burst described with respect to FIG. 15, the frequency of the signal burst is set to 1 to 30 Hz, e.g., 1 to 15 Hz.

In an embodiment, instead of or in addition to the 5 Hz frequency of the signal burst described with respect to FIG. 15, the frequency of the signal burst is set to 30 to 200 Hz, e.g., 60 to 120 Hz, e.g., 80 Hz.

In an embodiment, the initiating pulse as described with respect to FIG. 15 is not followed by a signal burst.

In an embodiment, electrical activity of the corpus is sensed, in addition to or instead of sensing antral electrical activity.

In an embodiment, signal bursts are applied between electrodes on the corpus and electrodes on the antrum. For example, the electrodes may be placed on: (a) a posterior portion of the antrum and a posterior portion of the corpus; (b) a posterior portion of the antrum and an anterior portion of the corpus; (c) a posterior portion of the corpus and an anterior portion of the antrum; and/or (d) an anterior portion of the corpus and an anterior portion of the antrum.

Alternatively or additionally, signal bursts are applied between one or more electrodes on one portion of the corpus (e.g., a posterior portion) and one or more electrodes on another portion of the corpus (e.g., an anterior portion). Alternatively or additionally, signal bursts are applied between one or more electrodes on one portion of the antrum (e.g., a posterior portion) and one or more electrodes on another portion of the antrum (e.g., an anterior portion).

For some applications, techniques described herein are practiced in combination with techniques described in one or more of the following, which are assigned to the assignee of the present patent application and are incorporated herein by reference: U.S. Provisional Patent Application 60/123,532, PCT Patent Application IL00/00132, PCT Patent Application IL00/00566, PCT Patent Application IL03/00736, U.S. patent application Ser. No. 09/914,889, or U.S. patent application Ser. No. 10/237,263.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a subject, comprising:
a set of one or more electrodes, adapted to be applied to respective sites of a stomach of the subject; and
a control unit, adapted to drive the electrode set to apply to the respective sites of the stomach, as a train of biphasic pulses, an electrical signal configured to reduce a blood glucose level of the subject compared to the blood glucose level if the electrical signal were not applied, if the subject were to consume a same quantity of glucose with and without application of the electrical signal.

2. The apparatus according to claim 1, wherein the control unit is adapted to drive the electrode set to apply an Excitable-Tissue Control (ETC) signal.

3. The apparatus according to claim 1, wherein the control unit is adapted to drive the electrode set to apply the electrical signal in pulses in a pulse train, and to configure a length of the pulse train to be between 1 and 6 seconds.

4. The apparatus according to claim 3, wherein the control unit is adapted to configure the length of the pulse train to be between 3 and 6 seconds.

5. The apparatus according to claim 1, wherein the control unit is adapted to detect physiological parameters of the subject and drive the electrode set to apply the electrical signal responsive thereto.

6. The apparatus according to claim 5, wherein the physiological parameters are indicative of ingestion by the subject.

7. The apparatus according to claim 5, further comprising a set of one or more sensors, configured to be placed on or in a gastrointestinal tract of the subject, and to detect the physiological parameters.

8. The apparatus according to claim 7, wherein the control unit is adapted to detect a slow wave of the stomach.

9. The apparatus according to claim 1, wherein the control unit is configured to detect eating by the subject, and to apply the electrical signal responsive to detecting the eating.

10. The apparatus according to claim 1, wherein the electrodes are configured to be applied to the respective stomach sites in a vicinity of a pylorus of the subject.

11. The apparatus according to claim 1, wherein the electrodes are configured to be applied to an antrum of the stomach.

12. The apparatus according to claim 1, wherein the control unit is adapted to drive the electrode set to apply the electrical signal to the respective sites of the stomach, following detection of onset of each slow wave of the stomach.

13. The apparatus according to claim 1, wherein the control unit is adapted to drive the electrode set to apply the electrical signal in pulses and to configure a pulse amplitude of the pulses to be between 3 to 12 mA.

14. The apparatus according to claim 1, wherein the control unit is adapted to set a duration of each phase of the biphasic pulses to be between 3 and 10 ms.

15. The apparatus according to claim 1, wherein the control unit is adapted to drive the electrode set to apply five or more pulses to the site during each of a plurality of slow wave cycles of the stomach.

16. The apparatus according to claim 1, wherein the one or more electrodes are adapted to be inserted into the muscular layer of the stomach.

17. The apparatus according to claim 1, wherein the control unit is adapted to configure the electrical signal to reduce the blood glucose level throughout a period of time that includes a point in time at approximately 7 minutes after commencement of application of the electrical signal.

18. Apparatus for treating a subject, comprising:
a set of electrodes that comprises at least a first electrode, adapted to be implanted at a gastric corpus site, and at least a second electrode, adapted to be implanted at a gastric antrum site; and
a control unit, configured to drive, between the at least a first electrode at the gastric corpus site and the at least a second electrode at the gastric antrum site, an electrical signal configured to reduce a rise in a blood glucose level of the subject.

19. The apparatus according to claim 18, wherein the at least at least a first electrode and the at least a second electrode are adapted to be inserted into the muscular layer of the stomach.

20. The apparatus according to claim 18, wherein the control unit is adapted to configure the electrical signal to reduce the rise in the blood glucose level throughout a period of time that includes a point in time at approximately 7 minutes after commencement of application of the electrical signal.

21. Apparatus for treating a subject, comprising:
a set of at least one electrode, adapted to be applied to a respective at least one stomach site of the subject; and
a control unit, adapted to drive the electrode set to apply, to the respective at least one stomach site, an electrical signal configured to reduce a rise in a blood glucose level of the subject,
wherein the control unit is adapted to drive the electrode set to apply the electrical signal as a train of biphasic pulses, and
wherein the control unit is adapted to set a duration of each phase of the biphasic pulses to be between 3 and 10 ms.

22. The apparatus according to claim 21, wherein the electrode set comprises a first electrode, adapted to be implanted at a first gastric corpus site, and a second electrode, adapted to be implanted at a second gastric corpus site.

23. The apparatus according to claim 21, wherein the control unit is adapted to configure the electrical signal to reduce a rise in a blood insulin level of the subject.

24. The apparatus according to claim 21, wherein the control unit is adapted to drive the electrode set to apply five or more pulses to the site during each of a plurality of slow wave cycles of the stomach.

25. The apparatus according to claim 21, wherein the control unit is adapted to drive the electrode set to apply 1 to 5 pulses to the site during each of a plurality of slow wave cycles of the stomach.

26. The apparatus according to claim 25, wherein the control unit is adapted to drive the electrode set to apply one pulse to the site during each of the plurality of slow wave cycles.

27. The apparatus according to claim 21, wherein the control unit is adapted to configure a frequency of the electrical signal to be between 1 and 30 Hz.

28. The apparatus according to claim 27, wherein the control unit is adapted to configure the frequency to be between 10 and 30 Hz.

29. The apparatus according to claim 27, wherein the control unit is adapted to configure the frequency to be between 1 and 10 Hz.

30. The apparatus according to claim 29, wherein the control unit is adapted to configure the frequency to be between 2.5 and 7.5 Hz.

31. The apparatus according to claim 21, wherein the control unit is adapted to configure a frequency of the electrical signal to be between 30 and 200 Hz.

32. The apparatus according to claim 31, wherein the control unit is adapted to configure the frequency to be between 100 and 200 Hz.

33. The apparatus according to claim 31, wherein the control unit is adapted to configure the frequency to be between 30 and 100 Hz.

34. The apparatus according to claim 33, wherein the control unit is adapted to configure the frequency to be between 60 and 100 Hz.

35. The apparatus according to claim 21, wherein the control unit is adapted to drive the electrode set to apply the electrical signal in pulses and to configure a pulse amplitude of the pulses to be between 2 and 15 mA.

36. The apparatus according to claim 35, wherein the control unit is adapted to configure the pulse amplitude to be between 2.5 and 7.5 mA.

37. The apparatus according to claim 21, wherein the control unit is adapted to set the duration of each phase of the biphasic pulses to be between 4 and 6 ms.

38. The apparatus according to claim 21, wherein to drive the electrode set to apply the electrical signal, the control unit is adapted to: drive the electrode set to apply an initiating pulse; and drive the electrode set to apply a burst of pulses at least 100 ms following a termination of the initiating pulse.

39. The apparatus according to claim 38, wherein the control unit is adapted to drive the electrode set to apply the initiating pulse not responsively to any physiological attribute of the subject sensed within one minute prior to the applying of the initiating pulse.

40. The apparatus according to claim 38, wherein the control unit is adapted to drive the electrode set to apply the initiating pulse not responsively to any sensing of a slow wave within one minute prior to the applying of the initiating pulse.

41. The apparatus according to claim 38, wherein the control unit is adapted to configure a frequency of the burst of pulses to be between 1 and 10 Hz.

42. The apparatus according to claim 38, wherein the control unit is adapted to configure a frequency of the burst of pulses to be between 10 and 100 Hz.

43. The apparatus according to claim 38, wherein the control unit is adapted to detect a physiological attribute of the subject and drive the electrode set to apply the initiating pulse response thereto.

44. The apparatus according to claim 43, wherein to detect the physiological attribute, the control unit is adapted to detect a gastrointestinal tract attribute of the subject.

45. The apparatus according to claim 44, wherein to detect the gastrointestinal tract attribute, the control unit is adapted to detect an indication of a slow wave of the stomach.

46. The apparatus according to claim 44, wherein to detect the gastrointestinal tract attribute, the control unit is adapted to detect an indication of eating by the subject.

47. The apparatus according to claim 38, wherein the control unit is adapted to drive the electrode set to initiate applying the burst of pulses less than 4 seconds following the termination of the initiating pulse.

48. The apparatus according to claim 47, wherein the control unit is adapted to drive the electrode set to initiate applying the burst of pulses between 100 and 500 ms following the termination of the initiating pulse.

49. The apparatus according to claim 38, wherein the control unit is adapted to configure a duration of the initiating pulse to be between 50 and 500 ms.

50. The apparatus according to claim 49, wherein the control unit is adapted to configure the duration to be between 50 and 150 ms.

51. The apparatus according to claim 21, wherein the control unit is adapted to drive the electrode set to apply an Excitable-Tissue Control (ETC) signal.

52. The apparatus according to claim 21, wherein the at least one electrode is adapted to be inserted into the muscular layer of a stomach of the subject.

53. The apparatus according to claim 21, wherein the control unit is adapted to configure the electrical signal to reduce the rise in the blood glucose level throughout a period of time that includes a point in time at approximately 7 minutes after commencement of application of the electrical signal.

* * * * *